US012661348B2

(12) United States Patent
Greinwald et al.

(10) Patent No.: US 12,661,348 B2
(45) Date of Patent: Jun. 23, 2026

(54) SYSTEMIC FORMULATION OF A PYRIDINONE DERIVATE FOR TG2-RELATED DISEASES

(71) Applicants: Dr. Falk Pharma GmbH, Freiburg (DE); Zedira GmbH, Darmstadt (DE)

(72) Inventors: Roland Greinwald, Kenzingen (DE); Martin Hils, Darmstadt (DE); Wolfgang Mohr, Freiburg (DE); Ralf Pasternack, Griesheim (DE); Bernhard Tewes, Vörstetten (DE); Rudolf Wilhelm, Bischweier (DE)

(73) Assignees: Dr. Falk Pharma GmbH, Freiburg (DE); Zedira GmbH, Darmstadt (DE)

( * ) Notice: Subject to any disclaimer, the term of this patent is extended or adjusted under 35 U.S.C. 154(b) by 681 days.

(21) Appl. No.: 17/996,775

(22) PCT Filed: Apr. 24, 2021

(86) PCT No.: PCT/EP2021/060764

§ 371 (c)(1),
(2) Date: Oct. 20, 2022

(87) PCT Pub. No.: WO2021/214338

PCT Pub. Date: Oct. 28, 2021

(65) Prior Publication Data

US 2023/0165845 A1 Jun. 1, 2023

(30) Foreign Application Priority Data

Apr. 24, 2020 (EP) ..................................... 20171441
Dec. 3, 2020 (EP) ..................................... 20211697

(51) Int. Cl.
*A61K 31/4439* (2006.01)
*A61K 9/00* (2006.01)
*A61P 1/16* (2006.01)
*A61P 13/12* (2006.01)

(52) U.S. Cl.
CPC ........ *A61K 31/4439* (2013.01); *A61K 9/0053* (2013.01); *A61P 1/16* (2018.01); *A61P 13/12* (2018.01)

(58) Field of Classification Search
CPC .................................................. A61K 31/4439
See application file for complete search history.

(56) References Cited

U.S. PATENT DOCUMENTS

| | | | | |
|---|---|---|---|---|
| 9,434,763 | B2 * | 9/2016 | Buchold | A61P 7/02 |
| 2011/0229568 | A1 | 9/2011 | Oertel | |
| 2015/0203535 | A1 * | 7/2015 | Buchold | C07D 213/75 530/331 |
| 2023/0165844 | A1 | 6/2023 | Greinwald et al. | |

FOREIGN PATENT DOCUMENTS

| | | | |
|---|---|---|---|
| CN | 104603109 | A | 5/2015 |
| EP | 2687511 | | 1/2014 |
| EP | 3210599 | A1 | 8/2017 |
| JP | 2003252797 | A | 9/2003 |
| JP | 2011529445 | A | 12/2011 |
| JP | 2015529645 | A | 10/2015 |
| JP | 2017502062 | A | 1/2017 |
| JP | 2018519279 | A | 7/2018 |
| JP | 2019001787 | A | 1/2019 |
| WO | WO-2011102504 | A1 | 8/2011 |
| WO | WO-2018122419 | A1 | 7/2018 |
| WO | WO 2019/202052 | | 10/2019 |
| WO | WO-2020027011 | A1 | 2/2020 |
| WO | WO-2021/214337 | A1 | 10/2021 |
| WO | WO-2023072878 | A1 | 5/2023 |

OTHER PUBLICATIONS

Warren, D. B., et al., "Using Polymeric Precipitation Inhibitors to Improve the Absorption of Poorly Water-Soluble Drugs: A Mechanistic Basis for Utility," Journal of Drug Targeting 18(10):704-731, Informa UK, Ltd., United Kingdom (2010).
Peterson, B., et al., "Drug Bioavailability Enhancing Agents of Natural Origin (Bioenhancers) that Modulate Drug Membrane Permeation and Pre-Systemic Metabolism," Pharmaceutics 11(33):1-46, MDPI, Switzerland (2019).
Huang et al., "Transglutaminase inhibition ameliorates experimental diabetic nephropathy" Kidney International (2009) 76(4):383-394.
International Search Report and Written Opinion mailed Jul. 2, 2021 in PCT Application No. PCT/EP2021/060764, filed Apr. 24, 2021.
International Search Report and Written Opinion mailed Jul. 1, 2021 in PCT Application No. PCT/EP2021/060763, filed Apr. 24, 2021, European Patent Office, the Netherlands, 8 pages.

(Continued)

*Primary Examiner* — Rei Tsang Shiao
(74) *Attorney, Agent, or Firm* — Sterne, Kessler, Goldstein & Fox P.L.L.C.

(57) ABSTRACT

The present invention relates to a formulation in particular an oral formulation for the prophylaxis and treatment of TG2-related disorders like fibrosis in particular diabetic nephropathy and/or diabetic associated non-alcoholic steatohepatitis (NASH) and/or non-alcoholic steatohepatitis, and its use in the prophylaxis and/or treatment of fibrosis in particular nephropathy, NASH, idiopathic pulmonary fibrosis, and cystic fibrosis. Further, the present application relates also to the use of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate as hepatoprotectant, i.e. as hepatoprotective agent. In addition the present invention relates to a pharmaceutical composition comprising (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate for use as hepatoprotective agent and for use in the protection of the liver against liver toxicity, the improvement of liver function, and/or in the prophylaxis or treatment of a liver disease or liver disorder.

38 Claims, 14 Drawing Sheets

(56) References Cited

OTHER PUBLICATIONS

Luciani, A., et al., "Defective CFTR induces aggresome formation and lung inflammation in cystic fibrosis through ROS-mediated autophagy inhibition," Nature Cell Biology 12:863-875, Macmillan Publishers Limited, United States (2010).
Huang, F., et al., "Particulate Matter and Hospital Admissions for Stroke in Beijing, China: Modification Effects by Ambient Temperature," Journal of the American Heart Association 5:e003437, American Heart Association, United States (2016).
Olsen, K. C., et al., "Inhibition of Transglutaminase 2, a Novel Target for Pulmonary Fibrosis, by Two Small Electrophilic Molecules," American Journal of Respiratory Cell and Molecular Biology 50(4):737-747, American Thoracic Society, United States (2014).
Korpimäki, S., et al. "Gluten-sensitive hypertransaminasemia in celiac disease: an infrequent and often subclinical finding," The American Journal of Gastroenterology 106:1689-1696, The American College of Gastroenterology, United States (2011).
Kahaly, G. J., et al., "Celiac disease and endocrine autoimmunity—the genetic link," Autoimmun. Rev. 17:1169-1175, Elsevier, Netherlands (2018).
Lebwohl, B., et al., "Coeliac disease," Lancet 391:70-81, Elsevier, Netherlands (2018).
Ludvigsson, J. F., et al., "The Oslo definitions for coeliac disease and related terms," Gut 62:43-52, British Medical Association, United Kingdom (2012).
Schuppan, D., et al., "Celiac disease: from pathogenesis to novel therapies," Gastroenterology 137(6):1912-1933, Elsevier, Netherlands (2009).
Lauzier, A., et al., "Transglutaminase 2 Cross-linking Activity is Linked to Invadopodia Formation and Cartilage Breakdown in Arthritis," Arthritis Research & Therapy 14:R159, BioMed Central, United Kingdom (2012).
Sanchez-Lara, A. C., et al., "Feline Chronic Kidney Disease is Associated with Upregulation of Transglutaminase 2: A Collagen Cross-Linking Enzyme," Veterinary Pathology 52(3):513-523, SAGE Publications, United States (2015).
Leffler, D. A., et al., "A validated disease-specific symptom index for adults with celiac disease," Clin. Gastroenterol. Hepatol. 7(12):1328-1334, Elsevier, Netherlands (2009).
Häuser, W., et al., "Development and validation of the Celiac Disease Questionnaire (CDQ), a disease-specific health-related quality of life measure for adult patients with celiac disease," J. Clin. Gastroenterol. 41:157-166, Lippincott Williams & Wilkins, United States (2007).
Daneshpour, N., et al., "Targeted Delivery of a Novel Group of Site-Directed Transglutaminase Inhibitors to the Liver using Liposomes: A New Approach for the Potential Treatment of Liver Fibrosis," Journal of Drug Targeting 19(8):624-631, Informa UK, Ltd., United Kingdom (Sep. 2010).
Ventura, M.A.E., et al., "Su1161—The Oral Transglutaminase 2 (TG2) Inhibitor Zed1227 Blocks TG2 Activity in a Mouse Model of Intestinal Inflammation," Gastroenterology 154(6):S-490, American Gastroenterological Association, United States (May 2018).
Office Action mailed Jun. 16, 2025, in U.S. Appl. No. 17/996,770, inventors Greinwald, R., et al., § 371(c) Date: Oct. 20, 2022, 6 pages.
Huang, Y., et al., "Fundamental Aspects of Solid Dispersion Technology for Poorly Soluble Drugs," Acta Pharmaceutica Sinica B 4(1):18-25 (Dec. 2023).
Leuner, C., et al., "Improving Drug Solubility for Oral Delivery Using Solid Dispersions," European Journal of Pharmaceutics and Biopharmaceutics, 50(1):47-60 (Jul. 2000).
Grenard, P., et al., "Transglutaminase-Mediated Cross-Linking is Involved in the Stabilization of Extracellular Matrix in Human Liver Fibrosis," Journal of Hepatology 35(3):367-375, Elsevier, Netherlands (Sep. 2001).
Mirza, A., et al., "A Role for Tissue Transglutaminase in Hepatic Injury and Fibrogenesis, and its Regulation by NF-kappaB," American Journal of Physiology 272(2 Pt 1):G281-288, American Physiological Society, United States (Feb. 1997).

* cited by examiner

Steatosis Score

Inflammation Score

| Dose [mg/kg] | Cmax* [ng/mL] | AUC [ng/mL*h] |
|---|---|---|
| 100 | 56.4 | 299 |
| 300 | 84.1 | 453 |
| 1000 | 162.1 | 651 |

* Cmax after first administration (tmax: 0.5h)

| Dose | 10 mg | 20 mg | 50 mg | 100 mg |
|---|---|---|---|---|
| $C_{max}$ [ng/mL]* | 59.8±19.2 | 127±45.4 | 375±229 | 840±349 |
| $AUC_{0-t}$ [ng/mL*h]* | 205±50.3 | 442±159 | 1106±694 | 2211±821 |
| $t_{max}$ [h], Median<br>Range | 1.00<br>0.750-2.00 | 1.25<br>0.750-2.00 | 1.00<br>0.500-2.00 | 1.13<br>0.750-2.00 |

| Clinical PK data (CEC-2/BIO) | | $C_{max}$ / $IC_{(10-90)}$ | | |
|---|---|---|---|---|
| Drug level | $C_{max}$ ( ≡ drug conc. at target site) | $IC_{10}$ (18 ng/mL) | $IC_{50}$ (101 ng/mL) | $IC_{90}$ (346.2 ng/mL) |
| 10 mg | 59.8 ng/mL | 3,3 | 0,6 | 0,2 |
| 20 mg | 127.0 ng/mL | 7,1 | 1,3 | 0,4 |
| 50 mg | 375.0 ng/mL | 20,9 | 3,7 | 1,1 |
| 100 mg | 840.0 ng/mL | 46,7 | 8,3 | 2,4 |

Trial design schematic of Example 14

SYSTEMIC FORMULATION OF A PYRIDINONE DERIVATE FOR TG2-RELATED DISEASES

The present application is the national phase entry of PCT Application No. PCT/EP2021/060764, filed Apr. 24, 2021, which claims priority to EP application Nos. 20171441.7, filed Apr. 24, 2020, and 20211697.6, filed Dec. 3, 2020, each of which are incorporated by reference in their entireties.

The present invention relates to a systemic formulation in particular an oral formulation for the prophylaxis and/or treatment TG2-related diseases such as fibrosis in particular nephropathy, fibrotic liver diseases including non-alcoholic fatty liver disease (NAFLD) and non-alcoholic steatohepatitis (NASH), idiopathic pulmonary fibrosis (IPF) and cystic fibrosis, and its use in the prophylaxis and/or treatment of fibrosis in particular nephropathy, fibrotic liver diseases including NAFLD and NASH, idiopathic pulmonary fibrosis and cystic fibrosis.

Further, the present application relates also to the use of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate as hepatoprotectant, i.e. as hepatoprotective agent.

In addition the present invention relates to a pharmaceutical composition comprising (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate for use as hepatoprotective agent and for use in the protection of the liver against liver toxicity, the improvement of liver function, and/or the repair of the liver injury, or in the prophylaxis or treatment of a liver disease or liver disorder as demonstrated by reducing serum levels of hepatic enzymes.

BACKGROUND OF THE INVENTION

Steatohepatitis is a type of fatty liver disease, characterized by inflammation of the liver with concurrent fat accumulation in hepatocytes. Mere deposition of fat in the liver is termed steatosis, and together these constitute fatty liver changes.

There are two main types of fatty liver disease: alcohol-related fatty liver disease and non-alcoholic fatty liver disease (NAFLD). Risk factors for NAFLD include diabetes, obesity and metabolic syndrome. When inflammation is present it is referred to as alcoholic steatohepatitis and non-alcoholic steatohepatitis (NASH). Untreated steatohepatitis of either may cause progress to fibrosis and subsequent cirrhosis, and NASH is now believed to be a frequent cause of unexplained cirrhosis.

Diabetic nephropathy is a kidney disease that develops as a result of diabetes mellitus (DM). Diabetes mellitus, and Type 2 Diabetes Mellitus (T2DM) is the most common cause of end stage renal disease (ESRD). Diabetic nephropathy generally results in a chronic and progressive degradation of kidney function, to the point where the patient must undergo dialysis or receive a transplant to survive. The initial stage of subtle morphologic changes in the renal glomeruli is followed by microalbuminuria. This is associated with a modestly rising blood pressure and an increased incidence of cardiovascular disease. There follows a continued increase in urinary protein excretion and defining glomerular filtration rate. Diabetic nephropathy has many possible underlying pathophysiological causes including metabolic, glycosylation of proteins, haemodynamics, altered flow/pressure in glomeruli, the development of hypertension and cytokine production; all of these are associated with the development of extracellular matrix and increased vascular permeability leading to glomerular damage and proteinuria.

Huang et al. (Kidney International 2009, 76, 383-394) describe a dipeptide-derivative (NTU281) as an irreversible TG2-Inhibitor. One of the drawbacks of said dipeptide-derivative is that the dipeptide-derivative has to be applied by an implanted osmotic pump locally into the kidney. A systemic formulation of the dipeptide-derivative according to Johnson is not conceivable on the basis of this teaching since TG2 is ubiquitously expressed in almost all cell types and cell compartments, is present on the cell surface and gets secreted to the extracellular matrix, and is present in various organs, so that by applying a TG2-inhibitor unwanted off-target-effects was most likely.

Huang et al. describe an implanted osmotic pump containing a topical formulation NTU281 (drug) in phosphate-buffered saline as a vehicle (50 mmol/l). Thereby, the osmotic pump has to be implanted by a surgical intervention being connected with anaesthesia. Although anaesthesia is commonly used in the medical field, a significant risk for complications is always associated, in particular when vulnerable populations as children and elderly are treated. The implantation of an osmotic pump into the body of a patient cause an additional risk for the patient since electronic devices like pumps are sensitive under physiological conditions and might for example burst, and it is thus not always reliable. Moreover, the pump has to be maintained which causes an additional suffering for the patient. Furthermore, the patient compliance can be improved remarkably since the obstacle of surgical intervention is removed. An implanted osmotic pump containing a topical formulation cannot be used in human.

Lauzier et al. (Arthritis Research Therapy 2012, 14, R159) describe the influence cystamine or a RNA-derivative for the inhibition of TG2 by cystamine, a competitive inhibitor of TGase on the invadopodia formation and cartilage breakdown in arthritis. Cystamine is a disulfide having two amino moieties.

Luciani et al. (Nature Cell Biology 2010, 12, 863-875) describe the influence of cystamine and siRNA on the lung inflammation in cystic fibrosis.

Luo et al. (Journal of the American Heart Association, 2016, 1-12) disclose the influence of 1,3-dimethyl-2-[(2-oxopropyl)-thio]midazolium (R283) or halo-dihydroisoxazole-derivate transglutaminase inhibitor (KCC009) on inflammation in cystic fibrosis.

Olsen et al. (American Journal of Respiratory Cell and Molecular Biology 2014, 50, 737-747) disclose the influence of two different small electrophilic compounds, 2-cyano-3,12-dioxoolean-1,9-dien-28-oic acid and 15-deoxydelta-12,14-prostaglandin J2 on pulmonary fibrosis.

Sanchez-Lara et al. (Veterinary Pathology 2015, Vol. 52(3) 513-523) describe the influence of 1,3-dimethyl-2-(oxopropyl)thio)-imidazolium chloride (D003, Zedira), the nonselective TG inhibitor NTU281, or monoclonal antibody BB7 on chronic kidney disease.

It is still a great problem in the pharmaceutical field to establish an appropriate bioavailability of a drug under physiological conditions in particular in case of a systemic therapy.

It is the objective of the present invention to provide means for the treatment of diabetic nephropathy and/or non-alcoholic steatohepatitis exhibiting a bioavailability, and a high anti-fibrotic effect along with low side-effects.

It is another objective of the present invention to provide a compound for use as a hepatoprotecant, i.e. hepatoprotective agent and use in the protection of the liver against hepatotoxicity, the improvement of liver function, the protection/repair of liver injury, and/or the prophylaxis or treatment of a liver disease.

The objective of the present invention is solved by the teaching of the independent claims. Further advantageous features, aspects and details of the invention are evident from the dependent claims, the description, the figures, and the examples of the present application.

BRIEF DESCRIPTION OF THE INVENTION

The objective of the present invention is solved by a formulation preferably a systemic formulation containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

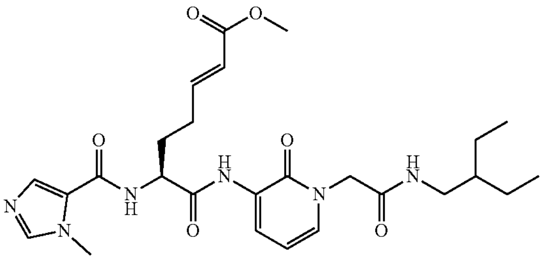

, or an enantiomer, a solvate, a hydrate or a pharmaceutically acceptable salt of formula (I). Herein the compound of the formula (I) is also referred to as Compound 1 or Comp1.

Unexpectedly, it could be found that a compound according to formula (I) can be used to reduce fibrosis in particular fibrosis caused by a diabetic nephropathy and non-alcoholic steatohepatitis. The compound contains a pyridinone moiety as a main structural element. Further, it is surprising that a compound according to formula (I) can be used in the prophylaxis and treatment of nephropathy in particular diabetic nephropathy, liver fibrosis, and cystic fibrosis as a systemic formulation, i.e. the drug is distributed through the blood or lymphatic system throughout the body. This is particularly surprising due to the fact that TG2 is ubiquitously expressed in almost all cell types and cell compartments, is present on the cell surface and gets secreted to the extracellular matrix, and is present in various organs, and thus it could be envisioned that off-target effects would be most likely. The NASH- and mouse model study confirms the anti-fibrotic effect on the liver and kidney being achieved by the administration of a systemic formulation containing the compound according to formula (I) (example 2 and 3). Moreover, positive data of the bioavailability study in mouse (example 4) also confirms the bioavailability of compound (I) by a systemic administration in vivo. Suprisingly, it was found that the bioavailability of compound (I) could be largely increased in human by application of the systemic formulation (example 7).

In addition, a systemic formulation avoids means like an osmotic pump such as used by Johnson et al., and an implantation of said device can be completely avoided, and thus the administration of the drug is objectively facilitated, more reliable, safer, and the suffering for the patient can be significantly and objectively be reduced. The formulation according to the invention can be administered much easier than the formulation of the state of the art. In addition, the formulation according to the invention exhibits a higher anti-fibrotic effect, and thus a better result of the therapy.

Diabetes is also often associated with NASH (non-alcoholic steatohepatitis) which is a frequent cause of unexplained cirrhosis. It is apparent that the treatment of NASH and a diabetic nephropathy is often required at the same time. A systemic formulation according to the invention is usable to target the liver (NASH) and the kidneys (diabetic nephropathy) simultaneously. Likewise, cholestatic liver diseases, such as PSC (primary sclerosing cholangitis) and PBC (primary biliary cholangitis) are fibrotic liver diseases which are often associated with cholemic nephropathy, a chronic and fibrotic inflammation of the kidney caused by high exposure to endogenous bile acids. Also possible is the treatment of the kidneys, and prophylactic treatment of the liver at the same time, and vice versa. Thus, apparently the systemic formulation according to the invention enables its use in a new clinical situation. In addition, cystic fibrosis is often related to diabetes. It could be shown that the a systemic formulation containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate exhibit the same anti-fibrotic effect in the liver and in the kidney (Example 5).

DESCRIPTION OF THE INVENTION

The term "systemic formulation" refers to a pharmaceutical composition suitable for administration such that a drug or active agent is administered systemically throughout the body of an organism, e.g. a form of medication for the circulatory system so that the entire body is affected. Administration can take place via enteral administration (absorption of the drug through the gastrointestinal tract) or parenteral administration (e.g. pulmonary, nasal, injection or infusion). Preferably, the term "systemic formulation" excludes formulation for an intravenous application. The circulatory system, also called the cardiovascular system or the vascular system, is an organ system that permits blood to circulate and transport nutrients (such as amino acids and electrolytes), oxygen, carbon dioxide, hormones, and blood cells to and from the cells in the body to provide nourishment and help in fighting diseases, stabilize temperature and pH, and maintain homeostasis.

The circulatory system includes the lymphatic system, which circulates lymph. The passage of lymph for example takes much longer than that of blood. Thus, the term "systemic formulation" refers to a formulation, wherein the drug is distributed throughout the body of an organism by e.g. the blood or lymphatic system throughout the body, for example, after an intravenous or intramuscular injection or taking a tablet, i.e. after an enteral, in particular an oral or a parenteral administration.

The systemic formulations as disclosed herein are preferably in the form of a tablet, coated tablet, capsule, powder, or granules.

In contrast thereto, a "topical formulation" is a formulation that is applied to a particular place on or in the body where it should act. Topical means "place", "locally", at a "specific site", "externally" or limited to a "specific site of the body". Thus, the risk of possible unwanted side effects in other areas of the organism can be reduced. Most often topical administration means application to body surfaces such as the skin or mucous membranes to treat ailments via a large range of classes including creams, foams, gels, lotions, and ointments. Many topical medications are epicutaneous, meaning that they are applied directly to the skin. Topical medications may also be inhalational, such as asthma medications, or applied to the surface of tissues other than the skin, such as eye drops applied to the conjunctiva, or ear drops placed in the ear, medications applied to the surface of a tooth or application of the drug by means of a pump such as an osmotic pump.

The topical formulations include aural, buccal, endobronchial, epicutaneous, inhalation, intraarticular, into the gluteus maximus muscle, intracardiac, intracutaneous, intralumbar, intralymphatic, intramammarial, intranasal, intraneuronal, intraocular, intraorbital, intraosseous, intrapericadial, intrapulmonary, intrathecal, intratracheal, intraurethral, intrauterine, intraventricular, intravesical, intravitreal, conjunctival, cutan, nasal, perineural, retrobulbar, subconjunctival, vaginal, and ciliary.

The term “parenteral formulation”, as used herein refers, to a formulation, which usually is administered by injection or infusion, and includes, without limitation, epidural, intraarterial, intravenous, intravasal, intravascular, intramuscular, intraperitoneal, intrapleural, subcutaneous, subcuticular, and transdermal injection and infusion. Preferably, a parenteral formulation is selected from the group comprising or consisting of epidural, intravasal, intravascular, intramuscular, intraperitoneal, intrapleural, subcutaneous, subcuticular, and transdermal injection and infusion. Preferably, the intraarterial and intravenous formulations are excluded from the parenteral formulations.

“Enteral formulation”, as used herein, refers to a formulation being usually a medication which is absorbed through the mouth (per os, orally, perorally): tablets, dragees, capsules, juices, drops, etc. These medicines are absorbed into the blood in the gastrointestinal tract, and then enter the liver via the portal vein system and then into the bloodstream via the hepatic vein. The term, as used herein, refers to a formulation which is usually administered including, without limitation enteral, intragastral, sublingual, peroral (oral), and rectal. Preferably, enteral formulation consists of a formulation selected from the group comprising or consisting of enteral, intragastral, sublingual, peroral (oral), and rectal.

“Oral formulation”, as used herein, refers to a formulation being a medication which is absorbed through the mouth (per os, orally, perorally tablets, dragees, capsules, juices, drops, etc.). These medicines are absorbed into the blood in the gastrointestinal tract, and then enter the liver via the portal vein system and then into the bloodstream via the hepatic vein. The term, as used herein, refers to a formulation which is administered orally.

The systemic formulation can be in a liquid or solid form including solutions, oral drops, suspensions, emulsions, powders and granules such as effervescent granules, tablets such as uncoated tablets, coated tablets, effervescent tablets, soluble tablets, chewable tablets, oral lyophilisates, lozenges, pastilles, compressed lozenges, sublingual tablets, buccal tablets, granules, effervescent granules and capsules. In particular, the systemic formulation can be a liquid preparation including oral solutions, suspensions, emulsions, powders and granules for oral solutions and suspensions, oral drops, powder for oral drops, syrups and powder and granules for syrups or in a solid form including uncoated tablets, coated tablets, effervescent tablets, soluble tablets, chewable tablets, oral lyophilisates, lozenges, pastilles, compressed lozenges, sublingual tablets, buccal tablets, granules, effervescent granules and capsules. Uncoated and coated tablets, and capsules, either hard or soft are the preferred pharmaceutical formulations. Most preferably, the formulation is a tablet or a capsule. As an example, there may be mentioned water or water/propylene glycol solutions for parenteral injections or addition of sweeteners and opacifiers for oral solutions, suspensions, and emulsions. Preferably, the systemic formulation is a solid formulation, more preferably a solid enteral formulation, and most preferably a solid oral formulation.

“Topical administration”, as used herein, refers to the administration of a topical formulation.

“Systemic administration”, as used herein, refers to the administration of a systemic formulation.

“Topical availability”, as used herein, refers to the release of the drug from its formulation such as from a vehicle of a formulation or from a tablet to the place at which the drug should be absorbed by the specific tissue or organ so that the drug could act at all.

“Systemic availability”, as used herein, refers to the proportion of the dose of a drug that reaches the systemic circulation intact after administration by a route other than intravenous. The term “systemic availability” also refers to the extent to which a drug or other substance is taken up by a specific tissue or organ after administration. For example, a drug which is orally administered and overcomes the epithelium barrier of the intestine is in the tissue of the intestine, and thus it has a systemic availability or in the other words it is systemic available. “Systemic availability” and “systemic available” are synonymous for “bioavailability” or “bioavailable”. Thus, also topically administered compounds can exhibit a systemic availability.

The term “drug level” refers to the level of the drug in the plasma, tissue or organ, and the phrase “systemic availability at the target site” refers to the same aspect.

As used herein, the term “pharmaceutically acceptable salts” refers to salts of certain ingredient(s) which possess the same activity as the unmodified compound(s) and which are neither biologically nor otherwise undesirable.

A pharmaceutically acceptable salt can be formed with, for example, organic or inorganic acids. Suitable acids include acetic acid, acetylsalicylic acid, organic di-carboxylic acid such as oxalic acid, malonic acid, succinic acid, glutaric acid, tartaric acid, fumaric acid, maleic acid, malic acid, adipic acid, or glutamic acid, and organic tri-carboxylic acid such as citric acid, or sodium hydrogen citrate alginic acid, ascorbic acid, aspartic acid, benzoic acid, benzenesulfonic acid, bisulfic acid, boric acid, butyric acid, camphoric acid, camphorsulfonic acid, carbonic acid, citric acid, cyclopentanepropionic acid, digluconic acid, dodecylsulfic acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylanesulfonic acid, naphthylic acid, nicotinic acid, nitrous acid, oxalic acid, pelargonic, phosphoric acid, propionic acid, saccharin, salicylic acid, sorbic acid, succinic acid, sulfuric acid, tartaric acid, thiocyanic acid, thioglycolic acid, thiosulfuric acid, tosylic acid, undecylenic acid, and naturally and synthetically derived amino acids. Preferably, the acid is adipic acid.

Thus, a preferred embodiment of the present invention is directed to the salt of (S,E)-methyl-7-(1-(2-(2-ethylbutylamino)-2-oxoethyl)-2-oxo-1,2-dihydro-pyridin-3- ylamino)-6-(1-methyl-1H-imidazole-5-carboxamido)-7-oxohept-2-enoate of the formula (I):

(I)

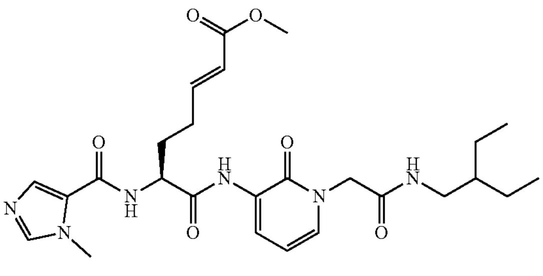

, and adipic acid.

Another preferred embodiment of the invention is related to a systemic formulation containing a salt of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

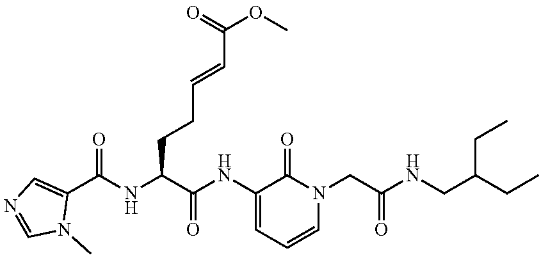

, and adipic acid, or an enantiomer, a solvate or a hydrate of the salt of formula (I) and adipic acid.

As used herein, the term "solvates" refers to those forms of a compound in particular the (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate which form a complex through coordination with solvent molecules.

As used herein, the term "hydrates" refers to those forms of a compound in particular the (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate which form a complex through coordination with water molecules.

As used herein, the term "effective amount" or "therapeutically effective amount" of an active agent or a pharmaceutically active agent or a drug or an active pharmaceutical ingredient, which are synonymous herein, refers to an amount of the active agent or pharmaceutically active agent or drug or active pharmaceutical ingredient, sufficient enough to have a positive effect. Accordingly, these amounts are disease to be treated but low enough to avoid serious side effects. A therapeutically effective amount of the pharmaceutically active agent will cause a substantial relief of symptoms when applied repeatedly over time. Effective amounts of the pharmaceutically active agent will vary with the particular condition or conditions being treated, the severity of the condition, the duration of the treatment, the specific components of the composition being used, and like factors.

As used herein, the term "active agent", "pharmaceutically active agent", "drug" or "active pharmaceutical ingredient", which are synonymously used herein, refers to a compound exhibiting a therapeutic effect upon a mammal in particular a human.

As used herein, the term "pharmaceutical composition" refers to a composition which, upon administration, demonstrates a therapeutic effect upon a mammal.

Systemic formulations according to the invention as described herein, preferably contains (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

An embodiment of the present invention is thus direct to a systemic formulation containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

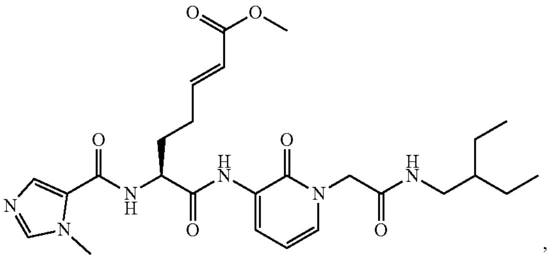

,

Further, the systemic formulation can be an enteral or parenteral formulation. An embodiment according to the invention is therefore related to a systemic formulation containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, wherein the systemic formulation is in form of an enteral or parenteral formulation.

It is preferred if the systemic formulation is in form of an oral formulation. An oral formulation is a specific form of an enteral formulation. Therefore, a preferred embodiment of the invention is directed to a systemic formulation containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, wherein the systemic formulation is in form of an oral formulation.

Furthermore, (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate can be administered in form of its pharmaceutically active salts, solvate or hydrate, optionally using essentially non-toxic pharmaceutically acceptable excipients. Formulations are prepared in a known manner in a conventional solid or fluid carrier using conventional pharmaceutically acceptable excipients in a suitable dose.

Thus, the systemic formulation according to the invention can further comprise an excipient. An embodiment according to the invention is thus directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamindo)-7- oxohept-2-enoate or an enantiomer, a solvate, a hydrate or a pharmaceutically acceptable salt thereof, and at least one excipient.

After the administration of the systemic formulation, the administered drug dose has to dissolve quickly and completely. The pH variations in the stomach after the oral administration have to be regulated and it should be ensured that the administered drug dose is dissolved. The bigger the systemic availability (AUC) in conjunction with the mucosal release in the small intestine, the higher pharmacological effect to be expected.

The excipient can be an acidifier. The term "acidifier" refers to a substance which, when dissolved in water, produces a pH level of less than 7.0. Thus, systemic formulations according to the invention can comprise an acidifier. Acidifiers include organic acids such as ascorbic acid, organic di-carboxylic acid such as oxalic acid, malonic acid, succinic acid, glutaric acid, tartaric acid, fumaric acid, maleic acid, malic acid, adipic acid (hexanedioic acid), or glutamic acid, and organic tri-carboxylic acid such as citric acid, or sodium hydrogen citrate. Preferably, the acidifier is adipic acid.

Preferred "acidifiers" for the systemic formulations as disclosed herein are selected from the group consisting of ascorbic acid, organic di-carboxylic acids such as oxalic acid, malonic acid, succinic acid, glutaric acid, tartaric acid, fumaric acid, maleic acid, malic acid, adipic acid, glutamic acid, and organic tri-carboxylic acids, citric acid, and sodium hydrogen citrate.

More preferred "acidifiers" for the systemic formulations as disclosed herein are selected from the group consisting of adipic acid, fumaric acid, glutaric acid.

Thus, the systemic formulation according to the invention can comprise an acidifier.

A preferred embodiment according to the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is an acidifier.

Another preferred embodiment according to the invention is related to a systemic formulation containing or consisting of (S,E)-methyl-7-(1-(2-(2-ethylbutylamino)oxoethyl)-2-oxo-1,2-dihydro-pyridin-3-ylamino)-6-(1-methyl-1H-imidazole carboxamido)-7-oxohept-2-enoate or an enantiomer, a solvate, a hydrate or a pharmaceutically acceptable salt thereof, and at least one acidifier.

A preferred embodiment according to the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is an acidifier, and wherein at least one acidifier is selected from the group comprising or consisting of organic di-carboxylic acid and organic tri-carboxylic acid. Preferably, at least one acidifier is selected from the group consisting of organic di-carboxylic acid and organic tri-carboxylic acid. More preferably, the at least one acidifier is selected from the group the group comprising or consisting of organic di-carboxylic acid and organic tri-carboxylic acid. Even more preferably, the at least one acidifier is selected from the group the group consisting of organic di-carboxylic acid and organic tri-carboxylic acid.

Thus, a preferred embodiment according to the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one acidifier, wherein at least one acidifier is selected from the group comprising or consisting of organic di-carboxylic acid and organic tri-carboxylic acid.

A preferred embodiment according to the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is an acidifier, and wherein at least one acidifier is selected from the group comprising or consisting of oxalic acid, malonic acid, succinic acid, glutaric acid, tartaric acid, fumaric acid, maleic acid, malic acid, adipic acid (hexanedioic acid), or glutamic acid. Preferably, at least one acidifier is selected from the group consisting of oxalic acid, malonic acid, succinic acid, glutaric acid, tartaric acid, fumaric acid, maleic acid, malic acid, adipic acid (hexanedioic acid), or glutamic acid. More preferably, the at least one acidifier is selected from the group comprising or consisting of oxalic acid, malonic acid, succinic acid, glutaric acid, tartaric acid, fumaric acid, maleic acid, malic acid, adipic acid (hexanedioic acid), or glutamic acid. Even more preferably, the at least one acidifier is selected from the group consisting of oxalic acid, malonic acid, succinic acid, glutaric acid, tartaric acid, fumaric acid, maleic acid, malic acid, adipic acid (hexanedioic acid), or glutamic acid.

A preferred embodiment according to the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one acidifier, wherein at least one acidifier is selected from the group comprising or consisting of oxalic acid, malonic acid, succinic acid, glutaric acid, tartaric acid, fumaric acid, maleic acid, malic acid, adipic acid (hexanedioic acid), or glutamic acid.

A more preferred embodiment according to the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, and at least one excipient or an enantiomer, a solvate, a hydrate or a pharmaceutically acceptable salt thereof, wherein at least one excipient is an acidifier, wherein the acidifier is adipic acid, fumaric acid, glutaric acid.

A particularly preferred embodiment according to the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, and at least one excipient or an enantiomer, a solvate, a hydrate or a pharmaceutically acceptable salt thereof, wherein at least one excipient is an acidifier, wherein the acidifier is adipic acid.

A particularly preferred embodiment according to the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one acidifier, wherein at least one acidifier is adipic acid.

A particularly preferred embodiment according to the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and adipic acid.

The drug solution is transported to the small intestine after the stomach passage. This passage is—at least in the fasted state—connected with an increase of the pH from about 2 to about 6. The drug dose has to remain in the solution, i.e. the drug should not precipitate. This effect can be achieved by the addition of a polymeric precipitation inhibitor. Thus, the polymeric precipitation inhibitor inhibits the crystallization of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and functions as a crystallization inhibitor.

Polymeric precipitation inhibitors are polymers capable to stabilize the supersaturation stage of the drug, i.e. they are able to prevent nucleation of the drug molecules or the growing of the initially formed drug particles, which is achieved by covering the surface of the drug particles, thereby preventing particle-particle interaction, or by enhancing the viscosity of the suspension medium. The ability of precipitation inhibitors to kinetically stabilize the supersaturated state of the drug is thought to result from intermolecular interactions between the drug and polymer in solution (e.g. via hydrogen bonding or hydrophobic interactions), the ability of the polymer to sterically hinder the crystallization process or from increasing the viscosity of the suspension medium, and not by enhancing the solubility of the drug, i.e. by increasing the equilibrium solubility.

The saturation solubility of said compound is low at a pH value in the small intestine (example 10 and FIG. 11). The solution is stabilized by the addition of polymeric precipitation inhibitor which can also act as a binder. When the drug is exposed to an aqueous medium, the polymeric precipitation inhibitor decelerates the precipitation or crystallization of the drug preferably by complexation. Apart from that, the polymeric precipitation inhibitor increases the viscosity in the medium which further intensifies the effect.

Thus, the systemic formulation according to the invention can further comprise a polymeric precipitation inhibitor. Thus, the excipient can be a polymeric precipitation inhibitor.

The term "polymeric precipitation inhibitor" refers to a material that decelerates the precipitation or crystallization of a drug.

"polymeric precipitation inhibitor" includes cellulose derivatives, starch derivatives, dextran/dextrin derivatives, polyether derivatives, polyvinyl derivatives, polyacrylic acid derivatives and poly amine derivatives, polysulfonic acid derivatives and a combination thereof.

In some embodiments "polymeric precipitation inhibitor" is selected from the group comprising or consisting of:

cellulose derivatives including but not limited to microcrystalline cellulose (MCC), cellulose acetate phthalate (CAP), cellulose acetate terephthalate, cellulose acetate isophthalate, cellulose acetate butyrate (CAB), cellulose acetate trimellitate (CAT), methylcellulose (MC), methylcellulose acetate phthalate, ethylcellulose (EC), carboxymethyl cellulose (CMC), sodium carboxymethyl cellulose, carboxymethylethylcellulose (CMEC), hydroxymethylcellulose (HMC), hydroxyethylcellulose (HEC), hydroxypropyl cellulose (HPC or hyprolose), L-hydroxypropyl cellulose, hydroxypropylmethylcellulose (HPMC or hypromellose), carboxymethyl hydroxyethyl cellulose (CMHEC), sodium carboxymethyl hydroxyethyl cellulose (NaCMHEC), hydroxypropyl methylcellulose phthalate (HPMCP, hypromellose phtahalate), hydroxypropyl methylcellulose acetate succinate (HPMCAS, hypromellose acetate succinate);

starch derivatives including but not limited to hydroxyethyl starch, hydroxypropyl starch (HPS) and pregelatinized starch;

dextran/dextrin derivatives including but not limited to cyclodextran (i.e., cycloisomalto-heptaose (CI-7), cycloisomalto-octaose (CI-8), cycloisomalto-nonaose (CI-9)), hydroxypropyl dextran, maltodextrin, α-/β-/γ-cyclodextrin, 2-hydroxyethyl-β-cyclodextrin, 2-hydroxypropyl-β-cyclodextrin (HPβCD), sulfobuthylether-β-cyclodextrin sodium salt, methylated-β-cyclodextrin, 2-hydroxypropyl-γ-cyclodextrin;

polyether derivatives including but not limited to polyethylene glycol (PEG), polyethylene oxide (PEO), polyether polyol, poly(propylene glycol) bis(2-aminopropyl ether) (PPGAE), poly(ethylene oxide)-poly (propylene oxide)-poly (ethylene oxide) (PEO-PPO-PEO, poloxamer) such as poloxamer 188 and poloxamer 407, polyvinyl derivatives including but not limited to polyvinyl alcohol (PVA), polyvinyl acetate phthalate (PVAP), polyvinylpyrrolidone (PVP), polyvinylpyrrolidone-co-polyvinyl acetate (PVPVA), polyvinyl caprolactam-polyvinyl acetate-polyethylene glycol graft copolymer (Soluplus®) polyacrylic acid derivatives including but not limited to poly(acrylic acid) (PAA), poly(acrylamide/acrylic acid) (PAC-AC), polymethylacrylate (PMA), polymethacrylic acid, poly (methacrylic acid/methyl methacrylate), poly(methacrylic acid/ethyl acrylate);

polyamine derivatives including but not limited to polyethylene imine (PEI), polyallylamine hydrogen chloride, polydiallydimethyl ammonium chloride, and poly (2-ethyl-2-oxazoline);

polysulfonic acid derivatives including but not limited to polystyrensulfonic acid (PSSA); and a combination of at least two of the above-mentioned polymeric precipitation inhibitors.

Preferably, the "polymeric precipitation inhibitor" is selected from the group comprising or consisting of: microcrystalline cellulose (MCC), cellulose acetate phthalate (CAP), cellulose acetate terephthalate, cellulose acetate isophthalate, cellulose acetate butyrate (CAB), cellulose acetate trimellitate (CAT), methylcellulose (MC), methylcellulose acetate phthalate, ethylcellulose (EC), carboxymethyl cellulose (CMC), sodium carboxymethyl cellulose, carboxymethylethylcellulose (CMEC), hydroxymethylcellulose (HMC), hydroxyethylcellulose (HEC), hydroxypropyl cellulose (HPC or hyprolose), L-hydroxypropyl cellulose, hydroxypropylmethylcellulose (HPMC or hypromellose), carboxymethyl hydroxyethyl cellulose (CMHEC), sodium carboxymethyl hydroxyethyl cellulose (NaCMHEC), hydroxypropyl methylcellulose phthalate (HPMCP, hypromellose phtahalate), hydroxypropyl methylcellulose acetate succinate (HPMCAS, hypromellose acetate succinate), hydroxyethyl starch, hydroxypropyl starch (HPS) and pregelatinized starch, cyclodextran (i.e., cycloisomalto-heptaose (CI-7), cycloisomalto-octaose (CI-8), cycloisomalto-nonaose (CI-9)), hydroxypropyl dextran, maltodextrin, α-/β-/γ-cyclodextrin, 2-hydroxyethyl-β-cyclodextrin, 2-hydroxypropyl-β-cyclodextrin (HPβCD), sulfobuthylether-β-cyclodextrin sodium salt, methylated-β-cyclodextrin, 2-hydroxypropyl-γ-cyclodextrin, polyethylene glycol (PEG), polyethylene oxide (PEO), polyether polyol, poly(propylene glycol) bis(2-aminopropyl ether) (PPGAE), poly(ethylene oxide)-poly (propylene oxide)-poly (ethylene oxide) (PEO-PPO-PEO, poloxamer) such as poloxamer 188 and poloxamer 407, polyvinyl alcohol (PVA), polyvinyl acetate phthalate (PVAP), polyvinylpyrrolidone (PVP), polyvinylpyrrolidone-co-polyvinyl acetate (PVPVA), polyvinyl caprolactam-polyvinyl acetate-polyethylene glycol graft copolymer (Soluplus®), poly(acrylic acid) (PAA), poly (acrylamide/acrylic acid) (PAC-AC), polymethylacrylate (PMA), polymethacrylic acid, poly(methacrylic acid/methyl methacrylate), poly(methacrylic acid/ethyl acrylate), polyethylene imine (PEI), polyallylamine hydrogen chloride, polydiallydimethyl ammonium chloride, poly(2-ethyl-2-oxazoline), polystyrensulfonic acid (PSSA); and a combination of at least two of the above-mentioned polymeric precipitation inhibitors.

More preferably, the"polymeric precipitation inhibitor" is selected from the group comprising or consisting of: microcrystalline cellulose (MCC), cellulose acetate phthalate (CAP), cellulose acetate terephthalate, cellulose acetate isophthalate, cellulose acetate butyrate (CAB), cellulose acetate trimellitate (CAT), methylcellulose (MC), methylcellulose acetate phthalate, ethylcellulose (EC), carboxymethyl cellulose (CMC), sodium carboxymethyl cellulose, carboxymethylethylcellulose (CMEC), hydroxymethylcellulose (HMC), hydroxyethylcellulose (HEC), hydroxypropyl cellulose (HPC or hyprolose), L-hydroxypropyl cellulose, hydroxypropylmethylcellulose (HPMC or hypromellose), carboxymethyl hydroxyethyl cellulose (CMHEC), sodium carboxymethyl hydroxyethyl cellulose (NaCMHEC), hydroxypropyl methylcellulose phthalate (HPMCP, hypromellose phtahalate), hydroxypropyl methylcellulose acetate succinate (HPMCAS, hypromellose acetate succinate), polyethylene glycol (PEG), polyethylene oxide (PEO), polyether polyol, poly(propylene glycol) bis (2-aminopropyl ether) (PPGAE), poly(ethylene oxide)-poly (propylene oxide)-poly (ethylene oxide) (PEO-PPO-PEO, poloxamer) such as poloxamer 188 and poloxamer 407, polyvinyl alcohol (PVA), polyvinyl acetate phthalate (PVAP), polyvinylpyrrolidone (PVP), polyvinylpyrrolidone-co-polyvinyl acetate (PVPVA), polyvinyl caprolactam-polyvinyl acetate-polyethylene glycol graft copolymer (Soluplus®), poly(acrylic acid) (PAA), poly (acrylamide/acrylic acid) (PAC-AC), polymethylacrylate (PMA), polymethacrylic acid, poly(methacrylic acid/methyl methacrylate), poly(methacrylic acid/ethyl acrylate), and a combination of at least two of the above-mentioned polymeric precipitation inhibitors.

More preferably, suitable polymeric precipitation inhibitor includes L-hydroxypropyl cellulose, hydroxypropyl cellulose, a combination of L-hydroxypropyl cellulose and hydroxypropyl cellulose, polyethylene glycol (PEG), poly (ethylene oxide)-poly (propylene oxide)-poly (ethylene oxide) (=poloxamer), polyvinyl alcohol (PVA), polyvinylpyrrolidone (PVP), carboxymethyl cellulose (CMC), methylcellulose (MC), hydroxyethylcellulose (HEC), hydroxypropylmethylcellulose (HPMC), ethylcellulose (EC), polyvinyl caprolactam-polyvinyl acetate-polyethylene glycol graft copolymer (Soluplus®) and/or sodium carboxymethyl cellulose. Still more preferably, the polymeric precipitation inhibitor is selected from the group comprising or consisting of polyvinyl alcohol (PVA), polyvinyl caprolactam-polyvinyl acetate-polyethylene glycol graft copolymer (Soluplus®), cellulose and cellulose derivative. More preferably, the polymeric precipitation inhibitor is polyvinyl alcohol (PVA), polyvinyl caprolactam-polyvinyl acetate-polyethylene glycol graft copolymer (Soluplus®), a cellulose, a cellulose derivative, or a combination of a cellulose and a cellulose derivative.

Preferably, the cellulose is microcrystalline cellulose (MCC) and the cellulose derivative is selected from the group consisting of microcrystalline cellulose (MCC), cellulose acetate phthalate (CAP), cellulose acetate terephthalate, cellulose acetate isophthalate, cellulose acetate butyrate (CAB), cellulose acetate trimellitate (CAT), methylcellulose (MC), methylcellulose acetate phthalate, ethylcellulose (EC), carboxymethyl cellulose (CMC), sodium carboxymethyl cellulose, carboxymethylethylcellulose (CMEC), hydroxymethylcellulose (HMC), hydroxyethylcellulose (HEC), hydroxypropyl cellulose (HPC or hyprolose), L-hydroxypropyl cellulose, hydroxypropylmethylcellulose (HPMC or hypromellose), carboxymethyl hydroxyethyl cellulose (CMHEC), sodium carboxymethyl hydroxyethyl cellulose (NaCMHEC), hydroxypropyl methylcellulose phthalate (HPMCP, hypromellose phtahalate), hydroxypropyl methylcellulose acetate succinate (HPMCAS, hypromellose acetate succinate).

Even more preferably, the polymeric precipitation inhibitor is selected from the group comprising or consisting of polyvinyl alcohol (PVA), polyvinyl caprolactam-polyvinyl acetate-polyethylene glycol graft copolymer (Soluplus®), L-hydroxypropyl cellulose and hydroxypropyl cellulose. Most preferably, the polymeric precipitation inhibitor is polyvinyl alcohol (PVA), polyvinyl caprolactam-polyvinyl acetate-polyethylene glycol graft copolymer (Soluplus®), L-hydroxypropyl cellulose, hydroxypropyl cellulose, or a combination of L-hydroxypropyl cellulose and hydroxypropyl cellulose. The combination of L-hydroxypropyl cellulose and hydroxypropyl cellulose acts as polymeric precipitation inhibitor and disintegrant so that the amount of the disintegrant can be reduced.

The systemic formulations as disclosed herein and especially the systemic formulations for oral administration contain as polymeric precipitation inhibitor most preferably polyvinyl alcohol (PVA), polyvinyl caprolactam-polyvinyl acetate-polyethylene glycol graft copolymer (Soluplus®), L-hydroxypropyl cellulose, hydroxypropyl cellulose or a combination of L-hydroxypropyl cellulose and hydroxypropyl cellulose.

The systemic formulations as disclosed herein and especially the systemic formulations for oral administration comprise most preferably at least one acidifier and/or at least one polymeric precipitation inhibitor.

The systemic formulations as disclosed herein and especially the systemic formulations for oral administration contain most preferably adipic acid as acidifier and L-hydroxypropyl cellulose, hydroxypropyl cellulose, polyvinyl alcohol (PVA), polyvinyl caprolactam-polyvinyl acetate-polyethylene glycol graft copolymer (Soluplus®) or a combination of L-hydroxypropyl cellulose and hydroxypropyl cellulose as polymeric precipitation inhibitor.

An embodiment of the invention is thus related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a polymeric precipitation inhibitor.

An embodiment of the invention is thus related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one polymeric precipitation inhibitor.

Preferably the "polymeric precipitation inhibitor" is selected from the group comprising or consisting of:

cellulose derivatives including but not limited to microcrystalline cellulose (MCC), cellulose acetate phthalate (CAP), cellulose acetate terephthalate, cellulose acetate isophthalate, cellulose acetate butyrate (CAB), cellulose acetate trimellitate (CAT), methylcellulose (MC), methylcellulose acetate phthalate, ethylcellulose (EC), carboxymethyl cellulose (CMC), sodium carboxymethyl cellulose, carboxymethylethylcellulose (CMEC), hydroxymethylcellulose (HMC), hydroxyethylcellulose (HEC), hydroxypropyl cellulose (HPC or hyprolose), L-hydroxypropyl cellulose, hydroxypropylmethylcellulose (HPMC or hypromellose), carboxymethyl hydroxyethyl cellulose (CMHEC), sodium carboxymethyl hydroxyethyl cellulose (NaCMHEC), hydroxypropyl methylcellulose phthalate (HPMCP, hypromellose phtahalate), hydroxypropyl methylcellulose acetate succinate (HPMCAS, hypromellose acetate succinate);

starch derivatives including but not limited to hydroxyethyl starch, hydroxypropyl starch (HPS) and pregelatinized starch;

dextran/dextrin derivatives including but not limited to cyclodextran (i.e., cycloisomalto-heptaose (CI-7), cycloisomalto-octaose (CI-8), cycloisomalto-nonaose (CI-9)), hydroxypropyl dextran, maltodextrin, α-/β-/γ-cyclodextrin, 2-hydroxyethyl-β-cyclodextrin, 2-hydroxypropyl-β-cyclodextrin (HPβCD), sulfobuthylether-β-cyclodextrin sodium salt, methylated-β-cyclodextrin, 2-hydroxypropyl-γ-cyclodextrin;

polyether derivatives including but not limited to polyethylene glycol (PEG), polyethylene oxide (PEO), polyether polyol, poly(propylene glycol) bis(2-aminopropyl ether) (PPGAE), poly(ethylene oxide)-poly (propylene oxide)-poly (ethylene oxide) (PEO-PPO-PEO, poloxamer) such as poloxamer 188 and poloxamer 407, polyvinyl derivatives including but not limited to polyvinyl alcohol (PVA), polyvinyl acetate phthalate (PVAP), polyvinylpyrrolidone (PVP), polyvinylpyrrolidone-co-polyvinyl acetate (PVPVA), polyvinyl caprolactam-polyvinyl acetate-polyethylene glycol graft copolymer (Soluplus®), polyacrylic acid derivatives including but not limited to poly(acrylic acid) (PAA), poly(acrylamide/acrylic acid) (PAC-AC), polymethylacrylate (PMA), polymethacrylic acid, poly(methacrylic acid/methyl methacrylate), poly(methacrylic acid/ethyl acrylate);

polyamine derivatives including but not limited to polyethylene imine (PEI), polyallylamine hydrogen chloride, polydiallydimethyl ammonium chloride, and poly (2-ethyl-2-oxazoline);

polysulfonic acid derivatives including but not limited to polystyrensulfonic acid (PSSA); and a combination of at least two of the above-mentioned polymeric precipitation inhibitors.

More preferably, the "polymeric precipitation inhibitor" is selected from the group comprising or consisting of: microcrystalline cellulose (MCC), cellulose acetate phthalate (CAP), cellulose acetate terephthalate, cellulose acetate isophthalate, cellulose acetate butyrate (CAB), cellulose acetate trimellitate (CAT), methylcellulose (MC), methylcellulose acetate phthalate, ethylcellulose (EC), carboxymethyl cellulose (CMC), sodium carboxymethyl cellulose, carboxymethylethylcellulose (CMEC), hydroxymethylcellulose (HMC), hydroxyethylcellulose (HEC), hydroxypropyl cellulose (HPC or hyprolose), L-hydroxypropyl cellulose, hydroxypropylmethylcellulose (HPMC or hypromellose), carboxymethyl hydroxyethyl cellulose (CMHEC), sodium carboxymethyl hydroxyethyl cellulose (NaCMHEC), hydroxypropyl methylcellulose phthalate (HPMCP, hypromellose phtahalate), hydroxypropyl methylcellulose acetate succinate (HPMCAS, hypromellose acetate succinate), polyethylene glycol (PEG), polyethylene oxide (PEO), polyether polyol, poly(propylene glycol) bis (2-aminopropyl ether) (PPGAE), poly(ethylene oxide)-poly (propylene oxide)-poly (ethylene oxide) (PEO-PPO-PEO, poloxamer) such as poloxamer 188 and poloxamer 407, polyvinyl alcohol (PVA), polyvinyl acetate phthalate (PVAP), polyvinylpyrrolidone (PVP), polyvinylpyrrolidone-co-polyvinyl acetate (PVPVA), polyvinyl caprolactam-polyvinyl acetate-polyethylene glycol graft copolymer (Soluplus®), poly(acrylic acid) (PAA), poly (acrylamide/acrylic acid) (PAC-AC), polymethylacrylate (PMA), polymethacrylic acid, poly(methacrylic acid/methyl methacrylate), poly(methacrylic acid/ethyl acrylate), and a combination of at least two of the above-mentioned polymeric precipitation inhibitors.

A preferred embodiment of the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is polymeric precipitation inhibitor, and wherein the polymeric precipitation inhibitor is selected from the group comprising or consisting of polyvinyl alcohol (PVA), polyvinyl caprolactam-polyvinyl acetate-polyethylene glycol graft copolymer (Soluplus®), cellulose and cellulose derivative.

A preferred embodiment of the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido) oxohept-2-enoate or an enantiomer, a solvate, a hydrate or a pharmaceutically acceptable salt thereof, and at least one polymeric precipitation inhibitor selected from the group comprising or consisting of polyvinyl alcohol (PVA), polyvinyl caprolactam-polyvinyl acetate-polyethylene glycol graft copolymer (Soluplus®), cellulose and cellulose derivative.

Preferably, the cellulose is microcrystalline cellulose (MCC) and the cellulose derivative is selected from the group consisting of microcrystalline cellulose (MCC), cellulose acetate phthalate (CAP), cellulose acetate terephthalate, cellulose acetate isophthalate, cellulose acetate butyrate (CAB), cellulose acetate trimellitate (CAT), methylcellulose (MC), methylcellulose acetate phthalate, ethylcellulose (EC), carboxymethyl cellulose (CMC), sodium carboxymethyl cellulose, carboxymethylethylcellulose (CMEC), hydroxymethylcellulose (HMC), hydroxyethylcellulose (HEC), hydroxypropyl cellulose (HPC or hyprolose), L-hydroxypropyl cellulose, hydroxypropylmethylcellulose (HPMC or hypromellose), carboxymethyl hydroxyethyl cellulose (CMHEC), sodium carboxymethyl hydroxyethyl cellulose (NaCMHEC), hydroxypropyl methylcellulose phthalate (HPMCP, hypromellose phtahalate), hydroxypropyl methylcellulose acetate succinate (HPMCAS, hypromellose acetate succinate).

An embodiment of the invention is thus related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a polymeric precipitation inhibitor, and wherein the polymeric precipitation inhibitor is polyvinyl alcohol (PVA), polyvinyl caprolactam-polyvinyl acetate-polyethylene glycol graft copolymer (Soluplus®), L-hydroxypropyl cellulose and/or hydroxypropyl cellulose.

An embodiment of the invention is thus related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one polymeric precipitation inhibitor selected from the group comprising or consisting of polyvinyl alcohol (PVA), polyvinyl caprolactam-polyvinyl acetate-polyethylene glycol graft copolymer (Soluplus®), L-hydroxypropyl cellulose and/or hydroxypropyl cellulose.

An embodiment of the invention is thus related to a systemic formulation containing or consisting of (S,E)-methyl-7-(1-(2-(2-ethylbutylamino)-2-oxoethyl)oxo-1,2-dihydro-pyridin-3-ylamino)-6-(1-methyl-1H-imidazole-5-carboxamido)oxohept-2-enoate or an enantiomer, a solvate, a hydrate or a pharmaceutically acceptable salt thereof, and polyvinyl alcohol (PVA), polyvinyl caprolactam-polyvinyl acetate-polyethylene glycol graft copolymer (Soluplus®), L-hydroxypropyl cellulose and/or hydroxypropyl cellulose.

The systemic formulation according to the invention can comprise a binder. Thus, the excipient can be a binder. Binders are characterized as substances binding or "gluing" powders to each other and they consequently serve as "glue" in the formulation. In other words, a binder is a material that holds or draws other materials together to form a cohesive whole mechanically, chemically, by adhesion or cohesion. Suitable binders include sugar, such as sucrose; polysaccharides such as xanthan gum, guar gum, carrageenan, starches derived from wheat, corn, rice and potatoes, and preagglutinated (modified) starch derived from wheat, corn, rice and potatoes, sodium starch glycolate; natural gums such as acacia gum, gelatin and tragacanth; derivatives of sea weed such as alginic acid, sodium alginate and ammonium calcium alginate, cellulose or derivatives thereof such as hydroxypropyl cellulose, L-hydroxypropyl cellulose, low-substituted hydroxypropyl cellulose, methyl cellulose, sodium carboxymethylcellulose, hydroxypropyl methylcellulose, and polyvinylpyrrolidone (crospovidone) in particular povidone K25. Preferably the binder is a polymer, more preferably a gel-forming polymer, still more preferably the binder is a cellulose or a derivative thereof, still more preferably L-hydroxypropyl cellulose, and most preferably a combination of L-hydroxypropyl cellulose and hydroxypropyl cellulose.

Hydroxypropyl cellulose is a partially substituted poly (hydroxypropyl) ether of cellulose. It may contain not more than 0.6% of silica or another suitable anticaking agent. Hydroxypropyl cellulose is commercially available in a number of different grades that have various solution viscosities. Molecular weight ranges from 50000-1250000. Hydroxypropylcellulose is partly O-(2-hydroxypropylated) cellulose. It contains 53.4% to 80.5% of hydroxypropoxy groups with reference to the dried substance. The average grade of polymerization ranges from 200 to 300. The molar grade of substitution is around 4.

"Low-substituted hydroxypropyl cellulose" (L-HPC or LHPC) is a low-substituted poly(hydroxypropyl) ether of cellulose. It is commercially available in a number of different grades that have different particle sizes and substitution levels.

Low-substituted hydroxypropyl cellulose contains 5% to 16% hydroxypropoxy groups with reference to the dried substance. The molar grade of substitution is <1. In particular low-substituted hydroxypropyl cellulose is a low-substituted O-(2-hydroxypropylated) cellulose contains not less than 5.0% and not more than 16.0% of hydroxypropoxy groups ($—OCH_2CHOHCH_3$), calculated on the dried basis.

Low-Substituted Hydroxypropyl Cellulose is a low-substituted O-(2-hydroxypropylated) cellulose contains not less than 5.0% and not more than 16.0% of hydroxypropoxy groups ($—OCH_2CHOHCH_3$), calculated on the dried basis.

"Polyvinyl caprolactam-polyvinyl acetate-polyethylene glycol graft copolymer (PCL-PVAc-PEG) (Soluplus®)" has the following chemical structure:

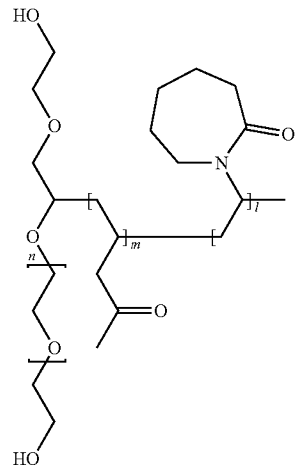

"Povidone" is synonymously used for polyvinylpyrrolidone (PVP).

Polyvinylpyrrolidone consists of linear polymers of 1-ethenylpyrollidin-2-one. The different types of polyvinylpyrrolidone are characterized by the viscosity of their solutions, expressed by the K value. Polyvinylpyrrolidone is present as a white to yellowish white powder or flake and is readily soluble in water. The K value is a common classification in the plastics industry and is directly related to the average molar mass of the polymer. This makes it possible to deduce indirectly from the K value the degree of polymerization and thus the chain length. Povidone K25, povidone K30 or povidone K90 is commercially available. Preferably, povidone K25 is used as a binder. The approximate average molecular weight of povidone K25 is 30,000 g/mol (Da) between 28,000 g/mol (Da) to 34,000 g/mol (Da).

A preferred embodiment of the invention is therefore directed to a systemic formulation containing or consisting of (S,E)-methyl-7-(1-(2-(2-ethylbutylamino)-2-oxoethyl)-2- oxo-1,2-dihydro-pyridin-3-ylamino)-6-(1-methyl-1H-imidazole carboxamido)-7-oxohept-2-enoate or an enantiomer, a solvate, a hydrate or a pharmaceutically acceptable salt thereof, and at least one excipient, wherein at least one excipient is a binder.

A preferred embodiment of the invention is therefore directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one binder.

A preferred embodiment of the invention is therefore directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a binder, and wherein the binder is polyvinylpyrrolidone.

A preferred embodiment of the invention is therefore directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one polyvinylpyrrolidone.

A preferred embodiment of the invention is therefore directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a binder, wherein the binder is polyvinylpyrrolidone, and wherein the polyvinylpyrrolidone is povidone K25.

A preferred embodiment of the invention is therefore directed to a systemic formulation containing or consisting of (S,E)-methyl-7-(1-(2-(2-ethylbutylamino)oxoethyl)-2-oxo-1,2-dihydro-pyridin-3-ylamino)-6-(1-methyl-1H-imidazole pharmaceutically acceptable salt thereof, and povidone K25.

Moreover, the systemic formulation according to the invention can comprise a binder and/or a polymeric precipitation inhibitor.

A preferred embodiment of the invention is therefore directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of binder and polymeric precipitation inhibitor.

A preferred embodiment of the invention is therefore directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one binder and/or at least one polymeric precipitation inhibitor.

A preferred embodiment of the invention is therefore directed to a systemic formulation containing or consisting of (S,E)-methyl-7-(1-(2-(2-ethylbutylamino)-2-oxoethyl)-2- oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a binder and polymeric precipitation inhibitor. Preferably, at least one excipient functions as a binder and a polymeric precipitation inhibitor at the same time. Thus, at least one excipient is a binder and polymeric precipitation inhibitor.

A preferred embodiment of the invention is therefore directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one compound being a binder and polymeric precipitation inhibitor.

A preferred embodiment of the invention is therefore directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxcohept-2-enoate or an enantiomer, a solvate, a hydrate or a pharmaceutically acceptable salt thereof, at least one binder and at least one polymeric precipitation inhibitor.

Preferably, the "binder" is selected from the group comprising or consisting of: sugar, such as sucrose; polysaccharides such as xanthan gum, guar gum, carrageenan, starches derived from wheat, corn, rice and potatoes, and preagglutinated (modified) starch derived from wheat, corn, rice and potatoes, sodium starch glycolate; natural gums such as acacia gum, gelatin and tragacanth; derivatives of sea weed such as alginic acid, sodium alginate and ammonium calcium alginate, cellulose or derivatives thereof such as hydroxypropyl cellulose, L-hydroxypropyl cellulose, low-substituted hydroxypropyl cellulose, methyl cellulose, sodium carboxymethylcellulose, hydroxypropyl methylcellulose, and polyvinylpyrrolidone (crospovidone) in particular povidone K25; and "polymeric precipitation inhibitor" is selected from the group comprises or consists of: microcrystalline cellulose (MCC), cellulose acetate phthalate (CAP), cellulose acetate terephthalate, cellulose acetate isophthalate, cellulose acetate butyrate (CAB), cellulose acetate trimellitate (CAT), methylcellulose (MC), methylcellulose acetate phthalate, ethylcellulose (EC), carboxymethyl cellulose (CMC), sodium carboxymethyl cellulose, carboxymethylethylcellulose (CMEC), hydroxymethylcellulose (HMC), hydroxyethylcellulose (HEC), hydroxypropyl cellulose (HPC or hyprolose), L-hydroxypropyl cellulose, hydroxypropylmethylcellulose (HPMC or hypromellose), carboxymethyl hydroxyethyl cellulose (CMHEC), sodium carboxymethyl hydroxyethyl cellulose (NaCMHEC), hydroxypropyl methylcellulose phthalate (HPMCP, hypromellose phtahalate), hydroxypropyl methylcellulose acetate succinate (HPMCAS, hypromellose acetate succinate), polyethylene glycol (PEG), polyethylene oxide (PEO), polyether polyol, poly(propylene glycol) bis(2-aminopropyl ether) (PPGAE), poly(ethylene oxide)-poly (propylene oxide)-poly (ethylene oxide) (PEO-PPO-PEO, poloxamer) such as poloxamer 188 and poloxamer 407, polyvinyl alcohol (PVA), polyvinyl acetate phthalate (PVAP), polyvinylpyrrolidone (PVP), polyvinylpyrrolidone-co-polyvinyl acetate (PVPVA), polyvinyl caprolactam-polyvinyl acetate-polyethylene glycol graft copolymer (Soluplus®), poly(acrylic acid) (PAA), poly (acrylamide/acrylic acid) (PAC-AC), polymethylacrylate (PMA), polymethacrylic acid, poly(methacrylic acid/methyl methacrylate), poly(methacrylic acid/ethyl acrylate), and a combination of at least two of the above-mentioned polymeric precipitation inhibitors.

A preferred embodiment of the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido) oxohept-2-enoate or an enantiomer, a solvate, a hydrate or a pharmaceutically acceptable salt thereof, and at least one excipient, wherein at least one excipient is selected from the group comprising or consisting of binder and polymeric precipitation inhibitor, and wherein the polymeric precipitation inhibitor is polyvinyl alcohol (PVA), polyvinyl caprolactam-polyvinyl acetate-polyethylene glycol graft copolymer (Soluplus®), cellulose, a cellulose derivative, a combination of cellulose and a derivative or combination of cellulose derivatives.

A preferred embodiment of the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one binder and/or at least one polymeric precipitation inhibitor, wherein the polymeric precipitation inhibitor is polyvinyl alcohol (PVA), polyvinyl caprolactam-polyvinyl acetate-polyethylene glycol graft copolymer (Soluplus®), cellulose, a cellulose derivative, a combination of cellulose and a derivative or combination of cellulose derivatives.

A preferred embodiment of the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of binder and polymeric precipitation inhibitor, and wherein the polymeric precipitation inhibitor is polyvinyl alcohol (PVA), polyvinyl caprolactam-polyvinyl acetate-polyethylene glycol graft copolymer (Soluplus®), L-hydroxypropyl cellulose, hydroxypropyl cellulose, or a combination of L-hydroxypropyl cellulose and hydroxypropylcellulose.

A preferred embodiment of the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)oxohept-2-enoate or an enantiomer, a solvate, a hydrate or a pharmaceutically acceptable salt thereof, and at least one binder and/or at least one polymeric precipitation inhibitor, wherein the polymeric precipitation inhibitor is polyvinyl alcohol (PVA), polyvinyl caprolactam-polyvinyl acetate-polyethylene glycol graft copolymer (Soluplus®), L-hydroxypropyl cellulose, hydroxypropyl cellulose, or a combination of L-hydroxypropyl cellulose and hydroxypropyl cellulose.

An embodiment of the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of binder and polymeric precipitation inhibitor, wherein the polymeric precipitation inhibitor is polyvinyl alcohol (PVA), polyvinyl caprolactam-polyvinyl acetate-polyethylene glycol graft copolymer (Soluplus®), L-hydroxypropyl cellulose, hydroxypropyl cellulose or a combination of L-hydroxypropyl cellulose, and wherein the binder is L-hydroxypropyl cellulose, hydroxypropyl cellulose, a combination of L-hydroxypropyl cellulose and hydroxypropyl cellulose, and/or polyvinylpyrrolidone.

An embodiment of the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one polymeric precipitation inhibitor selected from the group comprising or consisting of polyvinyl alcohol (PVA), polyvinyl caprolactam-polyvinyl acetate-polyethylene glycol graft copolymer (Soluplus®), L-hydroxypropyl cellulose and hydroxypropyl cellulose and at least one binder selected from the group L-hydroxypropyl cellulose, hydroxypropyl cellulose and hydroxypropyl cellulose, and/or polyvinylpyrrolidone.

A preferred embodiment of the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a binder and/or at least one excipient is a polymeric precipitation inhibitor, and wherein the polymeric precipitation inhibitor is polyvinyl alcohol (PVA), polyvinyl caprolactam-polyvinyl acetate-polyethylene glycol graft copolymer (Soluplus®), cellulose, a cellulose derivative, a combination of cellulose and a cellulose derivative or combination of cellulose derivatives, and the binder is cellulose, a cellulose derivative, a combination of cellulose and a derivative or combination of cellulose derivatives, and/or povidone K25.

A preferred embodiment of the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one binder and/or at least one polymeric precipitation inhibitor, and wherein the polymeric precipitation inhibitor is polyvinyl alcohol (PVA), polyvinyl caprolactam-polyvinyl acetate-polyethylene glycol graft copolymer (Soluplus®), cellulose, a cellulose derivative, a combination of cellulose and a derivative or combination of cellulose derivatives, and the binder is cellulose, a cellulose derivative, a combination of cellulose and a derivative or combination of cellulose derivatives, and/or povidone K25.

Another preferred embodiment of the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a binder and/or at least one excipient is a polymeric precipitation inhibitor, wherein the polymeric precipitation inhibitor is polyvinyl alcohol (PVA), polyvinyl caprolactam-polyvinyl acetate-polyethylene glycol graft copolymer (Soluplus®), L-hydroxypropyl cellulose, hydroxypropyl cellulose or a combination of L-hydroxypropyl cellulose, and wherein the binder is L-hydroxypropyl cellulose, hydroxypropyl cellulose, a combination of L-hydroxypropyl cellulose and hydroxypropyl cellulose, and/or povidone K25.

Another preferred embodiment of the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one binder and/or at least one polymeric precipitation inhibitor, wherein the polymeric precipitation inhibitor is polyvinyl alcohol (PVA), polyvinyl caprolactam-polyvinyl acetate-polyethylene glycol graft copolymer (Soluplus®), L-hydroxypropyl cellulose, hydroxypropyl cellulose or a combination of L-hydroxypropyl cellulose, and wherein the binder is L-hydroxypropyl cellulose, hydroxypropyl cellulose, a combination of L-hydroxypropyl cellulose and hydroxypropyl cellulose, and/or povidone K25.

A preferred embodiment of the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a binder and/or at least one excipient is a polymeric precipitation inhibitor, wherein the polymeric precipitation inhibitor is polyvinyl alcohol (PVA), polyvinyl caprolactam-polyvinyl acetate-polyethylene glycol graft copolymer (Soluplus®), L-hydroxypropyl cellulose, hydroxypropyl cellulose, or a combination of L-hydroxypropyl cellulose and hydroxypropyl cellulose, wherein the binder is povidone K25.

A preferred embodiment of the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one binder and/or at least one polymeric precipitation inhibitor, wherein the polymeric precipitation inhibitor is polyvinyl alcohol (PVA), polyvinyl caprolactam-polyvinyl acetate-polyethylene glycol graft copolymer (Soluplus®), L-hydroxypropyl cellulose, hydroxypropyl cellulose, or a combination of L-hydroxypropyl cellulose and hydroxypropyl cellulose, wherein the binder is povidone K25.

The positive data of the pharmacokinetic study in human confirms the high bioavailability of compound (I). A high bioavailability in this context has to be understood in comparison to the animal studies which have been performed previously.

The STAM- and UUO mouse model studies demonstrate an anti-fibrotic effect on the liver and kidney being achieved by the administration of a systemic formulation containing the compound according to formula (I). Therefore, the drug of formula (I) administered systemically shows a high anti-fibrotic effect at the target site, and thereby indicates a systemic bioavailability. Thus, the administration of an oral formulation containing the drug of formula (I) exhibits a high anti-fibrotic effect at the target site, and thus a systemic availability (bioavailability) can be derived, i.e. the drug is absorbed at the target tissue.

The addition of an acidifier ensures the complete dissolution of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate in the stomach but the pH in the small intestine increases from 2 to 6, and thus the drug can precipitate before it can be absorbed by the small intestine. In order to ensure a complete dissolution of said compound in the small intestine, the formulation according to the invention contains preferably an acidifier, and/or a polymeric precipitation inhibitor. Moreover, it could be shown in example 9 that merely a dosage of 20 mg in human is sufficient to achieve drug concentrations in plasma, and thus a systemic availability.

The pharmacokinetic studies show that (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate is absorbed in the small intestine and a low dose of 20-50 mg is needed to achieve a therapeutic effective drug concentration in human (example 7, FIG. 6). In addition, an anti-fibrotic effect can already be achieved with a human dosage of 20 mg (example 9 and FIG. 9).

Moreover, off-target effects could not be observed. As aforementioned, this is particularly surprising due to the fact that TG2 is ubiquitously expressed in almost all cell types and cell compartments, it is present on the cell surface and gets secreted to the extracellular matrix, and is present in various organs, and thus it could be envisioned that off-target effects would be most likely.

Thus, the systemic formulation according to the invention can comprise an acidifier and/or a polymeric precipitation inhibitor. Preferably, the systemic formulation comprises an acidifier and a polymeric precipitation inhibitor.

A preferred embodiment according to the invention is directed to a systemic formulation containing or consisting of a solvate, a hydrate or a pharmaceutically acceptable salt thereof, and at least one excipient, wherein at least one excipient is selected from the group comprising or consisting of acidifier, and polymeric precipitation inhibitor.

A preferred embodiment of the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, at least one acidifier and at least one polymeric precipitation inhibitor.

A preferred embodiment of the invention is thus related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, at least one acidifier selected from adipic acid, fumaric acid and glutaric acid and at least one polymeric precipitation inhibitor.

A preferred embodiment of the invention is thus related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid and at least one polymeric precipitation inhibitor.

A preferred embodiment according to the invention is directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, and a polymeric precipitation inhibitor, and wherein the acidifier is selected from the group comprising or consisting of adipic acid, fumaric acid, and glutaric acid; and the polymeric precipitation inhibitor is selected from the group comprising or consisting of polyvinyl alcohol (PVA), polyvinyl caprolactam-polyvinyl acetate-polyethylene glycol graft copolymer (Soluplus®), cellulose and cellulose derivative.

A preferred embodiment according to the invention is directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, and a polymeric precipitation inhibitor, and wherein the acidifier is adipic acid, and the polymeric precipitation inhibitor is selected from the group comprising or consisting of polyvinyl alcohol (PVA), polyvinyl caprolactam-polyvinyl acetate-polyethylene glycol graft copolymer (Soluplus®), cellulose and cellulose derivative.

A preferred embodiment according to the invention is directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one acidifier and at least one polymeric precipitation inhibitor, wherein the acidifier is adipic acid, and the polymeric precipitation inhibitor is selected from the group comprising or consisting of polyvinyl alcohol (PVA), polyvinyl caprolactam-polyvinyl acetate-polyethylene glycol graft copolymer (Soluplus®), cellulose and cellulose derivative.

A preferred embodiment of the invention is thus related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, at least one acidifier and at least one polymeric precipitation inhibitor selected from the group comprising or consisting of polyvinyl alcohol (PVA), polyvinyl caprolactam-polyvinyl acetate-polyethylene glycol graft copolymer (Soluplus®), L-hydroxypropyl cellulose and hydroxypropyl cellulose.

A preferred embodiment of the invention is thus related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid and at least one polymeric precipitation inhibitor selected from the group comprising or consisting of polyvinyl alcohol (PVA), polyvinyl caprolactam-polyvinyl acetate-polyethylene glycol graft copolymer (Soluplus®), L-hydroxypropyl cellulose and hydroxypropyl cellulose.

A preferred embodiment according to the invention is directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, and polymeric precipitation inhibitor, and wherein the acidifier is adipic acid, and the polymeric precipitation inhibitor is polyvinyl alcohol (PVA), polyvinyl caprolactam-polyvinyl acetate-polyethylene glycol graft copolymer (Soluplus®), L-hydroxypropyl cellulose, hydroxypropyl cellulose or a combination of L-hydroxypropyl cellulose and hydroxypropyl cellulose.

A preferred embodiment according to the invention is directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one acidifier, and/or at least one polymeric precipitation inhibitor, and wherein the acidifier is adipic acid, and the polymeric precipitation inhibitor is polyvinyl alcohol (PVA), polyvinyl caprolactam-polyvinyl acetate-polyethylene glycol graft copolymer (Soluplus®), L-hydroxypropyl cellulose, hydroxypropyl cellulose or a combination of L-hydroxypropyl cellulose and hydroxypropyl cellulose.

A systemic formulation containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, wherein the systemic formulation further comprises at least one excipient, wherein at least one excipient is selected from the group comprising or consisting of acidifier and polymeric precipitation inhibitor, wherein the acidifier is selected from the group consisting of ascorbic acid, organic di-carboxylic acid such as oxalic acid, malonic acid, succinic acid, glutaric acid, tartaric acid, fumaric acid, maleic acid, malic acid, adipic acid, or glutamic acid, and organic tri-carboxylic acid such as citric acid, or sodium hydrogen citrate.

A systemic formulation containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, wherein the systemic formulation further comprises at least one excipient, wherein at least one excipient is selected from the group comprising or consisting of acidifier and binder, wherein the acidifier is selected from the group consisting of ascorbic acid, organic di-carboxylic acid such as oxalic acid, malonic acid, succinic acid, glutaric acid, tartaric acid, fumaric acid, maleic acid, malic acid, adipic acid, or glutamic acid, and organic tri-carboxylic acid such as citric acid, or sodium hydrogen citrate, and wherein the binder is selected from the group consisting of sugar, such as sucrose; polysaccharides such as xanthan gum, guar gum, carrageenan, starches derived from wheat, corn, rice and potatoes, and preagglutinated starch derived from wheat, corn, rice and potatoes, sodium starch glycolate; polyacrylic acids; natural gums such as acacia gum, gelatin and tragacanth; derivatives of sea weed such as alginic acid, sodium alginate and ammonium calcium alginate, cellulose or derivative thereof such as hydroxypropyl cellulose, L-hydroxypropyl cellulose, methyl cellulose and sodium carboxymethylcellulose and hydroxypropyl methylcellulose, or polyvinylpyrrolidone.

The systemic formulation according to the invention can comprise an acidifier, a polymeric precipitation inhibitor, and/or a binder.

An embodiment according to the invention is directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, polymeric precipitation inhibitor and binder.

A preferred embodiment according to the invention is directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, at least one acidifier, at least one acidifier, at least one polymeric precipitation inhibitor and at least one binder.

A more preferred embodiment according to the invention is directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, at least one acidifier, at least one acidifier, at least one polymeric precipitation inhibitor and at least one binder, wherein the acidifier is adipic acid, the polymeric precipitation inhibitor is polyvinyl alcohol (PVA), polyvinyl caprolactam-polyvinyl acetate-polyethylene glycol graft copolymer (Soluplus®), L-hydroxypropyl cellulose, hydroxypropyl cellulose or a combination of L-hydroxypropyl cellulose and hydroxypropyl cellulose, and wherein the binder is polyvinylpyrrolidone.

The systemic formulation according to the invention can comprise a disintegrant. Thus, the excipient can be a disintegrant. The term "disintegrant" refers to materials added to the composition in order to support disintegration of the formulation and release of the active pharmaceutical ingredient. Suitable disintegrants include starches, modified starches which are soluble in cold water, such as sodium carboxymethyl starch; cellulose derivatives such as methylcellulose and sodium carboxymethylcellulose, microcrystalline cellulose and crosslinked microcrystalline cellulose such as sodium croscarmellose; alginates such as alginic acid and sodium alginate; clays such as bentonites and foaming mixtures; effervescent compounds such as combinations of citric acid, tartaric acid, sodium citrate, disodium hydrogen citrate, monosodium citrate, sodium and/or potassium hydrogen carbonate that react in the presence of water to give carbon dioxide. Preferably, the disintegrant is sodium croscarmellose.

Microcrystalline cellulose is a purified, partially depolymerized cellulose that occurs as a white, odorless, tasteless, crystalline powder composed of porous particles. It is manufactured by treating alpha-cellulose, obtained as a pulp from fibrous plant material, with mineral acids. Several different grades are commercially available that differ in their method of manufacture, particle size, moisture, flow, and other physical properties. The larger-particle-size-grades generally provide better flow properties. Low-moisture-grades are used with moisture-sensitive materials. Higher-density grades have improved flowabilities.

The microcrystalline cellulose used herein can have a nominal mean particle size of 100 μm and a moisture content of 5.0%.

An embodiment of the invention is therefore directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a disintegrant.

An embodiment of the invention is therefore directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one disintegrant.

The systemic formulation according to the invention can comprise an acidifier, a polymeric precipitation inhibitor, a binder and/or a disintegrant.

An embodiment according to the invention is directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, polymeric precipitation inhibitor, binder and disintegrant.

The systemic formulation according to the invention can comprise a lubricant/glidant. The excipient can thus be a lubricant/glidant. Lubricants/glidants are materials preventing caking, improving the flow characteristics of granulates so that the flow is smooth and uniform, and reducing t the friction between surfaces in direct contact in order to allow for the tablet, granulate, etc. to be released from the casting mold or pressing mold, after compression. Lubricants/glidants include sodium benzoate, metallic stearate such as magnesium stearate, calcium stearate, or potassium stearate, stearic acid, high melting point waxes, inorganic lubricants/glidants such as silicon dioxide and talc and other lubricants/glidants such as sodium oleate, and polyethylene glycols. Preferably, the lubricant/glidant is talc or silicon dioxide. Due to the fact that lubricants/glidants have to be present on the surface of the granules as well as between the granules and parts of the equipment they are typically added during the last step prior to encapsulation or compression.

A preferred embodiment of the invention is therefore directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a lubricant/glidant.

A preferred embodiment of the invention is therefore directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one lubricant/glidant.

The systemic formulation according to the invention can comprise or consist of an acidifier, a polymeric precipitation inhibitor, a binder and/or a lubricant/glidant.

A preferred embodiment according to the invention is directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, polymeric precipitation inhibitor, binder, and lubricant/glidant.

A preferred embodiment according to the invention is directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, polymeric precipitation inhibitor, binder, and lubricant/glidant.

The systemic formulation according to the invention can comprise or consist of an acidifier, polymeric precipitation inhibitor, a binder, a disintegrant, and/or a lubricant/glidant.

A preferred embodiment according to the invention is directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, polymeric precipitation inhibitor, binder, disintegrant, and lubricant/glidant.

Furthermore, the systemic formulation according to the invention can also comprise as an excipient diluents/fillers/binders, sweetening agents, flavoring agents, buffering agents, antioxidants, emulsifiers, solubilizer/wetting agent and/or preservatives.

A suitable diluent/filler/binder is a substance which usually forms the largest part of the composition or dosage form. A suitable diluent/filler/binder includes sugars such as lactose, sucrose, mannitol and sorbitol; starches derived from wheat, corn, rice and potatoes; and cellulose such as microcrystalline cellulose, calcium hydrogen phosphate dihydrate, and calcium sulfate. Preferably, the diluent/filler/binder is cellulose and/or mannitol. Most preferably, the diluent/filler/binder is microcrystalline cellulose and/or mannitol. Preferably, the diluent/filler/binder is microcrystalline cellulose when the formulation is a tablet, and the diluent/filler/binder is mannitol when the formulation is a capsule.

The addition of mannitol further increases the porosity and therefore wettability of the granules. A preferred embodiment of the invention is therefore directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is a diluent/filler/binder.

The systemic formulation according to the invention can comprise or consists of an acidifier, a polymeric precipitation inhibitor, a binder, a disintegrant, a lubricant/glidant and/or a diluent/filler/binder.

An embodiment of the invention is directed to a formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, polymeric precipitation inhibitor, binder, disintegrant, lubricant/glidant and diluent/filler/binder.

An embodiment of the invention is directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, at least one acidifier, at least one polymeric precipitation inhibitor, at least one a binder, at least one disintegrant, at least one lubricant/glidant and at least one diluent/filler/binder.

The preferred preparations are provided in an administrable form suitable for oral application, such as tablets such as uncoated tablets, coated tablets, effervescent tablets, soluble tablets, chewable tablets, oral lyophilisates, lozenges, pastilles, compressed lozenges, sublingual tablets, buccal tablets, granules, effervescent granules and capsules. More preferably, the oral formulation is a tablet or capsule. Uncoated and coated, and capsules, either hard or soft are the most preferred pharmaceutical formulations.

An embodiment of the present invention is directed to a systemic formulation containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, wherein the systemic formulation is a tablet, capsule, powder, or granule.

The systemic formulation according to the invention can comprise other ingredients such a unavoidable impurities, ingredients for the capsule including colorants of the capsule. Also in a tablet, a colorant as other ingredient can be present.

Furthermore, components used for coating a tablet are also encompassed by the term "other ingredients".

The shell of the capsule can comprise a colorant. As used herein, the term "colorant" includes pigments such as white pigments. The colorant can be among others iron oxide in particular iron(III)oxide, iron(II,III) oxide or hydrated ferric oxide or titanium dioxide.

"Tablet" means a compressed solid dosage form containing at least one active pharmaceutical ingredient with suitable excipients. The tablet can be produced by compressing mixtures or granulates obtained by wet granulation, dry granulation or compaction, which are known to the one skilled in the art.

The term "capsule" refers to a special container or shell composed of methylcellulose, polyvinyl alcohols or gelatins or denatured gelatins or starches, in which the active agents can be enclosed. Typically, hard shell capsules are prepared from hydroxypropyl methylcellulose or from mixtures of porcine bone and skin gelatins having comparatively high gel strength. The shell of the capsule can contain small amounts of colorants, opacifiers, softening agents and preservatives. "Soft shell capsules" contains gelatin as a basic polymer, one or more softening agents such as glycerol or sorbitol in a higher amount as well as water. In general, the amount of the softening agent is 20-30% by weight of the capsule shell, the amount of the gelatin is 40-45% by weight of the capsule shell, and amount of water is 30-35% by weight of the capsule shell. After the drying of the capsule, the amount of water is 7-8% by weight of the capsule shell.

The capsule shell can comprise gelatine, hydroxypropyl methylcellulose (HMPC), polysaccharides such as starch, and carrageenan; and/or synthetic polymers such as compolymers of polyvinylalcohol. Furthermore, the shell of the capsule can comprise a colorant. As used herein, the term "colorant" includes pigments such as white pigments. The colorant can be among others iron oxide in particular iron(III)oxide, iron(II,III) oxide or hydrated ferric oxide, titanium dioxide, natural dyes, azo and xanthane compounds. Moreover, the capsule shell may comprise a preservative such as p-hydroxybenzoic acid esters or means to improve the flavour such as ethylvanillin. In addition, the capsule shell can comprise a surfactant such a sodium lauryl sulfate.

"Powders" for compositions refer to powder mixtures/blends containing the active components and suitable excipients which can be suspended in water or juices prior to use. Spherical-shaped granules are also referred to pellets or beads.

"Granules" refer to dry and solid grains. Each grain represents an agglomerate of powder particles.

While the wrapping or embedding method drug particles are treated, the coating method is related to the dosage form itself. Tablets, the center of dragees or capsules are coated with coating layer, wherein excipients such as derivative of cellulose, cellulose ether such as hydroxypropyl methylcellulose (HMPC), synthetic polymers, shellac, corn protein zein or other polysaccharides and anionic copolymers of methacrylic acid and methyl methacrylate. The coating can further comprise colorants such as titanium dioxide, iron (III)oxide, iron(II,III) oxide or hydrated ferric oxide, lactose monohydrate, and or carnauba wax. Also capsule can be coated.

Sustained-release-type formulation are known in the state of the art for the provision of a controlled release rate of any one or more components or active components, in order to optimize the therapeutic effect, i.e. the inhibitory activity and the like. The pharmacological optimal concentration is guaranteed for a certain time above the period of effect of a single dosage. Suitable dosage forms for sustained release include layered tablets containing layers with varying degradation rates or controlled release polymeric matrices impregnated with the active components and in the form of a tablet or capsule containing such impregnated or encapsulated porous polymeric matrices. A sustained-release type formulation would impede a fast-release of the compound. Herein, it is desired that a high concentration of the drug is quickly released to the target site after the administration. Consequently, sustained-release type formulations are not preferred and should actually be avoided for the purposes of the present invention, because preliminary results indicate that such formulations cannot provide the required high drug concentration according to the present invention.

The systemic formulation according to the invention can be in form of a capsule or tablet, i.e. active agent and the excipient can be filled in the capsule. An embodiment according to the invention is a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, wherein the systemic formulation is in form of a capsule or tablet.

A preferred embodiment according to the invention is a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, and polymeric precipitation inhibitor, wherein the systemic formulation is in form of a capsule or tablet.

A preferred embodiment according to the invention is a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, at least one acidifier, and at least one polymeric precipitation inhibitor, wherein the systemic formulation is in form of a capsule or tablet.

Another preferred embodiment according to the invention is a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, polymeric precipitation inhibitor, and binder, wherein the systemic formulation is in form of a capsule or tablet.

Another preferred embodiment according to the invention is a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, at least one acidifier, at least one polymeric precipitation inhibitor, and at least one binder, wherein the systemic formulation is in form of a capsule or tablet.

Another preferred embodiment according to the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least at excipient, wherein at least one excipient is selected from the group comprising or consisting of acidifier, polymeric precipitation inhibitor, binder, disintegrant, and a lubricant/glidant, wherein the systemic formulation is in form of a capsule or tablet.

Another preferred embodiment according to the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, at least one acidifier, at least one polymeric precipitation inhibitor, at least one binder, at least one disintegrant, and at least one lubricant/glidant, wherein the systemic formulation is in form of a capsule or tablet.

Another preferred embodiment according to the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least at excipient, wherein at least one excipient is selected from the group comprising or consisting of acidifier, polymeric precipitation inhibitor, diluent/filler/binder, disintegrant, lubricant/glidant, and diluent/filler/binder, wherein the systemic formulation is in form of a capsule or tablet.

Another preferred embodiment according to the invention is related to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, at least one acidifier, at least one polymeric precipitation inhibitor, at least one binder, at least one disintegrant, at least one lubricant/glidant, and at least one diluent/filler/binder, wherein the systemic formulation is in form of a capsule or tablet.

The preferred pharmaceutical formulation is for oral administration. Therefore, preferred pharmaceutical formulations are systemic formulation in form of an enteral or parenteral formulation for oral administration. Consequently, especially capsules and tablets are the most preferred enteral or parenteral formulation for oral administration and especially these capsules and tablets which ensure fast release of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, and thereby ensuring high drug concentrations. Therefore, sustained release formulations are not suitable and should actually not be used for the purposes of the present invention.

Moreover, pharmaceutical formulations for oral administration containing adipic acid are preferred. More preferred are systemic formulations in form of an enteral or parenteral formulation for oral administration containing adipic acid. Most preferred are capsules and tablets for oral administration containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and adipic acid.

Furthermore, in order to further improve the performance of the formulation the specific PSD (particle size distribution), and/or PSR (particle size range) can be adapted.

Therefore, an embodiment according to the invention is directed to a systemic formulation containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

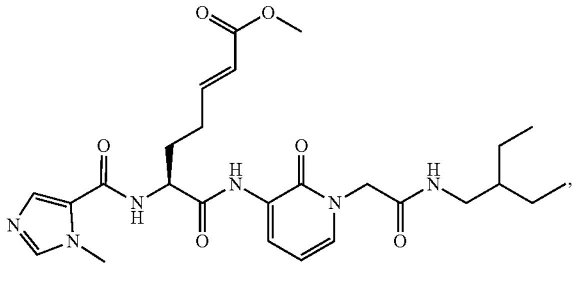

or a solvate, a hydrate or a pharmaceutically acceptable salt of formula (I), wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size range from 0.1 to 100 μm.

It is furthermore preferred that the particle size of the (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof is within the range of 0.1 μm to 100 μm, preferably in the range of 0.5 μm to 50 μm and more preferably in the range of 1.0 μm to 20 μm. Thus, the particle size range (PSR) of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof is from 0.1 μm to 100 μm, from 0.5 μm to 50 μm, or from 1.0 μm to 20 μm. Preferably, the particle size of the drug according to formula (I) is ≤10 μm.

Another preferred embodiment according to the invention is a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, and L-hydroxypropyl cellulose, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size range from 0.1 μm to 100 μm.

Therefore, an embodiment according to the invention is directed to a systemic formulation containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

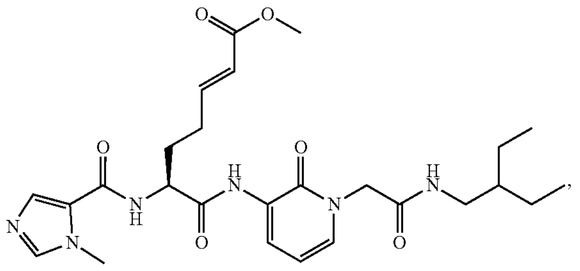

or an enantiomer, a solvate, a hydrate or a pharmaceutically acceptable salt of formula (I), wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size distribution which is defined by d(0.95) 25 μm, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof is preferably micronized.

Moreover it is preferred that the particle size distribution of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof is characterized by d(0.1) from 0.1 to 5 μm, d(0.5) from 0.3 to 10 μm, d(0.95) from 3 to 25 μm, more preferably d(0.1) from 0.2 to 3 μm, d(0.5) from 0.4 to 7.5 μm and d(0.95) from 2 to 15 μm, and most preferably d(0.1) from 0.3 to 3 μm, d(0.5) from 0.5 to 5 μm and d(0.95) from 1 to 10 μm.

The particle size distribution is measured by laser light diffraction (Malvern analysis, sample dispersed in n-hexane and sorbitane monooleate). Thereby, the laser light is scattered in dependence of the particle size. A diffraction pattern results from the angle dependent scattered light intensity, the particle size can be calculated.

The parameter d(0.1) refers to the diameter at which 10% of the total volume of particles in the sample is comprised of particles with a diameter less than the indicated value or range of values when analysed by laser diffraction (Malvern analysis, sample dispersed in n-hexane and sorbitane monooleate). Thus d(0.1)=0.1 to 5 μm means that the upper limit of the particle size range defining the 10% of smallest particles in the sample is between 0.1 μm to 5 μm. Thus 10% of the total particles have a particle size of not more than d(0.1) meaning in this case that they have a maximum size of 0.1 μm to 5 μm.

Accordingly the parameter d(0.5) refers to the diameter at which 50% of the total volume of particles in the sample is comprised of particles with a diameter less than the indicated value or range of values when analysed by laser diffraction (Malvern analysis, sample dispersed in n-hexane and sorbitane monooleate). Thus d(0.5)=0.3 to 10 μm means that the upper limit of the particle size range defining the 50% of smallest particles in the sample is between 0.3 μm to 10 μm. Thus 50% of the total particles have a particle size of not more than d(0.5) meaning in this case that they have a maximum size of 0.3 μm to 10 μm.

Accordingly the parameter d(0.95) refers to the diameter at which 95% of the total volume of particles in the sample is comprised of particles with a diameter less than the indicated value or range of values when analysed by laser diffraction (Malvern analysis, sample dispersed in n-hexane and sorbitane monooleate). Thus d(0.95)=3 to 25 μm means that the upper limit of the particle size range defining the 95% of smallest particles in the sample is between 3 μm to 25 μm. Thus 95% of the total particles have a particle size of not more than d(0.95) meaning in this case that they have a maximum size of 3 μm to 25 μm.

Another embodiment of the present invention is directed to a systemic formulation containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, and L-hydroxypropyl cellulose, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size distribution which is defined by d(0.95) 25 μm.

A preferred embodiment of the present invention is directed to a systemic formulation containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size distribution which is defined by d(0.1) from 0.1 to 5 μm, d(0.5) from 0.3 to 10 μm, and d(0.95) from 3 to 25 μm.

A more preferred embodiment according to the invention is a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, and L-hydroxypropyl cellulose, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size distribution which is defined by d(0.1) from 0.1 to 5 μm, d(0.5) from 0.3 to 10 μm, and d(0.95) from 3 to 25 μm.

A still more preferred embodiment according to the invention is a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, and L-hydroxypropyl cellulose, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size distribution which is defined by d(0.1) from 0.2 to 3 μm, d(0.5) from 0.4 to 7.5 μm and d(0.95) from 2 to 15 μm.

A even more preferred embodiment according to the invention is a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, L-hydroxypropyl cellulose, sodium croscarmellose, and talc, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size distribution which is defined by d(0.1) from 0.1 to 5 μm, d(0.5) from 0.3 to 10 μm, and d(0.95) from 3 to 25 μm.

A particularly preferred embodiment according to the invention is a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, L-hydroxypropyl cellulose, sodium croscarmellose, talc, gelatine and titanium dioxide, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate have a particle size distribution which is defined by d(0.1) from 0.1 to 5 μm, d(0.5) from 0.3 to 10 μm, and d(0.95) from 3 to 25 μm.

Another particularly preferred embodiment of the invention is related to a systemic formulation comprising or consisting of (S,E)-methyl-7-(1-(2-(2-ethylbutylamino)-2-oxoehtyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, L-hydroxypropyl cellulose, povidone K25, sodium croscarmellose, microcrystalline cellulose and silicon dioxide, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate have a particle size distribution which is defined by d(0.1) from 0.1 to 5 μm, d(0.5) from 0.3 to 10 μm, and d(0.95) from 3 to 25 μm.

Therefore, an embodiment according to the invention is directed to a systemic formulation containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

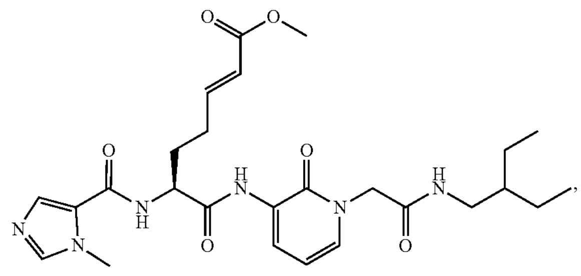

or an enantiomer, a solvate, a hydrate or a pharmaceutically acceptable salt of formula (I), wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size range from 0.1 to 100 μm, and a particle size distribution which is defined by d(0.95)≤25 μm.

Thus, preferred are systemic formulations containing (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxo-hept-2-enoate or an enantiomer, a solvate, a hydrate or a pharmaceutically acceptable salt thereof, wherein the (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxo-hept-2-enoate or an enantiomer, a solvate, a hydrate or a pharmaceutically acceptable salt thereof is in form of particles having a particle size distribution which is defined by d(0.95)≤25 μm.

A preferred embodiment according to the invention is a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, and L-hydroxypropyl cellulose, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size range from 0.1 to 100 μm, and a particle size distribution which is defined by d(0.95)≤25 μm.

A more preferred embodiment according to the invention is a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, or an enantiomer, a solvate, a hydrate or a pharmaceutically acceptable salt thereof adipic acid, L-hydroxypropyl cellulose, hydroxypropyl cellulose, mannitol, sodium croscarmellose, and talc, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size range from 0.1 to 100 μm, and a particle size distribution which is defined by d(0.95)≤25 μm.

A particularly preferred embodiment according to the invention is a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, L-hydroxypropyl cellulose, hydroxypropyl cellulose, mannitol, sodium croscarmellose, talc, gelatine and titanium dioxide, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size range from 0.1 to 100 μm, and a particle size distribution which is defined by d(0.95)≤25 μm.

Another particularly preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, L-hydroxypropyl cellulose, povidone K25, sodium croscarmellose, microcrystalline cellulose and silicon dioxide, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size range from 0.1 to 100 μm, and a particle size distribution which is defined by d(0.95)≤25 μm.

The systemic formulation can contain (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or enantiomer, solvate, a hydrate, or a pharmaceutically acceptable salt in an amount of at least 0.01 mg, preferably at least 0.1 mg, more preferably at least 0.5 mg, even more preferably at least 1 mg, even more preferably at least 2 mg, even more preferably at least 3 mg, even more preferably at least 4 mg, even more preferably at least 5 mg, even more preferably 0.01 mg to 1000 mg, even more preferably 0.05 mg to 900 mg, even more preferably 0.10 mg to 800 mg, still more preferably 0.2 mg to 700 mg, still more preferably 0.3 mg to 600 mg, still more preferably 0.4 mg to 500 mg, still more preferably 0.5 mg to 500 mg, still more preferably 0.6 mg to 450 mg, still more preferably 0.7 mg to 400 mg, still more preferably 0.8 mg to 375 mg, still more preferably 0.9 mg to 350 mg, still more preferably 1.0 mg to 300 mg, still more preferably 1.25 mg to 300 mg, still more preferably 1.5 mg to 275 mg, still more preferably 1.75 mg to 250 mg, still more preferably 2.0 mg to 225 mg, mg, still more preferably 2.25 to 220 mg, still more preferably 2.5 to 220 mg, still more preferably 2.75 mg to 215 mg, still more preferably 3.0 mg to 210 mg, still more preferably 3.75 mg to 205 mg, still more preferably 4.0 mg to 205 mg, 4.5 mg to 200 mg, most preferably 5 mg to 200 mg per formulation.

The systemic formulation can contain (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or enantiomer, solvate, a hydrate or a pharmaceutically acceptable salt, solvate or a hydrate in an amount of 0.1 wt % to 99 wt %, preferably 0.2 wt % to 90 wt %, more preferably 0.3 wt % to 85 wt %, even more preferably 0.4 wt % to 80 wt %, even more preferably 0.5 wt % to 75 wt %, even more preferably 0.6 wt % to 70 wt %, even more preferably 0.7 wt % to 65 wt %, even more preferably 0.8 wt % to 60 wt %, even more preferably 0.9 wt % to 55 wt %, even more preferably 1 wt % to 50 wt %, even more preferably 1 wt % to 45 wt %, even more preferably 1.25 wt % to 45 wt %, even more preferably 1.5 wt % to 40 wt %, even more preferably 1.75 wt % to 35 wt %, even more preferably 2 wt % to 34 wt %, even more preferably 2.25 wt % to 33 wt %, even more preferably 2.5 wt % to 32 wt %, and most preferably 2.5 wt % to 31 wt %, even more preferably 2.5 wt % to 30.5 wt %, and even more preferably 2.6 wt % to 30.3 wt %, even more preferably 3 wt % to 30 wt %, even more preferably 3.5 wt % to 29 wt %, even more preferably 4 wt % to 28 wt %, even more preferably 4 wt % to 27 wt %, even more preferably 4.5 wt % to 27 wt %, and most preferably 5 wt % to 27 wt %. "Wt %" ("weight percent") refers to the weight percent in the composition.

The amount of the acidifier can range from 0.1 wt % to 80 wt %, preferably from 0.5 wt % to 77.5 wt %, more preferably from 1 wt % to 75 wt %, more preferably from 1.5 wt % to 72.5 wt %, more preferably from 2 wt % to 70 wt %, more preferably from 2.5 wt % to 62.5 wt %, more preferably from 3 wt % to 57.5 wt %, more preferably from 3.5 wt % to 55 wt %, even more preferably from 4 wt % to 55 wt %, even more preferably from 4.5 wt % to 55 wt %, even more preferably from 5 wt % to 54 wt %, even more preferably from 5.5 wt % to 53 wt %, even more preferably from 6 wt % to 52 wt %, even more preferably from 6.5 wt % to 51 wt %, even more preferably from 7 wt % to 50 wt %, even more preferably from 8 wt % to 49 wt %, even more preferably from 8.5 wt % to 49 wt %, and most preferably from 9 wt % to 49 wt %.

Moreover, the amount of the acidifier can range from 1.00 mg to 500 mg, more preferably from 1.25 mg 495 mg, still more preferably from 1.50 mg to 490 mg, still more preferably from 1.75 mg to 485 mg, still more preferably from 2.00 mg to 480 mg, still more preferably from 2.25 mg to 475 mg, still more preferably from 2.50 mg to 470 mg, still more preferably from 3.0 mg to 465 mg, still more preferably from 3.25 mg to 460 mg, still more preferably from 3.5 mg to 455 mg, even more preferably from 3.75 mg to 450 mg, even more preferably from 4.00 mg to 445 mg, even more preferably from 4.25 mg to 440 mg, still more preferably from 4.5 mg to 435 mg, still more preferably from 4.75 mg to 430 mg, still more preferably from 5.0 mg to 425 mg, still more preferably from 5.25 mg to 420 mg, still more preferably from 5.5 mg to 415 mg, still more preferably from 5.75 mg to 410 mg, still more preferably from 6.0 mg to 410 mg, still more preferably from 6.25 mg to 405 mg, still more preferably from 6.5 mg to 400 mg, still more preferably from 6.75 mg to 395 mg, still more preferably from 7.0 mg to 390 mg, still more preferably from 7.5 mg to 390 mg, still more preferably from 7.75 mg to 385 mg, still more preferably from 8.0 mg to 380 mg, still more preferably from 8.5 mg to 375 mg, still more preferably from 9 mg to 370 mg, still more preferably from 9 mg to 365 mg, still more preferably from 9 mg to 360 mg, still more preferably from 9 mg to 350 mg, still more preferably from 9 mg to 325 mg, still more preferably from 9 mg to 300 mg, still more preferably from 9 mg to 250 mg, still more preferably from 9 mg to 200 mg, and most preferably from 9 mg to 180 mg.

Furthermore, a mass ratio of the acidifier relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof can range from 15 to 0.1 m/m, preferably from 14.5 to 0.2 m/m, more preferably from 14.0 to 0.3 m/m, still more preferably from 13.5 to 0.4 m/m, still more preferably from 13.0 to 0.5 m/m, still more preferably from 12.5 to 0.6 m/m, still more preferably from 12.0 to 0.7 m/m, still more preferably from 11.75 to 0.8 m/m, still more preferably from 11.5 to 0.9 m/m, still more preferably from 11.5 to 1.0 m/m, still more preferably from 11.5 to 1.1 m/m, still more preferably from 11.5 to 1.2 m/m, still more preferably from 11.5 to 1.3 m/m, still more preferably from 11.5 to 1.4 m/m, still more preferably from 11.5 to 1.5 m/m, still more preferably from 11.5 to 1.6 m/m, still more preferably from 11.5 to 1.7 m/m, and most preferably from 11.5 to 1.8 m/m.

The amount of the polymeric precipitation inhibitor can vary from 0.1 wt % to 40 wt %, preferably 0.5 wt % to 39 wt %, more preferably 1 wt % to 38 wt %, still more preferably 1.25 wt % to 38 wt %, still more preferably 1.5 wt % to 37 wt %, still more preferably 1.75 wt % to 36 wt %, still more preferably 2 wt % to 35 wt %, still more preferably 1.5 wt % to 34 wt %, still more preferably 1.6 wt % to 33 wt %, still more preferably 1.7 wt % to 32 wt %, still more preferably 1.8 wt % to 31 wt %, still more preferably 3.5 wt % to 30 wt %, still more preferably 4 wt % to 29 wt %, still more preferably 4.5 wt % to 28.5 wt %, most preferably 5 wt % to 28.5 wt %. Furthermore, the amount of the polymeric precipitation inhibitor can range from 1 mg to 100 mg, preferably from 1.5 mg to 95 mg, more preferably from 2 mg to 92.5 mg, still more preferably 2.5 mg to 90 mg, still more preferably 3 mg to 87.5 mg, still more preferably 3.5 mg to 85 mg, still more preferably 4 mg to 82.5 mg, still more preferably 4.5 mg to 80 mg, still more preferably 5 mg to 77.5 mg, still more preferably 5.5 mg to 75 mg, 6 mg to 72.5 mg, still more preferably 6.5 mg to 70 mg, still more preferably 7 mg to 65 mg, still more preferably 7.5 mg to 62.5 mg, still more preferably 8 mg to 60 mg, even more preferably from 8.5 mg to 57.5 mg, even more preferably from 9 mg to 55 mg, even more preferably from 9.5 mg to 52.5 mg, even more preferably from 9.75 mg to 52.5 mg, and most preferably from 10 mg to 50 mg.

Furthermore, a mass ratio of the polymeric precipitation inhibitor relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof can range from 0.05 to 10 m/m, preferably from 0.06 to 9.5 m/m, more preferably from 0.07 to 9.00 m/m, still more preferably from 0.08 to 8.50 m/m, still more preferably from 0.09 to 8.00 m/m, still more preferably from 0.1 to 7.5 m/m, still more preferably from 0.11 to 7.25 m/m, still more preferably from 0.12 to 7 m/m, still more preferably from 0.13 to 6.75 m/m, still more preferably from 0.14 to 6.5 m/m, still more preferably from 0.15 to 6.25 m/m, even more preferably from 0.16 to 6 m/m, even more preferably from 0.17 to 5.75 m/m, even more preferably from 0.18 to 5.5 m/m, even more preferably from 0.19 to 5.25 m/m, and most preferably from 0.20 to 5 m/m.

The amount of the binder can vary from 0 wt % to 40 wt %, preferably from 0 wt % to 35 wt %, more preferably from 0 wt % to 30 wt %, still more preferably from 0 wt % to 25 wt %, still more preferably from 0 wt % to 20 wt %, still more preferably from 0 wt % to 15 wt %, still more preferably from 0 wt % to 12 wt %, and most preferably from 0 wt % to 8.5 wt %.

Furthermore, the amount of the binder can range from 1.00 mg to 100 mg, preferably from 1.50 mg to 95 mg, more preferably from 2.00 mg to 92.5 mg, still more preferably 2.50 mg to 90 mg, still more preferably 3.00 mg to 87.5 mg, still more preferably 3.50 mg to 85 mg, still more preferably 4.00 mg to 82.5 mg, still more preferably 4.50 mg to 80 mg, still more preferably 5.00 mg to 77.5 mg, still more preferably 5.50 mg to 75 mg, 6.00 mg to 72.5 mg, still more preferably 6.50 mg to 70 mg, still more preferably 7.00 mg to 65 mg, still more preferably 7.50 mg to 62.5 mg, still more preferably 8.00 mg to 60 mg, even more preferably from 8.50 mg to 57.5 mg, even more preferably from 9.00 mg to 55.0 mg, even more preferably from 9.50 mg to 52.5 mg, even more preferably from 9.75 mg to 52.5 mg, and most preferably from 10 mg to 50 mg.

Furthermore, a mass ratio of the binder relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof can range from 0 to 10 m/m, preferably from 0.05 to 9.5 m/m, more preferably from 0.06 to 9.00 m/m, still more preferably from 0.07 to 8.50 m/m, still more preferably from 0.08 to 8.00 m/m, still more preferably from 0.09 to 7.5 m/m, still more preferably from 0.1 to 7.25 m/m, still more preferably from 0.11 to 7.00 m/m, still more preferably from 0.12 to 6.75 m/m, still more preferably from 0.13 to 6.50 m/m, still more preferably from 0.14 to 6.25 m/m, even more preferably from 0.15 to 6.00 m/m, even more preferably from 0.16 to 5.75 m/m, even more preferably from 0.17 to 5.50 m/m, even more preferably from 0.18 to 5.25 m/m, even more preferably from 0.19 to 5.5 m/m, even more preferably from 0.20 to 5 m/m, even more preferably from 0.20 to 4.5 m/m, even more preferably from 0.20 to 4 m/m, even more preferably from 0.20 to 3.5 m/m, even more preferably from 0.20 to 3 m/m, even more preferably from 0.20 to 2.5 m/m, and even more preferably from 0.20 to 2 m/m.

The amount of the disintegrant can vary from 0.1 wt % to 40 wt %, preferably from 1 wt % to 35 wt %, even more preferably from 2 wt % to 30 wt %, even more preferably from 2.5 wt % to 29 wt %, even more preferably from 3.0 wt % to 28 wt %, even more preferably from 3.5 wt % to 27 wt %, and most preferably from 3.5 wt % to 26.5 wt %.

In addition, the amount of the disintegrant can vary from 0.1 mg to 150 mg, preferably from 0.50 mg to 145 mg, more preferably from 0.75 mg to 140 mg, still more preferably from 1.00 mg to 135 mg, still more preferably from 1.25 mg to 130 mg, still more preferably from 1.50 mg to 125 mg, still more preferably from 1.75 mg to 120 mg, still more preferably from 2.00 mg to 115 mg, still more preferably from 2.25 mg to 110 mg, still more preferably from 2.50 mg to 105 mg, still more preferably from 2.75 mg to 100 mg, still more preferably from 3.00 mg to 95 mg, even more preferably from 3.25 mg to 90 mg, even more preferably from 3.50 mg to 85 mg, even more preferably from 3.75 mg to 80 mg, even more preferably from 4.00 mg to 75 mg, even more preferably from 4.25 mg to 70 mg, even more preferably 4.50 mg to 65 mg, even more preferably 4.75 mg to 60 mg, even more preferably 5.00 mg to 55 mg, even more preferably 5.50 mg to 50 mg, even more preferably 6.00 mg to 45 mg, even more preferably 6.50 mg to 42.5 mg, even more preferably 7.00 mg to 40 mg, even more preferably 7.50 mg to 40 mg, even more preferably 8.00 mg to 40 mg, even more preferably 8.50 mg to 40 mg, even more preferably 9.00 mg to 40 mg, even more preferably 9.50 mg to 40 mg, and most preferably form 10 mg to 40 mg.

Furthermore, a mass ratio of the disintegrant relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof can range from 0.05 to 12 m/m, preferably from 0.06 to 11.5 m/m, more preferably from 0.07 to 11 m/m, still more preferably from 0.08 to 10.5 m/m, still more preferably from 0.09 to 10 m/m, still more preferably from 0.1 to 9.5 m/m, still more preferably from 0.11 to 9 m/m, still more preferably from 0.12 to 8.5 m/m, still more preferably from 0.13 to 8 m/m, still more preferably from 0.14 to 7.5 m/m, still more preferably from 0.15 to 7 m/m, even more preferably from 0.16 to 6.5 m/m, even more preferably from 0.17 to 5.5 m/m, even more preferably from 0.18 to 5 m/m, even more preferably from 0.19 to 5 m/m, and most preferably 0.2 to 5 m/m.

The amount of the lubricant/glidant can range from 0.1 wt % to 10 wt %, preferably from, more preferably from 0.25 wt % to 9.5 wt %, still more preferably from 0.5 wt % to 9 wt %, still more preferably from 0.75 wt % to 8.5 wt %, still more preferably from 1 wt % to 8 wt %, still more preferably from 1.25 wt % to 7.5 wt %, still more preferably from 1.5 wt % to 7 wt %, and even more preferably 1.5 wt % to 6.5 wt %.

Moreover, the amount of the lubricant/glidant can range from 0.01 mg to 100 mg, preferably from 0.05 mg to 95 mg, more preferably from 0.1 mg to 90 mg, still more preferably from 0.3 mg to 85 mg, still more preferably from 0.4 mg to 80 mg, still more preferably from 0.5 mg to 0.6 mg, still more preferably from 0.7 mg to 70 mg, still more preferably from 0.8 mg to 65 mg, still more preferably from 0.9 mg to 60 mg, still more preferably from 1 mg to 55 mg, still more preferably from 1.1 mg to 50 mg, still more preferably from 1.2 mg to 45 mg, still more preferably from 1.3 mg to 40 mg, still more preferably from 1.4 mg to 35 mg, still more preferably from 1.5 mg to 30 mg, still more preferably from 1.6 mg to 25 mg, still more preferably from 1.7 mg to 20 mg, even more preferably from 1.8 mg to 20 mg, even more preferably from 1.9 mg to 20 mg, even preferably from 2 mg to 20 mg, even preferably from 3 mg to 20 mg, even preferably from 4 mg to 20 mg, and most preferably even preferably from 5 mg to 20 mg.

Furthermore, a mass ratio of the lubricant/glidant relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof can range from 0.05 to 2 m/m, preferably from 0.06 to 1.8 m/m, more preferably from 0.07 to 1.6 m/m, 0.08 to 1.4 m/m, still more preferably from 0.09 to 1.3 m/m, and most preferably from 0.1 to 1.2 m/m.

The amount of diluent/filler/binder in the composition can range from 0 wt % to 50% wt %, preferably from 1 wt % to 47.5% wt %, more preferred from 1.5 wt % to 45% wt %, more preferred from 2 wt % to 42.5% wt %, more preferred from 2.5 to 40 wt %, more preferred from 3 wt % to 38% wt %, more preferred 3.5 wt % to 38 wt %, more preferred 4 wt % to 38 wt %, more preferred to wt %, more preferred 4.5 wt % to 38 wt %, and even more preferred 5 wt % to 38 wt %.

Moreover, the amount of the diluent/filler/binder can range from 1 mg to 290 mg, preferably from 2 mg to 280 mg, more preferably from 3 mg to 270 mg, even more preferably from 4 mg to 260 mg, even more preferably from 5 mg to 250 mg, even more preferably from 6 mg to 240 mg, even more preferably from 7 mg to 230 mg, even more preferably from 8 mg to 220 mg, even more preferably from 9 mg to 210 mg, even more preferably from 10 mg to 200 mg, even more preferably from 11 mg to 190 mg, even more preferably from 12 mg to 180 mg, even more preferably from 13 mg to 170 mg, even more preferably from 14 mg to 160 mg, even more preferably from 15 mg to 150 mg, even more preferably from 16 mg to 140 mg, even more preferably from 17 mg to 130 mg, even more preferably from 18 mg to 120 mg, even more preferably from 19 mg to 110 mg, even more preferably from 19 mg to 100 mg, even more preferably from 20 mg to 90 mg, more preferably from 21 mg to 80 mg, even more preferably from 22 mg to 70 mg, even more preferably from 23 mg to 60 mg, even more preferably from 24 mg to 55 mg, and most preferably 25 mg to 50 mg.

Furthermore, a mass ratio of the diluent/filler/binder relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof can range from 0 m/m to 20 m/m, more preferably 0.01 m/m to 17.5 m/m, more preferably 0.05 m/m to 15 m/m, more preferably 0.1 m/m to 0.125 m/m, more preferably 0.15 m/m to 10 m/m, more preferably 0.175 m/m to 7.5 m/m, more preferably 0.2 m/m to 6, more preferably 0.2 m/m to 5.5, more preferably 0.2 m/m to 5 m/m.

The amount of other ingredients can range from 5 wt % to 60 wt %, preferably from 6 wt % to 57.5 wt %, more preferably 7 wt % to 55 wt %, even more preferably from 8 wt % to 52.5 wt %, even more preferably from 9 wt % to 51 wt %, and most preferably 10 wt % to 50 wt % with respect to dosage form.

In addition, the amount of other ingredients can range from 50 mg to 200 mg, preferably from 55 mg to 190 mg, more preferably from 60 mg to 180 mg, still more preferably from 65 mg to 170 mg, still more preferably from 70 mg to 160 mg, still more preferably from 75 mg to 150 mg, still more preferably from 80 mg to 140 mg, still more preferably from 90 mg to 130 mg, even more preferably from 90 mg to 120 mg, even more preferably from 90 mg to 110 mg, and most preferably from 90 mg to 100 mg.

Furthermore, a mass ratio of other ingredients relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof can range from 0 to 30 m/m, preferably from 0.2 to 27.5 m/m, more preferably from 0.3 to 25 m/m, still more preferably from 0.35 to 22.5 m/m, even more preferably from 0.4 to 21 m/m, and most preferably from 0.45 to 20 m/m.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 1 wt % to 75 wt % acidifier.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3 wt % to 75 wt % acidifier.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 4.5 wt % to 55 wt % acidifier.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 1 wt % to 75 wt % acidifier.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3 wt % to 75 wt % acidifier.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 4.5 wt % to 55 wt % acidifier.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 1 wt % to 75 wt % acidifier.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3 wt % to 75 wt % acidifier.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 4.5 wt % to 55 wt % acidifier.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 1 wt % to 75 wt % acidifier.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3 wt % to 75 wt % acidifier.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 4.5 wt % to 55 wt % acidifier.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 1 wt % to 75 wt % adipic acid.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3 wt % to 75 wt % adipic acid.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 4.5 wt % to 55 wt % adipic acid.

A more preferred embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 1 wt % to 75 wt % adipic acid.

A more preferred embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3 wt % to 75 wt % adipic acid.

A more preferred embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 4.5 wt % to 55 wt % adipic acid.

A preferred embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 1 wt % to 75 wt % adipic acid.

A preferred embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3 wt % to 75 wt % adipic acid.

A preferred embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 4.5 wt % to 55 wt % adipic acid.

A preferred embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 1 wt % to 75 wt % adipic acid.

A preferred embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3 wt % to 75 wt % adipic acid.

A preferred embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 4.5 wt % to 55 wt % adipic acid.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 0.1 wt % to 40 wt % polymeric precipitation inhibitor.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 2 wt % to 35 wt % polymeric precipitation inhibitor.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3.5 wt % to 30 wt % polymeric precipitation inhibitor.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 0.1 wt % to 40 wt % polymeric precipitation inhibitor.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3.5 wt % to 35 wt % polymeric precipitation inhibitor.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 2 wt % to 30 wt % polymeric precipitation inhibitor.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 0.1 wt % to 40 wt % polymeric precipitation inhibitor.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 2 wt % to 35 wt % polymeric precipitation inhibitor.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3.5 wt % to 30 wt % polymeric precipitation inhibitor.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 0.1 wt % to 40 wt % polymeric precipitation inhibitor.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 2 wt % to 35 wt % polymeric precipitation inhibitor.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3.5 wt % to 30 wt % polymeric precipitation inhibitor.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 0.1 wt % to 40 wt % L-hydroxypropyl cellulose and/or hydroxypropyl cellulose.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 2 wt % to 35 wt % L-hydroxypropyl cellulose and/or hydroxypropyl cellulose.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3.5 wt % to 30 wt % L-hydroxypropyl cellulose and/or hydroxypropyl cellulose.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 0.1 wt % to 40 wt % L-hydroxypropyl cellulose and/or hydroxypropyl cellulose.

A preferred embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 2 wt % to 35 wt % L-hydroxypropyl cellulose and/or hydroxypropyl cellulose.

A preferred embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3.5 wt % to 30 wt % L-hydroxypropyl cellulose and/or hydroxypropyl cellulose.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 0.1 wt % to 40 wt % L-hydroxypropyl cellulose and/or hydroxypropyl cellulose.

A preferred embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 2 wt % to 35 wt % L-hydroxypropyl cellulose and/or hydroxypropyl cellulose.

A preferred embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3.5 wt % to 30 wt % L-hydroxypropyl cellulose and/or hydroxypropyl cellulose.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 0.1 wt % to 40 wt % L-hydroxypropyl cellulose and/or hydroxypropyl cellulose.

A preferred embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 2 wt % to 35 wt % L-hydroxypropyl cellulose and/or hydroxypropyl cellulose.

A preferred embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 3.5 wt % to 30 wt % L-hydroxypropyl cellulose and/or hydroxypropyl cellulose.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, and 0.1 wt % to 40 wt % polymeric precipitation inhibitor.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, and 2 wt % to 35 wt % polymeric precipitation inhibitor.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, and 3.5 wt % to 30 wt % polymeric precipitation inhibitor.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, and 0.1 wt % to 40 wt % polymeric precipitation inhibitor.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, and 2 wt % to 35 wt % polymeric precipitation inhibitor.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, and 3.5 wt % to 30 wt % polymeric precipitation inhibitor.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, and 0.1 wt % to 40 wt % polymeric precipitation inhibitor.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, and 2 wt % to 35 wt % polymeric precipitation inhibitor.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, and 3.5 wt % to 30 wt % polymeric precipitation inhibitor.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, and 0.1 wt % to 40 wt % polymeric precipitation inhibitor.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, and 2 wt % to 35 wt % polymeric precipitation inhibitor.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, and 3.5 wt % to 30 wt % polymeric precipitation inhibitor.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, and 0.1 wt % to 40 wt % polymeric precipitation inhibitor.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, and 2 wt % to 35 wt % polymeric precipitation inhibitor.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, and 3.5 wt % to 30 wt % polymeric precipitation inhibitor.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, and 0.1 wt % to 40 wt % polymeric precipitation inhibitor.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, and 2 wt % to 35 wt % polymeric precipitation inhibitor.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, and 3.5 wt % to 30 wt % polymeric precipitation inhibitor.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, and 0.1 wt % to 40 wt % polymeric precipitation inhibitor.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, and 2 wt % to 35 wt % polymeric precipitation inhibitor.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, and 3.5 wt % to 30 wt % polymeric precipitation inhibitor.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, and 0.1 wt % to 40 wt % polymeric precipitation inhibitor.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, and 2 wt % to 35 wt % polymeric precipitation inhibitor.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, and 3.5 wt % to 30 wt % polymeric precipitation inhibitor.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, and 0.1 wt % to 40 wt % polymeric precipitation inhibitor.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, and 2 wt % to 35 wt % polymeric precipitation inhibitor.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, and 3.5 wt % to 30 wt % polymeric precipitation inhibitor.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, and 0.1 wt % to 40 wt % polymeric precipitation inhibitor.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, and 2 wt % to 35 wt % polymeric precipitation inhibitor.

An embodiment of the invention is related to a systemic formulation comprising or consisting of 0.1 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, and 3.5 wt % to 30 wt % polymeric precipitation inhibitor.

An embodiment of the invention is related to a systemic formulation comprising or consisting of 0.1 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, and 0.1 wt % to 40 wt % polymeric precipitation inhibitor.

An embodiment of the invention is related to a systemic formulation comprising or consisting of 2.5 wt % to 30.5 wt % (S,E)-methyl-7-(1-(2-(2-ethylbutylamino)-2-oxoethyl)-2- oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, and 2 wt % to 35 wt % polymeric precipitation inhibitor.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, and 3.5 wt % to 30 wt % polymeric precipitation inhibitor.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, and 0.1 wt % to 40 wt % polymeric precipitation inhibitor.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, and 2 wt % to 35 wt % polymeric precipitation inhibitor.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, and 3.5 wt % to 30 wt % polymeric precipitation inhibitor.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 0.1 wt % to 40 wt % L-hydroxypropyl cellulose and/or hydroxypropyl cellulose.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 2 wt % to 35 wt % L-hydroxypropyl cellulose and/or hydroxypropyl cellulose.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 3.5 wt % to 30.5 wt % L-hydroxypropyl cellulose and/or hydroxypropyl cellulose.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 0.1 wt % to 40 wt % L-hydroxypropyl cellulose and/or hydroxypropyl cellulose.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 2 wt % to 35 wt % L-hydroxypropyl cellulose and/or hydroxypropyl cellulose.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 3.5 wt % to 30.5 wt % L-hydroxypropyl cellulose and/or hydroxypropyl cellulose.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 0.1 wt % to 40 wt % L-hydroxypropyl cellulose and/or hydroxypropyl cellulose.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 2 wt % to 35 wt % L-hydroxypropyl cellulose and/or hydroxypropyl cellulose.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 3.5 wt % to 30.5 wt % L-hydroxypropyl cellulose and/or hydroxypropyl cellulose.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 0.1 wt % to 40 wt % L-hydroxypropyl cellulose and/or hydroxypropyl cellulose.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 2 wt % to 35 wt % L-hydroxypropyl cellulose and/or hydroxypropyl cellulose.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 3.5 wt % to 30.5 wt % L-hydroxypropyl cellulose and/or hydroxypropyl cellulose.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 0.1 wt % to 40 wt % L-hydroxypropyl cellulose and/or hydroxypropyl cellulose.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 2 wt % to 35 wt % L-hydroxypropyl cellulose and/or hydroxypropyl cellulose.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 3.5 wt % to 30.5 wt % L-hydroxypropyl cellulose and/or hydroxypropyl cellulose.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 0.1 wt % to 40 wt % L-hydroxypropyl cellulose and/or hydroxypropyl cellulose.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 2 wt % to 35 wt % L-hydroxypropyl cellulose and/or hydroxypropyl cellulose.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 3.5 wt % to 30.5 wt % L-hydroxypropyl cellulose and/or hydroxypropyl cellulose.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 0.1 wt % to 40 wt % L-hydroxypropyl cellulose and/or hydroxypropyl cellulose.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 2 wt % to 35 wt % L-hydroxypropyl cellulose and/or hydroxypropyl cellulose.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 3.5 wt % to 30.5 wt % L-hydroxypropyl cellulose and/or hydroxypropyl cellulose.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 0.1 wt % to 40 wt % L-hydroxypropyl cellulose and/or hydroxypropyl cellulose.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 2 wt % to 35 wt % L-hydroxypropyl cellulose and/or hydroxypropyl cellulose.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 3.5 wt % to 30.5 wt % L-hydroxypropyl cellulose and/or hydroxypropyl cellulose.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 0.1 wt % to 40 wt % L-hydroxypropyl cellulose and/or hydroxypropyl cellulose.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 2 wt % to 35 wt % L-hydroxypropyl cellulose and/or hydroxypropyl cellulose.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 3.5 wt % to 30.5 wt % L-hydroxypropyl cellulose and/or hydroxypropyl cellulose.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 0.1 wt % to 40 wt % L-hydroxypropyl cellulose and/or hydroxypropyl cellulose.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 2 wt % to 35 wt % L-hydroxypropyl cellulose and/or hydroxypropyl cellulose.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 3.5 wt % to 30.5 wt % L-hydroxypropyl cellulose and/or hydroxypropyl cellulose.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 0.1 wt % to 40 wt % L-hydroxypropyl cellulose and/or hydroxypropyl cellulose.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 2 wt % to 35 wt % L-hydroxypropyl cellulose and/or hydroxypropyl cellulose.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, and 3.5 wt % to 30.5 wt % L-hydroxypropyl cellulose and/or hydroxypropyl cellulose.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 0.1 wt % to 40 wt % L-hydroxypropyl cellulose and/or hydroxypropyl cellulose.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 2 wt % to 35 wt % L-hydroxypropyl cellulose and/or hydroxypropyl cellulose.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, and 3.5 wt % to 30.5 wt % L-hydroxypropyl cellulose and/or hydroxypropyl cellulose.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, and 0 wt % to 15 wt % binder.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, and 0 wt % to 12 wt % binder.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 2 wt % to 35 wt % polymeric precipitation inhibitor, and 0 wt % to 12 wt % binder.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, and 0 wt % to 12 wt % binder.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, and 0 wt % to 12 wt % binder.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, and 0 wt % to 12 wt % binder.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, and 0 wt % to 12 wt % binder.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof, 4.5 wt % to 55 wt % acidifier, 0.1 wt % to 40 wt % polymeric precipitation inhibitor, and 0 wt % to 12 wt % binder.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, and 0 wt % to 12 wt % binder.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, and 0 wt % to 12 wt % binder.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, and 0 wt % to 12 wt % binder.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 2 wt % to 35 wt % polymeric precipitation inhibitor, and 0 wt % to 12 wt % binder.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, and 0 wt % to 12 wt % binder.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, and 0 wt % to 12 wt % binder.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, and 0 wt % to 12 wt % binder.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, and 0 wt % to 12 wt % binder.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, and 0 wt % to 12 wt % binder.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, and 0 wt % to 12 wt % binder.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, and 0 wt % to 12 wt % binder.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, and 0 wt % to 12 wt % binder.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 2 wt % to 35 wt % polymeric precipitation inhibitor, and 0 wt % to 12 wt % binder.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, and 0 wt % to 12 wt % binder.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, and 0 wt % to 12 wt % binder.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, and 0 wt % to 12 wt % binder.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, and 0 wt % to 12 wt % binder.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-4-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, and 0 wt % to 12 wt % binder.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, and 0 wt % to 12 wt % binder.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, and 0 wt % to 12 wt % binder.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, and 0 wt % to 12 wt % binder.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 2 wt % to 35 wt % polymeric precipitation inhibitor, and 0 wt % to 12 wt % binder.

An embodiment of the invention is related to a systemic formulation comprising or consisting of 0.1 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, and 0 wt % to 12 wt % binder.

An embodiment of the invention is related to a systemic formulation comprising or consisting of 0.1 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, and 0 wt % to 12 wt % binder.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, and 0 wt % to 12 wt % binder.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, and 0 wt % to 12 wt % binder.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, and 0 wt % to 12 wt % binder.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, and 0 wt % to 12 wt % binder.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, and 0 wt % to 12 wt % binder.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, and 0 wt % to 15 wt % povidone K25.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 2 wt % to 35 wt % L-hydroxypropyl cellulose and/or hydroxypropyl cellulose, and 0 wt % to 12 wt % povidone K25.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, and 0 wt % to 12 wt % povidone K25.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, and 0 wt % to 12 wt % povidone K25.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 2 wt % to 35 wt % L-hydroxypropyl cellulose and/or hydroxypropyl cellulose.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, and 0 wt % to 12 wt % povidone K25.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, and 0 wt % to 12 wt % povidone K25.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 2 wt % to 35 wt % L-hydroxypropyl cellulose and/or hydroxypropyl cellulose, and 0 wt % to 12 wt % povidone K25.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, and 0 wt % to 12 wt % povidone K25.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, and 0 wt % to 12 wt % povidone K25.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 2 wt % to 35 wt % L-hydroxypropyl cellulose and/or hydroxypropyl cellulose, and 0 wt % to 12 wt % povidone K25.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 3.5 wt % to 30.5 wt % L-hydroxypropyl cellulose and/or hydroxypropyl cellulose, and 0 wt % to 12 wt % povidone K25.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, and 0 wt % to 12 wt % povidone K25.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, and 0 wt % to 12 wt % povidone K25.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 15 wt % binder, 0.1 wt % to 35 wt % disintegrant, and 0.1 wt % to 10 wt % lubricant/glidant.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, 2 wt % to 35 wt % disintegrant, and 1 wt % to 9 wt % lubricant/glidant.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, 2 wt % to 35 wt % disintegrant, and 1 wt % to 9 wt % lubricant/glidant.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, 2 wt % to 35 wt % disintegrant, and 1 wt % to 9 wt % lubricant/glidant.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of 0.1 wt % to 45 wt % (S,E)-methyl-7-(1-(2-(2-ethylbuylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof, 1 wt % to 75 wt % acidifier, 3.5 wt % to 30 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

A preferred embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof, 3 wt % to 75 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

A very preferred embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof, 3 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of 0.1 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, and 0 wt % to 12 wt % binder.

An embodiment of the invention is related to a systemic formulation comprising or consisting of 0.1 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, 0 wt % to 15 wt % povidone K25, 0.1 wt % to 35 wt % sodium croscarmellose, and 0.1 wt % to 10 wt % talc or silicon dioxide.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of (S,E)-methyl-7-(1-(2-(2-ethylbutylamino)-2-oxoethyl)-2-oxo-1,2-dihydropyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 2 wt % to 35 wt % L-hydroxypropyl cellulose and/or hydroxypropyl cellulose, 2 wt % to 35 wt % sodium croscarmellose, and 1 wt % to 9 wt % talc or silicon dioxide.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, and 0 wt % to 12 wt % povidone K25.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 2 wt % to 35 wt % L-hydroxypropyl cellulose and/or hydroxypropyl cellulose, and 0 wt % to 12 wt % povidone K25.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 3.5 wt % to 30.5 wt % L-hydroxypropyl cellulose and/or hydroxypropyl cellulose, and 0 wt % to 12 wt % povidone K25.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, and 3.5 wt % to 30.5 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 15 wt % binder, 0.1 wt % to 35 wt % disintegrant, 0.1 wt % to 10 wt % lubricant/glidant, and 0 wt % to 50 wt % diluent/filler/binder.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept enoate or an enantiomer, a solvate, a hydrate or a pharmaceutically acceptable salt thereof, 1 wt % to 75 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, or hydrate or a pharmaceutically acceptable salt thereof, 1 wt % to 75 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 0.1 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 3.5 wt % to 30 wt % polymeric precipitation inhibitor, 0 wt % to 12 wt % binder, and 0 wt % to 50 wt % diluent/filler/binder.

An embodiment of the invention is related to a systemic formulation comprising or consisting of 0.1 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0.1 wt % to 40 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 2 wt % to 35 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 3.5 wt % to 30 wt % polymeric precipitation inhibitor, 0 wt % to 12 wt % binder, 2 wt % to 35 wt % disintegrant, 1 wt % to 9 wt % lubricant/glidant, and 0 wt % to 50 wt % diluent/filler/binder.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, 0 wt % to 15 wt % povidone K25, 0.1 wt % to 35 wt % sodium croscarmellose, 0.1 wt % to 10 wt % talc or silicon dioxide, and 0 wt % to 50 wt % mannitol and/or microcrystalline cellulose.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt %

L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of (S,E)-methyl-7-(1-(2-(2-ethylbutylamino)-2-oxoethyl)-2-oxo-1,2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose, and 0 wt % to 50 wt % mannitol and/or microcrystalline cellulose.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 2 wt % to 35 wt % L-hydroxypropyl cellulose and/or hydroxypropyl cellulose, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 2 wt % to 35 wt % L-hydroxypropyl cellulose and/or hydroxypropyl cellulose, 0 wt % to 12 wt % povidone K25, 1 wt % to 9 wt % talc or silicon dioxide, and 0 wt % to 50 wt % mannitol and/or microcrystalline cellulose.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 2.5 wt % to 30.5 wt % (S,E)-methyl-7-(1-(2-(2-ethylbutylamino)-2-oxoethyl)-2- oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 0.1 wt % to 40 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % adipic acid, 3.5 wt % to 30.5 wt % L-hydroxypropyl cellulose and/or hydroxypropyl cellulose, 0 wt % to 12 wt % povidone K25, 2 wt % to 35 wt % sodium croscarmellose, 1 wt % to 9 wt % talc or silicon dioxide, and 0 wt % to 50 wt % mannitol and/or microcrystalline cellulose.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0 to 50 wt % diluent/filler/binder, 0.1 wt % to 40 wt % polymeric precipitation inhibitor, 0 wt % to 15 wt % binder, 0.1 wt % to 35 wt % disintegrant, and 0.1 wt % to 10 wt % lubricant/glidant.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 wt % to 75 wt % acidifier, 0 to 50 wt % diluent/filler/binder, 0.1 wt % to 40 wt % polymeric precipitation inhibitor, 0 wt % to 12 wt % binder, 2 wt % to 35 wt % disintegrant, and 1 wt % to 9 wt % lubricant/glidant.

A more preferred embodiment according to the invention is directed to a systemic formulation comprising or consisting of 0.1 wt % to 35 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0 wt % to 50 wt % diluent/filler/binder, 1 wt % to 75 wt % acidifier, 2 wt % to 25 wt % polymeric precipitation inhibitor, 0 wt % to 12 wt % binder, 2 wt % to 35 wt % disintegrant, and 1 wt % to 9 wt % lubricant/glidant.

A more preferred embodiment according to the invention is directed to a systemic formulation comprising or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0 wt % to 50 wt % diluent/filler/binder, 1 wt % to 75 wt % acidifier, 2 wt % to 25 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 3 wt % to 75 wt % acidifier, 0 to 50 wt % diluent/filler/binder, 0.1 wt % to 40 wt % polymeric precipitation inhibitor, 0 wt % to 12 wt % binder, 2 wt % to 35 wt % disintegrant, and 1 wt % to 9 wt % lubricant/glidant.

A more preferred embodiment according to the invention is directed to a systemic formulation comprising or consisting of or consisting of 0.1 wt % to 35 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0 wt % to 50 wt % diluent/filler/binder, 3 wt % to 75 wt % acidifier, 2 wt % to 25 wt % polymeric precipitation inhibitor, 0 wt % to 12 wt % binder, 2 wt % to 35 wt % disintegrant, and 1 wt % to 9 wt % lubricant/glidant.

A more preferred embodiment according to the invention is directed to a systemic formulation comprising or consisting of or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0 wt % to 50 wt % diluent/filler/binder, 3 wt % to 75 wt % acidifier, 2 wt % to 25 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 4.5 wt % to 55 wt % acidifier, 0 to 50 wt % diluent/filler/binder, 0.1 wt % to 40 wt % polymeric precipitation inhibitor, 0 wt % to 12 wt % binder, 2 wt % to 35 wt % disintegrant, and 1 wt % to 9 wt % lubricant/glidant.

A more preferred embodiment according to the invention is directed to a systemic formulation comprising or consisting of or consisting of 0.1 wt % to 35 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0 wt % to 50 wt % diluent/filler/binder, 4.5 wt % to 55 wt % acidifier, 2 wt % to 25 wt % polymeric precipitation inhibitor, 0 wt % to 12 wt % binder, 2 wt % to 35 wt % disintegrant, and 1 wt % to 9 wt % lubricant/glidant.

A more preferred embodiment according to the invention is directed to a systemic formulation comprising or consisting of or consisting of 2.5 wt % to 30.5 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0 wt % to 50 wt % diluent/filler/binder, 4.5 wt % to 55 wt % acidifier, 2 wt % to 25 wt % polymeric precipitation inhibitor, 0 wt % to 12 wt % binder, 2 wt % to 35 wt % disintegrant, and 1 wt % to 9 wt % lubricant/glidant.

An embodiment of the invention is related to a systemic formulation comprising or consisting of or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0 to 50 wt % microcrystalline cellulose, 5 wt % to 75 wt % adipic acid, 0.1 wt % to 40 wt % L-hydroxypropyl cellulose and/or hydroxypropyl cellulose, 0 wt % to 15 wt % povidone K25, 0.1 wt % to 35 wt % sodium croscarmellose, and 0.1 wt % to 9 wt % talc or silicon dioxide.

An embodiment of the invention is related to a systemic formulation comprising or consisting of 0.1 wt % to 80 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0 to 50 wt % microcrystalline cellulose, 1 wt % to 75 wt % adipic acid, 0.1 wt % to 40 wt % L-hydroxypropyl cellulose and/or hydroxypropyl cellulose, 0 wt % to 15 wt % povidone K25, 2 wt % to 35 wt % sodium croscarmellose, and 1 wt % to 9 wt % talc or silicon dioxide.

A more preferred embodiment according to the invention is directed to a systemic formulation comprising or consisting of 0.1 wt % to 35 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0 to 50 wt % microcrystalline cellulose, 1 wt % to 75 wt % adipic acid, 0.1 wt % to 40 wt % L-hydroxypropyl cellulose and/or hydroxypropyl cellulose, 0 wt % to 15 wt % povidone K25, 2 wt % to 35 wt % sodium croscarmellose, and 1 wt % to 9 wt % talc or silicon dioxide.

If the systemic formulation is discloses as a formulation consisting of ingredients in certain amounts (weight percent, mass ratio and/or absolute mass), the rest are other ingredients, i.e. it is balanced to 100 wt % with other ingredients. The other ingredients are described above.

An embodiment of the invention is related to a systemic formulation for use in the prophylaxis and/or treatment of the diseases disclosed herein comprising or consisting of at least 0.01 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 mg to 500 mg adipic acid, and 1 mg to 100 mg L-hydroxypropyl cellulose.

A preferred embodiment of the invention is related to a systemic formulation comprising or consisting of 0.01 mg to 500 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 mg to 500 mg adipic acid, and 1 mg to 100 mg L-hydroxypropyl cellulose and/or hydroxypropyl cellulose, and up to 100 mg povidone K25.

An embodiment of the invention is related to a systemic formulation comprising or consisting of 0.01 mg to 500 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 mg to 500 mg adipic acid, 1 mg to 100 mg L-hydroxypropyl cellulose and hydroxypropyl cellulose, up to 100 mg povidone K25, 1 mg to 100 mg sodium croscarmellose, and 1 mg to 50 mg talc or silicon dioxide.

An embodiment of the invention is related to a systemic formulation comprising or consisting of 0.01 mg to 500 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 mg to 360 mg adipic acid, 10 mg to 40 mg L-hydroxypropyl cellulose, 10 mg to 40 mg sodium croscarmellose, and 1 mg to 20 mg talc or silicon dioxide.

An embodiment of the invention is related to a systemic formulation comprising or consisting of at least 0.1 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 mg to 500 mg adipic acid, and 1 mg to 100 mg L-hydroxypropyl cellulose.

A preferred embodiment of the invention is related to a systemic formulation comprising or consisting of 0.1 mg to 500 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 mg to 500 mg adipic acid, and 1 mg to 100 mg L-hydroxypropyl cellulose and/or hydroxypropyl cellulose, and up to 100 mg povidone K25.

An embodiment of the invention is related to a systemic formulation comprising or consisting of 0.1 mg to 500 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 mg to 500 mg adipic acid, 1 mg to 100 mg L-hydroxypropyl cellulose and hydroxypropyl cellulose, up to 100 mg povidone K25, 1 mg to 100 mg sodium croscarmellose, and 1 mg to 50 mg talc or silicon dioxide.

An embodiment of the invention is related to a systemic formulation comprising or consisting of 0.1 mg to 500 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 mg to 360 mg adipic acid, 10 mg to 40 mg L-hydroxypropyl cellulose, 10 mg to 40 mg sodium croscarmellose, and 1 mg to 20 mg talc or silicon dioxide.

A preferred embodiment of the invention is related to a systemic formulation comprising or consisting of 0.5 mg to 500 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 mg to 500 mg adipic acid, and 1 mg to 100 mg L-hydroxypropyl cellulose and/or hydroxypropyl cellulose, and up to 100 mg povidone K25.

An embodiment of the invention is related to a systemic formulation comprising or consisting of 0.5 mg to 500 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 mg to 500 mg adipic acid, 1 mg to 100 mg L-hydroxypropyl cellulose and hydroxypropyl cellulose, up to 100 mg povidone K25, 1 mg to 100 mg sodium croscarmellose, and 1 mg to 50 mg talc or silicon dioxide.

An embodiment of the invention is related to a systemic formulation comprising or consisting of 0.5 mg to 500 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 mg to 360 mg adipic acid, 10 mg to 40 mg L-hydroxypropyl cellulose, 10 mg to 40 mg sodium croscarmellose, and 1 mg to 20 mg talc or silicon dioxide.

A preferred embodiment of the invention is related to a systemic formulation comprising or consisting of 1 mg to 500 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 mg to 500 mg adipic acid, and 1 mg to 100 mg L-hydroxypropyl cellulose and/or hydroxypropyl cellulose, and up to 100 mg povidone K25.

An embodiment of the invention is related to a systemic formulation comprising or consisting of 1 mg to 500 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 mg to 500 mg adipic acid, 1 mg to 100 mg L-hydroxypropyl cellulose and hydroxypropyl cellulose, up to 100 mg povidone K25, 1 mg to 100 mg sodium croscarmellose, and 1 mg to 50 mg talc or silicon dioxide.

An embodiment of the invention is related to a systemic formulation comprising or consisting of 1 mg to 500 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 mg to 360 mg adipic acid, 10 mg to 40 mg L-hydroxypropyl cellulose, 10 mg to 40 mg sodium croscarmellose, and 1 mg to 20 mg talc or silicon dioxide.

An embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 1 to 15 m/m acidifier, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 11.5 to 1.5 m/m acidifier, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 11.5 to 1.8 m/m acidifier, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 0.1 to 7 m/m polymeric precipitation inhibitor, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and 0.2 to 5 m/m polymeric precipitation inhibitor, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 to 15 m/m acidifier, and 0.1 to 7 m/m polymeric precipitation inhibitor, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.5 m/m acidifier, and 0.1 to 7 m/m polymeric precipitation inhibitor, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m acidifier, and 0.1 to 7 m/m polymeric precipitation inhibitor, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 to 15 m/m acidifier, and 0.2 to 5 m/m polymeric precipitation inhibitor, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.5 m/m acidifier, and 0.2 to 5 m/m polymeric precipitation inhibitor, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m acidifier, and 0.2 to 5 m/m polymeric precipitation inhibitor, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 to 15 m/m acidifier, 0.1 to 7 m/m polymeric precipitation inhibitor, 0 to 5 m/m binder, 0.1 to 7 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2- dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.5 m/m acidifier, 0.1 to 7 m/m polymeric precipitation inhibitor, 0 to 5 m/m binder, 0.1 to 7 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m acidifier, 0.1 to 7 m/m polymeric precipitation inhibitor, 0 to 5 m/m binder, 0.1 to 7 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 to 15 m/m acidifier, 0.2 to 5 m/m polymeric precipitation inhibitor, 0 to 5 m/m binder, 0.1 to 7 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.5 m/m acidifier, 0.2 to 5 m/m polymeric precipitation inhibitor, 0 to 5 m/m binder, 0.1 to 7 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m acidifier, 0.2 to 5 m/m polymeric precipitation inhibitor, 0 to 5 m/m binder, 0.1 to 7 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 to 15 m/m acidifier, 0.1 to 7 m/m polymeric precipitation inhibitor, 0 to 2 m/m binder, 0.1 to 7 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxo-ethyl)-2-oxo-1,2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.5 m/m acidifier, 0.1 to 7 m/m polymeric precipitation inhibitor, 0 to 2 m/m binder, 0.1 to 7 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m acidifier, 0.1 to 7 m/m polymeric precipitation inhibitor, 0 to 2 m/m binder, 0.1 to 7 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 to 15 m/m acidifier, 0.1 to 7 m/m polymeric precipitation inhibitor, 0 to 5 m/m binder, 0.1 to 7 m/m disintegrant, and 0.1 to 1.5 m/m lubricant/glidant, wherein m/m (mass ratio) of said compounds is calculated relative to mass of (S,E)-methyl-7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5- carboxamido)-7-oxohept-2-enoate or an enantiomer, a solvate, hydrate or a pharmaceutically acceptable salt thereof, 11.5 to 1.5 m/m acidifier, 0.1 to 7 m/m polymeric precipitation inhibitor, 0 to 5 m/m binder, 0.1 to 7 m/m disintegrant, and 0.1 to 1.5 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m acidifier, 0.1 to 7 m/m polymeric precipitation inhibitor, 0 to 5 m/m binder, 0.1 to 7 m/m disintegrant, and 0.1 to 1.5 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 to 15 m/m acidifier, 0.1 to 7 m/m polymeric precipitation inhibitor, 0 to 5 m/m binder, 0.2 to 5 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.5 m/m acidifier, 0.1 to 7 m/m polymeric precipitation inhibitor, 0 to 5 m/m binder, 0.2 to 5 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m acidifier, 0.1 to 7 m/m polymeric precipitation inhibitor, 0 to 5 m/m binder, 0.2 to 5 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 to 15 m/m acidifier, 0.1 to 7 m/m polymeric precipitation inhibitor, 0 to 5 m/m binder, 0.1 to 7 m/m disintegrant, 0.05 to 2 m/m lubricant/glidant, 0 to 5 m/m diluent/filler/binder, and 0 m/m to 25 m/m other ingredients, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m acidifier, 0.2 to 5 m/m polymeric precipitation inhibitor, 0 to 2 m/m binder, 0.2 to 5 m/m disintegrant, and 0.05 to 2 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m acidifier, 0.2 to 5 m/m polymeric precipitation inhibitor, 0 to 2 m/m binder, 0.2 to 5 m/m disintegrant, 0.05 to 2 m/m lubricant/glidant, and 0 to 5 m/m diluent/filler/binder, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m acidifier, 0.2 to 5 m/m polymeric precipitation inhibitor, 0 to 2 m/m binder, 0.2 to 5 m/m disintegrant, 0.05 to 2 m/m lubricant/glidant, 0 to 5 m/m diluent/filler/binder, and 0 m/m to 19.5 m/m other ingredients, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A particularly preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m acidifier, 0.2 to 5 m/m polymeric precipitation inhibitor, 11.5 to 1.5 m/m binder, 0.2 to 5 m/m disintegrant, and 0.1 to 1.5 m/m lubricant/glidant, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

Another preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 to 15 m/m adipic acid, and 0.1 to 7 m/m L-hydroxypropyl cellulose and/or hydroxypropyl cellulose, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

Another particularly preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m adipic acid, and 0.2 to 5 m/m L-hydroxypropyl cellulose and/or hydroxypropyl cellulose, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

Another preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 1 to 15 m/m adipic acid, 0.1 to 7 m/m L-hydroxypropyl cellulose and/or hydroxypropyl cellulose, 0 to 2 m/m povidone K25, 0.2 to 5 m/m sodium croscarmellose, and 0.05 to 2 m/m talc or silicon dioxide, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

Another particularly preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 11.5 to 1.8 m/m adipic acid, 0.2 to 5 m/m L-hydroxypropyl cellulose and/or hydroxypropyl cellulose, 0 to 1.5 m/m povidone K25, 0.2 to 5 m/m sodium croscarmellose, and 0.1 to 1.2 m/m talc or silicon dioxide, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof.

A mass ratio of the acidifier relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof ranges from 11.5 to 1 m/m, and a mass ratio of the polymeric precipitation inhibitor relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof ranges from 0.2 to 5 m/m is preferred.

More preferred is a mass ratio of the acidifier relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof ranges from 11.5 to 1.8 m/m, and a mass ratio of the polymeric precipitation inhibitor relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof ranges from 0.2 to 5 m/m.

A mass ratio between the acidifier and the polymeric precipitation inhibitor can vary from 0.01 m/m to 20 m/m, preferably from 0.02 m/m to 15 m/m, more preferably from 0.03 m/m to 12.5 m/m, even more preferably from 0.04 m/m to 10 m/m, even more preferably from 0.05 m/m, even more preferably from 0.06 m/m to 9 m/m, even more preferably from 0.07 m/m to 8 m/m, even more preferably from 0.08 m/m to 7 m/m, even more preferably from 0.09 m/m to 6 m/m, even more preferably from 0.1 m/m to 5 m/m, even more preferably from 0.1 m/m to 4.5 m/m, even more preferably from 0.1 m/m to 4 m/m, even more preferably from 0.1 m/m to 3.5 m/m, and most preferably from 0.1 m/m to 3 m/m, wherein the mass ration is calculated relative to the mass of the acidifier in the formulation.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, acidifier, and polymeric precipitation inhibitor, wherein the mass ratio between the solution stabilizer and the acidifier ranges from 0.01 to 6 m/m, and wherein m/m (mass ratio) of said compounds is calculated relative to the mass of the acidifier.

Preferably, the formulation according to the invention is not included in a pump which is implantable. The administration by an osmotic pump is not applicable to human.

A preferred embodiment of the invention is related to a systemic formulation comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, acidifier, and polymeric precipitation inhibitor, wherein the mass ratio between the solution stabilizer and the acidifier ranges from 0.05 to 3.5 m/m, and wherein m/m (mass ratio) of said compounds is calculated relative to the mass of the acidifier.

Preferably, the formulation according to the invention is not included in a pump which is implantable. The administration by an osmotic pump is not applicable to human.

Preferably, the maximal concentration in the plasma or tissue (Cmax-value) of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof after administration is 0.2 ng/mL to 2000 ng/mL, and wherein the Cmax-value is measured in plasma samples by liquid chromatography coupled with mass spectrometry.

The inhibitory effect is dependent from the maximal plasma or tissue concentration (cmax-value).

Another aspect of the invention is directed to a formulation according to the invention for use as a medicine preferably in mammal, and most preferably in human.

A preferred embodiment of the invention is related to a systemic formulation for use in the prophylaxis and/or treatment, wherein the TG2-related diseases. Preferably the TG2-related diseases are selected from the group comprising or consisting of nephropathy, fibrotic liver diseases including NAFLD, NASH, cirrhosis, cholestatic liver diseases such as primary sclerosing cholangitis (PSC), and primary biliary cholangitis (PBC), autoimmune hepatitis (AIH), alcoholic steatohepatitis (ASH), cystic fibrosis, pulmonary fibrosis, idiopathic pulmonary fibrosis, radiation-induced lung injury, bridging fibrosis, cardiac fibrosis, systemic sclerosis, collagen induced arthritis (CIA), rheumatoid arthritis (RA), atrial fibrosis, endomyocardial fibrosis, old myocardial infarction, vascular stiffening, vascular calcification, fibroproliferative diseases, elevated blood pressure, gliar scar, arterial stiffness, arthrofibrosis, Dupuytren's contracture, keloid, mediastinal fibrosis, myelofibrosis, Peyronie's disease, nephrogenic systemic fibrosis, IgA nephropathy, progressive massive fibrosis, retroperitoneal fibrosis, systemic sclerosis, and adhesive capsulitis preferably in human. Most preferably the TG2-related disease is selected from nephropathy, NASH, cystic fibrosis, and diabetes related fibrosis.

A more preferred embodiment of the invention is related to a systemic formulation for use in the prophylaxis and/or treatment, wherein the TG2-related disease is selected from the group comprising or consisting of nephropathy, fibrotic liver diseases including NAFLD, NASH, cirrhosis, cholestatic liver diseases such as primary sclerosing cholangitis (PSC), and primary biliary cholangitis (PBC), autoimmune hepatitis (AIH), alcoholic steatohepatitis (ASH) and/or cystic fibrosis, pulmonary fibrosis, idiopathic pulmonary fibrosis, cardiac fibrosis, systemic sclerosis, collagen induced arthritis (CIA), rheumatoid arthritis (RA), IgA nephropathy (IgA-N), vascular stiffening, vascular calcification, fibroproliferative diseases, and elevated blood pressure preferably in human.

A preferred embodiment according to the invention is related to a systemic formulation for use in the prophylaxis and/or in the treatment of fibrosis preferably in human.

Thus, a further aspect of the invention is related to a compound of formula (I) for use in the prophylaxis and/or in the treatment of fibrosis preferably in human.

Another aspect of the invention is related to a salt of compound of formula (I) for use in the prophylaxis and/or in the treatment of fibrosis preferably in human. Still another aspect of the invention is related to a salt of compound of formula (I) and adipic acid for use in the prophylaxis and/or in the treatment of fibrosis preferably in human.

The fibrosis is more preferably related to fibrotic changes in context of a diabetic condition. An especially preferred embodiment of the invention is thus directed to a formulation preferably systemic formulation, more preferably enteral formulation, and most preferably an oral formulation according to the invention for the prophylaxis and/or treatment of diabetic nephropathy, diabetic associated non-alcoholic steatohepatitis and/or cystic fibrosis related diabetes. Thus, in a preferred embodiment of the invention the TG2-related disease is selected from the group consisting of nephropathy, NASH and/or cystic fibrosis. In a further preferred embodiment of the invention, the TG2-related disease comprises or consist of diabetes related fibrosis.

An embodiment of the invention is related to a formulation according to the invention for use in the prophylaxis and/or treatment of a disease selected from the group comprising or consisting of nephropathy, NASH and/or cystic fibrosis.

Another aspect of the invention is directed to a method for preparation of a formulation according to the invention comprising the step:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

The amount of (5, E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof provided in step A-1) is mentioned above.

Thus, an embodiment of the invention is directed to a method for preparation of a formulation according to the invention comprising the step:

A-1) Providing 1 mg to 500 g (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

Thus, an embodiment of the invention is directed to a method for preparation of a formulation according to the invention comprising the step:

A-1) Providing 1 mg to 500 g (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

Another embodiment of the invention is directed to a method for preparation of a formulation according to the invention comprising the step:

A-1) Providing 0.1 wt % to 80 wt % (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof.

It is apparent that the amount of the drug can also be substitute by another amount as mentioned above.

In step A-2), at least one excipient, as described herein, is added. Preferably, at least one excipient is a polymeric precipitation inhibitor preferably L-hydroxypropyl cellulose, a disintegrant or a diluent/filler/binder.

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2) adding at least one excipient.

In a step A-2'), the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, a polymeric precipitation inhibitor preferably L-hydroxypropyl cellulose and a disintegrant preferably sodium croscarmellose are sieved in a dry state preferably separately.

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole carboxamido)-7-oxohept-2-enoate or an enantiomer, a solvate, a hydrate or a pharmaceutically acceptable salt thereof, and A-2') Sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, a polymeric precipitation inhibitor and a disintegrant in a dry state, preferably separately.

The amount of the disintegrant, polymeric precipitation inhibitor and disintegrant in step A-2') is mentioned above.

Thus, an embodiment according to the invention is related to a method for preparation of a formulation according to the invention comprising the steps:

A-1) Providing 1 mg to 500 mg (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') Sieving the (5,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 10 mg to 50 mg polymeric precipitation inhibitor and 10 mg to 40 mg disintegrant in a dry state, preferably separately.

A preferred embodiment according to the invention is related to a method for preparation of a formulation according to the invention comprising the steps:

A-1) Providing 1 mg to 500 mg (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') Sieving the (5,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 10 mg to 50 mg L-hydroxypropyl cellulose and 10 mg to 40 mg sodium croscarmellose in a dry state, preferably separately.

Another preferred embodiment according to the invention is related to a method for preparation of a formulation according to the invention comprising the steps:

A-1) Providing 0.1 wt % to 80 wt % (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') Sieving the (5,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0.1 wt % to 40 wt % polymeric precipitation inhibitor and 2 wt % to 15 wt % disintegrant in a dry state, preferably separately.

Another more preferred embodiment according to the invention is related to a method for preparation of a formulation according to the invention comprising the steps:

A-1) Providing 0.1 wt % to 80 wt % (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof, and A-2') Sieving the (5,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0.1 wt % to 40 wt % L-hydroxypropyl cellulose and/povidone K25 and 2 wt % to 15 wt % sodium croscarmellose in a dry state, preferably separately.

It is apparent that the amount of the excipients and the drug can also be substitute by another amount as mentioned above.

In a step A-3), a solvent can be added which leads to a particle agglomeration and the formation of the granule structure. Preferably, the solvent is ethanol.

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, A-2) adding at least one excipient, and A-3) adding a solvent which leads to a particle agglomeration and the formation of the granule structure.

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-

7-oxohept-2-enoate or an enantiomer, a solvate, a hydrate or a pharmaceutically acceptable salt thereof, a polymeric precipitation inhibitor and a disintegrant in a dry state, and A-3) adding a solvent which leads to a particle agglomeration and the formation of the granule structure.

In a step A-4), the granule mass can be sieved in a wet state preferably the granule mass of step A-3).

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, a polymeric precipitation inhibitor and a disintegrant in a dry state, A-3) adding a solvent which leads to a particle agglomeration and the formation of the granule structure, and A-4) sieving the granule mass of step A-3) in a wet state.

In a step A-5), a granule mass in a wet state is dried, wherein dry granules are received.

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, a polymeric precipitation inhibitor and a disintegrant in a dry state, A-3) adding a solvent which leads to a particle agglomeration and the formation of the granulate structure, A-4) sieving the granulate mass of step A-3) in a wet state, and A-5) drying the granule mass in a wet state.

In a step B-1), an excipient preferably adipic acid and/or talc can be added to the dry granule, and mixed preferably in a dry mixer forming a powder mixture.

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and B-1) adding at least one excipient.

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, A-2) adding at least one excipient, and A-3) adding a solvent which leads to a particle agglomeration and the formation of the granule structure.

B-1) adding at least one excipient.

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, a polymeric precipitation inhibitor and a disintegrant in a dry state, A-3) adding a solvent which leads to a particle agglomeration and the formation of the granulate structure, A-4) sieving the granulate mass of step A-3) in a wet state, A-5) drying the granule mass in a wet state, and B-1) adding at least one excipient such as an acidifier preferably adipic acid and/or a lubricant/glidant preferably talc or silicon dioxide to the dry granule.

Thus, an embodiment according to the invention is related to a method for preparation of a formulation according to the invention comprising the steps:

A-1) Providing 1 mg to 500 mg (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, hydrate or a pharmaceutically acceptable salt thereof, 10 mg to 50 mg polymeric precipitation inhibitor and 10 mg to 40 mg disintegrant in a dry state, A-3) adding a solvent which leads to a particle agglomeration and the formation of the granulate structure, A-4) sieving the granulate mass of step A-3) in a wet state, A-5) drying the granule mass in a wet state, and B-1) adding 10 to 360 mg acidifier and/or 1 mg to 20 mg lubricant/glidant preferably talc or silicon dioxide to the dry granule.

Thus, an embodiment according to the invention is related to a method for preparation of a formulation according to the invention comprising the steps:

A-1) Providing 0.1 wt % to 80 wt % (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-

7-oxohept-2-enoate or an enantiomer, a solvate, hydrate or a pharmaceutically acceptable salt thereof, 0.1 wt % to 40 wt % polymeric precipitation inhibitor and 2 wt % to 15 wt % disintegrant in a dry state, A-3) adding a solvent which leads to a particle agglomeration and the formation of the granulate structure, A-4) sieving the granulate mass of step A-3) in a wet state, A-5) drying the granule mass in a wet state, and B-1) adding 5 wt % to 75 wt % acidifier and/or 0.1 wt % to 10 wt % lubricant/glidant preferably talc or silicon dioxide to the dry granule.

A preferred embodiment according to the invention is related to a method for preparation of a formulation according to the invention comprising the steps:

A-1) Providing 1 mg to 500 mg (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 10 mg to 50 mg L-hydroxypropyl cellulose and/or povidone K25 and 10 mg to 40 mg sodium croscarmellose are sieved in a dry state preferably separately.

A-3) adding a solvent which leads to a particle agglomeration and the formation of the granulate structure, A-4) sieving the granulate mass of step A-3) in a wet state, A-5) drying the granule mass in a wet state, and B-1) adding 10 to 360 mg adipic acid and 1 mg to 20 mg talc or silicon dioxide to the dry granule.

A further more preferred embodiment according to the invention is related to a method for preparation of a formulation according to the invention comprising the steps:

A-1) Providing 0.1 wt % to 80 wt % (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0.1 wt % to 40 wt % L-hydroxypropyl cellulose and/or povidone K25 and 2 wt % to 15 wt % sodium croscarmellose are sieved in a dry state preferably separately.

A-3) adding a solvent which leads to a particle agglomeration and the formation of the granulate structure, A-4) sieving the granulate mass of step A-3) in a wet state, A-5) drying the granule mass in a wet state, and B-1) adding 5 wt % to 75 wt % adipic acid and 0.1 wt % to 10 wt % talc or silicon dioxide to the dry granule.

In a step B-1'), the excipient acidifier and/or lubricant/glidant preferably can be sieved preferably separately if two excipients are sieved.

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, a polymeric precipitation inhibitor and a disintegrant in a dry state, A-3) adding a solvent which leads to a particle agglomeration and the formation of the granulate structure, A-4) sieving the granulate mass of step A-3) in a wet state, A-5) drying the granule mass in a wet state, B-1') sieving an acidifier and a lubricant/glidant such as talc or silicon dioxide, and B-1) adding the sieved acidifier and lubricant/glidant to the dry granulate.

A preferred embodiment according to the invention is related to a method for preparation of a formulation according to the invention comprising the steps:

A-1) Providing compound 1 mg to 500 mg (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 10 mg to 50 mg polymeric precipitation inhibitor and 10 mg to 40 mg disintegrant in a dry state, A-3) adding a solvent which leads to a particle agglomeration and the formation of the granulate structure, A-4) sieving the granulate mass of step A-3) in a wet state, A-5) drying the granule mass in a wet state, B-1') sieving 10 to 360 mg acidifier and 1 mg to 20 mg lubricant/glidant such as talc or silicon dioxide, and B-1) adding the sieved acidifier and lubricant/glidant to the dry granulate.

Another preferred embodiment according to the invention is related to a method for preparation of a formulation according to the invention comprising the steps:

A-1) Providing compound 0.1 wt % to 80 wt % (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, 0.1 wt % to 40 wt % polymeric precipitation inhibitor and 2 wt % to 15 wt % disintegrant in a dry state, A-3) adding a solvent which leads to a particle agglomeration and the formation of the granulate structure, A-4) sieving the granulate mass of step A-3) in a wet state, A-5) drying the granule mass in a wet state, B-1') sieving 1 wt % to 75 wt % acidifier and 0.1 wt % to 10 wt % lubricant/glidant such as talc or silicon dioxide, and B-1) adding the sieved acidifier and lubricant/glidant to the dry granulate.

In a step C-1), the formulation in different dosage forms can be obtained by filling the powder mixture of step B-1) in hard gelatine capsule or by pressing the powder mixture or granule to a tablet. The powder mixture or granules are already dosage forms. In step, C-1), also a solution suitable for a parententeral admiration e.g. intravenous can be achieved if a solvent is added in step B-1) as an excipient. Also a formulation for the parenteral administration in solid form which is used for the preparation of solution before the administration is conceivable.

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, B-1) adding an excipient, and C-1) obtaining the systemic formulation.

Thus, an embodiment according to the invention is related to a method for preparation of a formulation according to the invention comprising the steps:

A-1) Providing (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and A-2') sieving the (S,E)-methyl 7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, a polymeric precipitation inhibitor and a disintegrant in a dry state, A-3) adding a solvent which leads to a particle agglomeration and the formation of the granulate structure, A-4) sieving the granulate mass of step A-3) in a wet state A-5) drying the granule mass in a wet state, B-1) adding adipic acid and talc to the dry granulate, and C-1) obtaining the systemic formulation by filling the powder mixture of step B-1) in hard gelatine capsule or by pressing the granule or powder mixture to a tablet.

Use of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate as hepatoprotectant Further, the present application relates also to the use of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, an enantiomer, a solvate, a hydrate or a pharmaceutically acceptable salt thereof as a hepatoprotectant, i.e. as a hepatoprotective agent.

In addition the present invention relates to a pharmaceutical composition comprising (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate for use as hepatoprotective agent and for use in the protection of the liver against hepatotoxicity, the improvement of liver function, the protection/repair of liver injury, and/or the prophylaxis or treatment of a liver disorder/disease as demonstrated by reducing serum levels of hepatic enzymes.

BACKGROUND OF THE INVENTION

The liver is not only involved in metabolism and detoxification, but also participates in innate immune function and thus frequently exposed to harmful impacts potentially leading to physical injury. Interestingly, liver has the unique ability to regenerate and completely recoup from most acute, non-iterative situation. However, multiple conditions, including viral hepatitis, non-alcoholic fatty liver disease, long term alcohol abuse and chronic use of medications can cause persistent injury in which regenerative capacity eventually becomes dysfunctional resulting in hepatic scaring and cirrhosis. Despite constant therapeutic advances and development of modern medicine, hepatic diseases remain a health problem worldwide.

Liver is a primary organ involved in biotransformation of food and drugs. Hepatic diseases are a major worldwide problem. Hepatotoxicity is most commonly seen in the form of malfunction or damage to the liver due to excess amount of drugs or xenobiotics. Hepatotoxicants are exogenous agents of clinical relevance which may include an overdose of certain medicinal compounds, industrial chemicals etc., which causes liver injury.

The exact mechanism of drug induced liver injury remains largely unknown, but it appears to involve two pathways—direct hepatotoxicity (Type A or DILI1 (drug induced liver injury1), intrinsic or predictable drug reaction) and indirect hepatotoxicity (Type B or DILI2 (drug induced liver injury2), unpredictable or idiosyncratic drug reaction,) or adverse immune reaction.

Hepatotoxicity may result into cytotoxic effects (necrosis, apoptosis), cholestasis, steatosis, fibrosis, cirrhosis, hepatitis and liver tumors. Hepatotoxicity related symptoms may include jaundice or icterus appearance causing yellowing of the skin, eyes and severe abdominal pain, nausea or vomiting, weakness, severe fatigue, continuous bleeding, skin rashes, generalized itching, swelling of the feet and/or legs, abnormal and rapid weight gain in a short period of time, dark urine and light colored stools. Increase of various liver enzymes in serum is considered a sign of hepatotoxicity.

It is the another objective of the present invention to provide a compound for use as a hepatoprotectant, i.e. hepatoprotective agent and use in the protection of the liver against hepatotoxicity, the improvement of liver function, the protection/repair of liver injury, and/or the prophylaxis or treatment of a liver disorder/disease.

The objective of the present invention is solved by the teaching of the independent claims. Further advantageous features, aspects and details of the invention are evident from the dependent claims, the description, the figures, and the examples of the present application.

BRIEF DESCRIPTION OF THE INVENTION

The objective of the present invention is solved by use of the compound (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

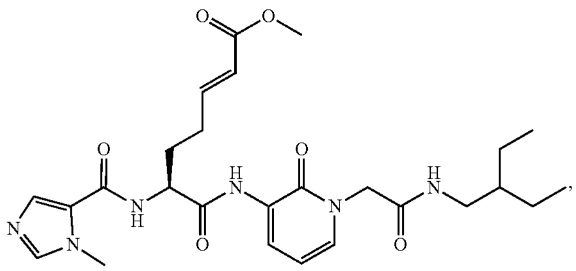

or an enantiomer, a solvate, a hydrate or a pharmaceutically acceptable salt of formula (I) as a hepatoprotectant, i.e. as a hepatoprotective agent.

In one embodiment, the invention refers to the compound of the formula (I) for use in the protection of the liver against hepatotoxicity, the improvement of liver function, the protection/repair of liver injury, and/or the prophylaxis or treatment of a liver disorder/disease.

In one embodiment, the invention refers to the compound of the formula (I) for use in the protection of the liver against hepatotoxicity, the improvement of liver function, the protection/repair of liver injury, and/or the prophylaxis or treatment of a liver disorder/disease, wherein the compound reduces serum levels of at least one hepatic enzyme, preferably the at least one hepatic is selected from alanine aminotransferase (ALT), aspartate aminotransferase (AST), and alkaline phosphatase (ALP).

In one embodiment, the invention refers to the compound of the formula (I) for use in the prophylaxis or treatment of a liver disorder/disease, wherein the liver disorder/disease is liver fibrosis, alcoholic hepatitis, nonalcoholic steatohepatitis (NASH), non-alcoholic fatty liver disease (NAFLD), cirrhosis, cholestatic liver diseases such as primary sclerosing cholangitis (PSC), and primary biliary cholangitis (PBC), autoimmune hepatitis (AIH), alcoholic steatohepatitis (ASH), or liver inflammation.

In one embodiment, the invention refers to the compound of the formula (I) for use in the protection of the liver against hepatotoxicity, the improvement of liver function, the protection/repair of liver injury, and/or the prophylaxis or treatment of a liver disorder/disease, wherein the hepatotoxicity, the liver injury, or the liver disorder/disease is caused by at least one hepatotoxicant, preferably the at least one hepatotoxicant is selected from the group comprising or consisting of toxic chemicals, xenobiotics, anticancer drugs, immunosuppressant drugs, analgesic drugs, anti-inflammatory drugs, anti-tubercular drugs, biologicals, radiations, heavy metals, mycotoxin, galactosamine, and lipopolysaccharides.

In one embodiment, the invention refers to the compound of the formula (I) for use in the prophylaxis or treatment of a liver disorder/disease, wherein the liver disorder/disease is liver fibrosis, in combination with one or more therapeutic agents.

In one embodiment, the invention refers to the compound of the formula (I) for use, wherein the compound is administered orally.

Another aspect of the invention is directed to a pharmaceutical composition comprising a compound (5,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

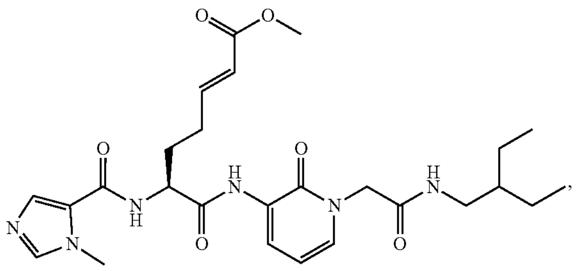

or an enantiomer, a solvate, a hydrate or a pharmaceutically acceptable salt thereof for use as a hepatoprotectant.

Preferably, the pharmaceutical composition is useful in the protection of the liver against hepatotoxicity, the improvement of liver function, the protection/repair of liver injury, and/or the prophylaxis or treatment of a liver disorder/disease.

Preferably, the hepatotoxicity or the liver injury, the liver disorder/disease is caused by at least one hepatotoxicant, celiac disease, or a viral infection.

In particular, the at least one hepatotoxicant is selected from the group comprising or consisting of toxic chemicals, xenobiotics, anticancer drugs, immunosuppressant drugs, analgesic drugs, anti-inflammatory drugs, anti-tubercular drugs, biologicals, radiations, heavy metals, mycotoxin, galactosamine, and lipopolysaccharides; celiac disease associated with a specific genetic phenotype (HLA DQ2/DQ8) and a pathobiology promoted by transglutaminase 2 (TG2); and/or the viral infection with hepatitis A, B, C viruses.

In one embodiment, the invention refers to said pharmaceutical composition for use in the protection of the liver against hepatotoxicity, the improvement of liver function, the protection/repair of liver injury, and/or the prophylaxis or treatment of a liver disorder/disease, wherein the compound reduces serum levels of at least one hepatic enzyme, preferably the at least one hepatic enzyme is selected from alanine aminotransferase (ALT), aspartate aminotransferase (AST), and alkaline phosphatase (ALP).

In one embodiment, the invention refers to said pharmaceutical composition for use in the protection of the liver against hepatotoxicity, the improvement of liver function, the protection/repair of liver injury, and/or the prophylaxis or treatment of a liver disorder/disease, wherein the liver disorder/disease is liver fibrosis, alcoholic hepatitis, nonalcoholic steatohepatitis (NASH), non-alcoholic fatty liver disease (NAFLD), cirrhosis, cholestatic liver diseases such as primary sclerosing cholangitis (PSC), and primary biliary cholangitis (PBC), autoimmune hepatitis (AIH), alcoholic steatohepatitis (ASH), or liver inflammation.

In one embodiment, the invention refers to said pharmaceutical composition for use in the protection of the liver against hepatotoxicity, the improvement of liver function, the protection/repair of liver injury, and/or the prophylaxis or treatment of a liver disorder/disease, wherein the pharmaceutical composition further comprises at least one polymeric precipitation inhibitor.

Preferably, the at least one polymeric precipitation inhibitor is selected from the group consisting of L-hydroxypropyl cellulose, hydroxypropyl cellulose, a combination of L-hydroxypropyl cellulose and hydroxypropyl cellulose, polyethylene glycol, poly(ethylene oxide)-poly (propylene oxide)-poly (ethylene oxide), polyvinyl alcohol, polyvinylpyrrolidone, carboxymethyl cellulose, methylcellulose, hydroxyethylcellulose, hydroxypropylmethylcellulose, ethylcellulose, polyvinyl alcohol (PVA), polyvinyl caprolactam-polyvinyl acetate-polyethylene glycol graft copolymer, and sodium carboxymethyl cellulose.

In one embodiment, the invention refers to the pharmaceutical composition for use, wherein the pharmaceutical composition further comprises at least one acidifier and/or at least one binder.

In a preferred embodiment, the invention refers to said pharmaceutical composition for use in the protection of the liver against hepatotoxicity, the improvement of liver function, the protection/repair of liver injury, and/or the prophylaxis or treatment of a liver disorder/disease, wherein the at least one acidifier is selected from the group consisting of ascorbic acid, organic di-carboxylic acid such as oxalic acid, malonic acid, succinic acid, glutaric acid, tartaric acid, fumaric acid, maleic acid, malic acid, adipic acid, or glutamic acid, and organic tri-carboxylic acid such as citric acid, or sodium hydrogen citrate.

In a preferred embodiment, the invention refers to said pharmaceutical composition for use in the protection of the liver against hepatotoxicity, the improvement of liver function, the protection/repair of liver injury, and/or the prophylaxis or treatment of a liver disorder/disease, wherein the at least one binder is selected from the group consisting of sugar, sucrose, polysaccharides, xanthan gum, guar gum, carrageenan, starches derived from wheat, corn, rice and potatoes, preagglutinated (modified) starch derived from wheat, corn, rice and potatoes, sodium starch glycolate, natural gums, acacia gum, gelatin, tragacanth, derivatives of sea weed, alginic acid, sodium alginate, ammonium calcium alginate, cellulose, cellulose derivatives, hydroxypropyl cellulose, L-hydroxypropyl cellulose, low-substituted hydroxypropyl cellulose, methyl cellulose, sodium carboxymethylcellulose, hydroxypropyl methylcellulose, polyvinylpyrrolidone, povidone K25.

In one embodiment, the invention refers to said pharmaceutical composition for use in the protection of the liver against hepatotoxicity, the improvement of liver function, the protection/repair of liver injury, and/or the prophylaxis or treatment of a liver disorder/disease, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size distribution which is defined by $d(0.95) \leq 25$ μm.

In some embodiments, the invention refers to said pharmaceutical composition for use in the protection of the liver against hepatotoxicity, the improvement of liver function, the protection/repair of liver injury, and/or the prophylaxis or treatment of a liver disorder/disease, wherein the pharmaceutical composition is an oral formulation, preferably the oral formulation is a tablet, capsule, powder, or granule.

In a preferred embodiment, the invention refers to said pharmaceutical composition for use in the protection of the liver against hepatotoxicity, the improvement of liver function, the protection/repair of liver injury, and/or the prophylaxis or treatment of a liver disorder/disease, wherein the pharmaceutical composition comprises 1 to 15 m/m acidifier, 0.1 to 7 m/m polymeric precipitation inhibitor, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

In a preferred embodiment, the invention refers to the pharmaceutical composition for use in the protection of the liver against hepatotoxicity, the improvement of liver function, the protection/repair of liver injury, and/or the prophylaxis or treatment of a liver disorder/disease, wherein the pharmaceutical composition comprises 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 3 wt % to 75 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

In a preferred embodiment, the invention refers to the pharmaceutical composition for use in the protection of the liver against hepatotoxicity, the improvement of liver function, the protection/repair of liver injury, and/or the prophylaxis or treatment of a liver disorder/disease, wherein the pharmaceutical composition comprises 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 3 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

In a preferred embodiment, the invention refers to the pharmaceutical composition for use in the prophylaxis or treatment of a liver disorder/disease, wherein the liver disorder/disease is liver fibrosis.

DESCRIPTION OF THE INVENTION

As used herein, the term "pharmaceutically acceptable salts" refers to salts of certain ingredient(s) which possess the same activity as the unmodified compound(s) and which are neither biologically nor otherwise undesirable. A pharmaceutically acceptable salt can be formed with, for example, organic or inorganic acids. Suitable acids include acetic acid, acetylsalicylic acid, organic di-carboxylic acid such as oxalic acid, malonic acid, succinic acid, glutaric acid, tartaric acid, fumaric acid, maleic acid, malic acid, adipic acid, or glutamic acid, and organic tri-carboxylic acid such as citric acid, or sodium hydrogen citrate alginic acid, ascorbic acid, aspartic acid, benzoic acid, benzenesulfonic acid, bisulfic acid, boric acid, butyric acid, camphoric acid, camphorsulfonic acid, carbonic acid, citric acid, cyclopentanepropionic acid, digluconic acid, dodecylsulfic acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylanesulfonic acid, naphthylic acid, nicotinic acid, nitrous acid, oxalic acid, pelargonic, phosphoric acid, propionic acid, saccharin, salicylic acid, sorbic acid, succinic acid, sulfuric acid, tartaric acid, thiocyanic acid, thioglycolic acid, thiosulfuric acid, tosylic acid, undecylenic acid, and naturally and synthetically derived amino acids. Preferably, the acid is adipic acid, fumaric acid, glutaric acid, more preferably, the acid is adipic acid.

Thus, a preferred pharmaceutically acceptable salt is a salt of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

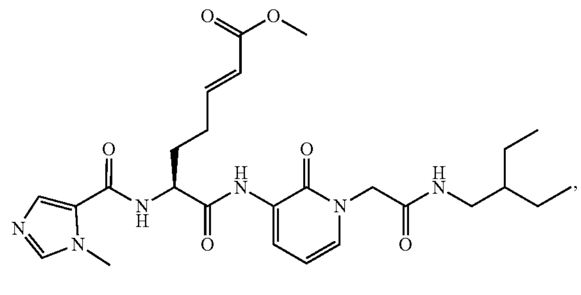

and adipic acid.

As used herein, the term "solvates" refers to those forms of a compound in particular the (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate which form a complex through coordination with solvent molecules.

As used herein, the term "hydrates" refers to those forms of a compound in particular the (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate which form a complex through coordination with water molecules.

As used herein, the term "effective amount" or "therapeutically effective amount" of an active agent or a pharmaceutically active agent or a drug or an active pharmaceutical ingredient, which are synonymous herein, refers to an amount of the active agent or pharmaceutically active agent or drug or active pharmaceutical ingredient, sufficient enough to have a positive effect. Accordingly, these amounts are disease to be treated but low enough to avoid serious side effects. A therapeutically effective amount of the pharmaceutically active agent will cause a substantial relief of symptoms when applied repeatedly over time. Effective amounts of the pharmaceutically active agent will vary with the particular condition or conditions being treated, the severity of the condition, the duration of the treatment, the specific components of the composition being used, and like factors.

As used herein, the term "active agent", "pharmaceutically active agent", "drug" or "active pharmaceutical ingredient", "therapeutic agent" which are synonymously used herein, refers to a compound exhibiting a therapeutic effect upon a mammal in particular a human.

As used herein, the term "treatment," "treating," or similar language refers to a process to (1) delay onset of a disease that is causing clinical symptoms; (2) inhibiting a disease, that is, arresting the development of clinical symptoms; and/or (3) relieving the disease, that is, causing the regression of clinical symptoms or the severity thereof.

As used herein, the term "pharmaceutical composition" refers to a composition which, upon administration, demonstrates a therapeutic effect upon a mammal.

"oral formulation", as used herein, refers to a formulation being a medication which is absorbed through the mouth (per os, orally, perorally tablets, dragees, capsules, juices, drops, etc.). These medicines are absorbed into the blood in the gastrointestinal tract, and then enter the liver via the portal vein system and then into the bloodstream via the hepatic vein. The term, as used herein, refers to a formulation which is administered orally.

Hepatic disorders are herein mainly caused by hepatotoxicants. "Hepatotoxicant", includes, but not limited to the toxic chemicals (alcohols), xenobiotics (carbon tetrachloride, chlorinated hydrocarbons, isocyanates, pesticides such as insecticides, fungicide, herbicides, and detergents such as bile acid salts), anticancer (azathioprine, doxorubicin, cisplatin), immunosuppressant (cyclosporine), analgesic anti-inflammatory (paracetamol, thioacetamide), anti-tubercular (isoniazid, rifampicin) drugs, biologicals (Bacillus-Calmette-Guerin vaccine), radiations (gamma radiations), heavy metals (cadmium, arsenic), mycotoxin (aflatoxin), galactosamine, and lipopolysaccharides. Various risk factors for hepatic injury include concomitant hepatic diseases, age, gender, alcoholism, nutrition and genetic polymorphisms of cytochrome $P_{450}$ enzymes have also been emphasized.

The most commonly used parameters to assess the hepatoprotective activity were morphological e.g. Liver weight and volume, biochemical estimations, such as measurement of transaminase activity, SGPT, SCOT, alkaline phosphatase, serum bilirubin, total serum proteins, albumin, globulin and prothrombin time, functional parameters, pentobarbitone and hexobarbitone sleeping time and finally histopathological study regarding presence of necrosis, fatty degeneration and cirrhosis.

To identify various diseases related to the liver, several test items are collectively referred to as liver function tests. Major tests include the activity of the serum levels of hepatic enzymes including alanine transaminase (ALT) or serum glutamate-pyruvate transaminase (SGPT), aspartate transaminase (AST) or serum glutamic oxaloacetic transaminase (SGOT), gamma-glutamyltransferase (GGT), and alkaline phosphatase (ALP) and bilirubin. In addition, total protein, albumin, LDH (lactic acid dehydrogenase), ammonia, etc. are sometimes tested.

Among them, AST (GOT) and ALT (GPT) are enzymes present in liver cells and are mainly released into the blood when the liver cells are damaged. Therefore, blood AST and ALT levels can be used as markers for liver damage. In the early stages of acute hepatocyte injury, AST, which has a high concentration of hepatocytes, increases more than ALT, but after 24 to 48 hours and in chronic hepatocyte injury, ALT levels with a longer half-life are generally higher. In alcoholic hepatitis, AST is further increased.

Surprisingly, it is proven that the compound of the formula (I) could lower the alanine aminotransferase (ALT) and aspartate aminotransferase (AST), alkaline phosphatase (ALP) concentrations in serum in a dose dependent manner as shown in Table 4 in Example 14. These results indicate that the compound of the formula (I) has a protective effect on hepatic injury and has a potential in therapeutics of hepatic injury.

Celiac disease is characterized by a gluten-related pathobiology driven by transglutaminase 2 (TG2). Celiac disease, a gluten intolerance, however, is one of the most prevalent gastrointestinal indications. Celiac disease is characterized by a chronic inflammation of the mucosa of the small intestine. In patients concerned, the intestine epithelium is successively destroyed after ingestion of gluten-containing food resulting in reduced absorption of nutrients which again has massive impact on the patients concerned and is for example associated with symptoms such as loss of weight, anemia, diarrhea, nausea, loss of appetite and fatigue.

The mechanisms underlying liver injury in celiac disease are poorly understood. However, the elevation of aminotransferase levels is a characteristic presenting feature in patients with celiac disease.

In vivo, oral treatment with compound 1 as an irreversible inhibitor of transglutaminase 2 (TG2) at doses of 10, 50 and 100 mg in human significantly reduced the levels of AST, ALT, total protein and inhibited cellular leakage of two enzymes, hepatocyte aspartate aminotransferase (AST) and alanine aminotransferase (ALT).

The efficacy and safety of a 6-week treatment with the compound of formula (I) in the hard gelatine capsule formulation described in example 2 was investigated in 160 adult patients with Celiac Disease (CeD). Patients, who were in clinical and histological remission at start of the study were challenged with 3 grams daily gluten intake and randomized to receive placebo or one of 3 doses of the compound of formula (I), i.e. 10 mg, 50 mg or 100 mg. Each morning after at least 6 hours of fasting, patients took the study drug orally, followed by one biscuit containing 3 g of gluten 30 minutes later, before breakfast. Throughout the 6-week study, patients were required to continue their strict gluten free diet.

Gluten challenge caused a mild but statistically significant elevation of alanine aminotransferase (ALT) from baseline to week 6 in the placebo group, but this elevation was surprisingly not observed in any of the groups the compound of formula (I) in the hard gelatine capsule formulation described in example 2. The difference between each drug group and placebo in ALT was statistically significant ($P<0.01$ for all comparisons), demonstrating a protective effect by the compound of the formula (I) on the liver of celiac disease patients exposed to gluten. Alkaline phosphatase (ALP) levels showed also a similar pattern ($P<0.05$). In the placebo group, the values normalized upon gluten-free diet (GFD) at week 10 (table 1). The finding that the compound of formula (I) inhibits liver injury, which is one of the gluten-driven extraintestinal manifestations in active Celiac Disease (CeD), as reflected in a mild elevation of ALT and ALP, demonstrates that the compound exerts a general hepatoprotective effect (see FIG. 12).

Administration of the compound of formula (I) in a mouse model for non-alcoholic steatohepatitis demonstrated a dose dependent reduction of liver fibrosis (Example 3). Surprisingly, the administration of the compound of formula (I) in STAM mice led also to a dose-dependent and significant reduction of liver inflammation which is further evidence for its hepatoprotective effect.

Thus, an embodiment of the invention is related to use of the compound (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

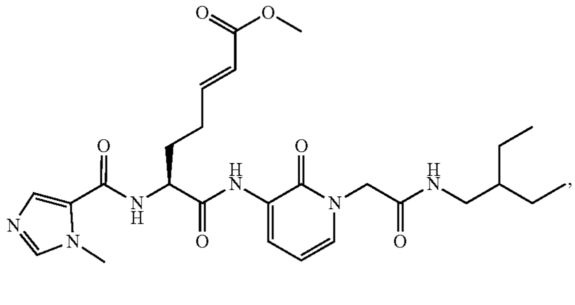

, or an enantiomer, a solvate, a hydrate or a pharmaceutically acceptable salt of formula (I) as a hepatoprotectant, i.e. as a hepatoprotective agent.

In one embodiment, the invention refers to the compound of the formula (I), the enantiomer, the solvate, the hydrate or the pharmaceutically acceptable salt thereof for use in the protection of the liver against hepatotoxicity, the improvement of liver function, the protection/repair of liver injury, and/or the prophylaxis or treatment of a liver disorder/disease.

In one embodiment, the invention refers to the compound of the formula (I), the enantiomer, the solvate, the hydrate or the pharmaceutically acceptable salt thereof for use in the protection of the liver against hepatotoxicity, the improvement of liver function, the protection/repair of liver injury, and/or the prophylaxis or treatment of a liver disorder/disease, wherein the compound reduces serum levels of at least one hepatic enzyme, preferably the at least one hepatic enzyme is selected from alanine aminotransferase (ALT), aspartate aminotransferase (AST), and alkaline phosphatase (ALP).

In one embodiment, the invention refers to the compound of the formula (I), the enantiomer, the solvate, the hydrate or the pharmaceutically acceptable salt thereof for use in the protection of the liver against hepatotoxicity, the improvement of liver function, the protection/repair of liver injury, and/or the prophylaxis or treatment of a liver disorder/disease, wherein the liver disorder/disease is liver fibrosis, alcoholic hepatitis, nonalcoholic steatohepatitis (NASH), non-alcoholic fatty liver disease (NAFLD), cirrhosis, cholestatic liver diseases such as primary sclerosing cholangitis (PSC), and primary biliary cholangitis (PBC), autoimmune hepatitis (AIH), alcoholic steatohepatitis (ASH), or liver inflammation.

In one embodiment, the invention refers to the compound of the formula (I), the enantiomer, the solvate, the hydrate or the pharmaceutically acceptable salt thereof for use in the protection of the liver against hepatotoxicity, the improvement of liver function, the protection/repair of liver injury, and/or the prophylaxis or treatment of a liver disorder/disease, wherein the hepatotoxicity, the liver injury, or the liver disorder/disease is caused by at least one hepatotoxicant, celiac disease, or a viral infection, preferably the at least one hepatotoxicant is selected from the group comprising or consisting of toxic chemicals, xenobiotics, anti-cancer drugs, immunosuppressant drugs, analgesic drugs, anti-inflammatory drugs, anti-tubercular drugs, biologicals, radiations, heavy metals, mycotoxin, galactosamine, and lipopolysaccharides; celiac disease associated with a specific genetic phenotype (HLA DQ2/DQ8) and a pathobiology promoted by transglutaminase 2 (TG2); and/or the viral infection with hepatitis A, B, C viruses.

Preferably, the toxic chemicals are alcohols, xenobiotics are carbon tetrachloride, chlorinated hydrocarbons, isocyanates, pesticides such as insecticides, fungicide, herbicides, and detergents such as bile acid salts; anticancer drugs is azathioprine, doxorubicin, cisplatin; immunosuppressant drug is cyclosporine, anti-inflammatory drugs are paracetamol, and thioacetamide; anti-tubercular drugs are isoniazid, and rifampicin; biologicals is for example, Bacillus-Calmette-Guerin vaccine, radiations is preferred gamma radiations, heavy metals are cadmium, and arsenic; mycotoxin is aflatoxin, galactosamine, and lipopolysaccharides.

Preferably, the invention refers to the compound of the formula (I), the enantiomer, the solvate, the hydrate or the pharmaceutically acceptable salt thereof for use in the protection of the liver against hepatotoxicity, the improvement of liver function, the protection/repair of liver injury, and/or the prophylaxis or treatment of a liver disorder/disease, wherein the hepatotoxicity, liver injury, or the liver disorder/disease is caused by celiac disease, and celiac disease is associated with transglutaminase 2 (TG2).

In one embodiment, the invention refers to the compound of the formula (I) the compound of the formula (I), the enantiomer, the solvate, the hydrate or the pharmaceutically acceptable salt thereof for use as described above, wherein the compound is administered orally.

A Pharmaceutical Composition for Use as a Hepatoprotectant

Another aspect of the invention is directed to a pharmaceutical composition comprising a compound (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

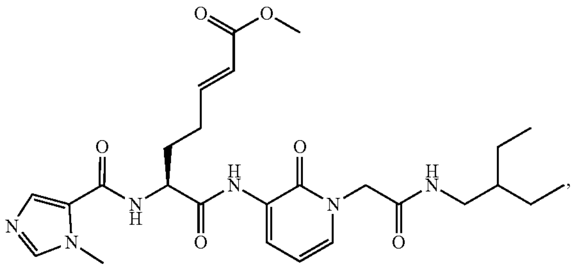

or an enantiomer, a solvate, a hydrate or a pharmaceutically acceptable salt thereof for use as a hepatoprotectant.

Preferably, said pharmaceutical composition is useful in the protection of the liver against hepatotoxicity, the improvement of liver function, the protection/repair of liver injury, and/or the prophylaxis or treatment of a liver disorder/disease.

Preferably, the hepatotoxicity or the liver injury, the liver disorder/disease is caused by at least one hepatotoxicant, celiac disease, or a viral infection.

In particular, the at least one hepatotoxicant is selected from the group comprising or consisting of toxic chemicals, xenobiotics, anticancer drugs, immunosuppressant drugs, analgesic drugs, anti-inflammatory drugs, anti-tubercular drugs, biologicals, radiations, heavy metals, mycotoxin, galactosamine, and lipopolysaccharides.

In one embodiment, the invention refers to the pharmaceutical composition comprising a compound of the formula (I), an enantiomer, a solvate, a hydrate or a pharmaceutically acceptable salt thereof for use in the protection of the liver against hepatotoxicity, the improvement of liver function, the protection/repair of liver injury, and/or the prophylaxis or treatment of a liver disorder/disease, wherein the at least one hepatotoxicant is selected from the group comprising or consisting of toxic chemicals, xenobiotics, anticancer drugs, immunosuppressant drugs, analgesic drugs, anti-inflammatory drugs, anti-tubercular drugs, biologicals, radiations, heavy metals, mycotoxin, galactosamine, and lipopolysaccharides celiac disease associated with a specific genetic phenotype (HLA DQ2/DQ8) and a pathobiology promoted by transglutaminase 2 (TG2); and/or a viral infection with hepatitis A, B, C viruses.

In one embodiment, the invention refers to said pharmaceutical composition comprising a compound of the formula (I), a enantiomer, a solvate, a hydrate or a pharmaceutically acceptable salt thereof for use in the protection of the liver against hepatotoxicity, the improvement of liver function, the protection/repair of liver injury, and/or the prophylaxis or treatment of a liver disorder/disease, wherein the compound reduces serum levels of at least one hepatic enzyme, preferably the at least one hepatic enzyme is selected from alanine aminotransferase (ALT), aspartate aminotransferase (AST), and alkaline phosphatase (ALP).

In one embodiment, the invention refers to said pharmaceutical composition comprising a compound of the formula (I), a enantiomer, a solvate, a hydrate or a pharmaceutically acceptable salt thereof for use in the protection of the liver against hepatotoxicity, the improvement of liver function, the protection/repair of liver injury, and/or the prophylaxis or treatment of a liver disorder/disease, wherein the liver disorder/disease is liver fibrosis, alcoholic hepatitis, nonalcoholic steatohepatitis (NASH), non-alcoholic fatty liver disease (NAFLD), cirrhosis, cholestatic liver diseases such as primary sclerosing cholangitis (PSC), and primary biliary cholangitis (PBC), autoimmune hepatitis (AIH), alcoholic steatohepatitis (ASH), or liver inflammation.

Preferably, the invention also refers to said pharmaceutical composition comprising a compound of the formula (I), an enantiomer, a solvate, a hydrate or a pharmaceutically acceptable salt thereof for use in the protection of the liver against hepatotoxicity, the improvement of liver function, the protection/repair of liver injury, and/or the prophylaxis or treatment of a liver disorder/disease in combination with a gluten free diet, wherein the hepatotoxicity, liver injury, or the liver disorder/disease is caused by celiac disease, and celiac disease is associated with transglutaminase 2 (TG2).

In one embodiment, the invention refers to said pharmaceutical composition comprising a compound of the formula (I), a enantiomer, a solvate, a hydrate or a pharmaceutically acceptable salt thereof for use in the protection of the liver against hepatotoxicity, the improvement of liver function, the protection/repair of liver injury, and/or the prophylaxis or treatment of a liver disorder/disease, wherein the pharmaceutical composition further comprises at least one polymeric precipitation inhibitor.

Preferably the "polymeric precipitation inhibitor" is selected from the group comprising or consisting of:

cellulose derivatives including but not limited to microcrystalline cellulose (MCC), cellulose acetate phthalate (CAP), cellulose acetate terephthalate, cellulose acetate isophthalate, cellulose acetate butyrate (CAB), cellulose acetate trimellitate (CAT), methylcellulose (MC), methylcellulose acetate phthalate, ethylcellulose (EC), carboxymethyl cellulose (CMC), sodium carboxymethyl cellulose, carboxymethylethylcellulose (CMEC), hydroxymethylcellulose (HMC), hydroxyethylcellulose (HEC), hydroxypropyl cellulose (HPC or hyprolose), L-hydroxypropyl cellulose, hydroxypropylmethylcellulose (HPMC or hypromellose), carboxymethyl hydroxyethyl cellulose (CMHEC), sodium carboxymethyl hydroxyethyl cellulose (NaCMHEC), hydroxypropyl methylcellulose phthalate (HPMCP, hypromellose phtahalate), hydroxypropyl methylcellulose acetate succinate (HPMCAS, hypromellose acetate succinate);

starch derivatives including but not limited to hydroxyethyl starch, hydroxypropyl starch (HPS) and pregelatinized starch;

dextran/dextrin derivatives including but not limited to cyclodextran (i.e., cycloisomalto-heptaose (CI-7), cycloisomalto-octaose (CI-8), cycloisomalto-nonaose (CI-9)), hydroxypropyl dextran, maltodextrin, α-/β-/γ-cyclodextrin, 2-hydroxyethyl-β-cyclodextrin, 2-hydroxypropyl-β-cyclodextrin (HPβCD), sulfobuthylether-β-cyclodextrin sodium salt, methylated-p-cyclodextrin, 2-hydroxypropyl-γ-cyclodextrin;

polyether derivatives including but not limited to polyethylene glycol (PEG), polyethylene oxide (PEO), polyether polyol, poly(propylene glycol) bis(2-aminopropyl ether) (PPGAE), poly(ethylene oxide)-poly (propylene oxide)-poly (ethylene oxide) (PEO-PPO-PEO, poloxamer) such as poloxamer 188 and poloxamer 407, polyvinyl derivatives including but not limited to polyvinyl alcohol (PVA), polyvinyl acetate phthalate (PVAP), polyvinylpyrrolidone (PVP), polyvinylpyrrolidone-co-polyvinyl acetate (PVPVA), polyvinyl caprolactam-polyvinyl acetate-polyethylene glycol graft copolymer (Soluplus®)

polyacrylic acid derivatives including but not limited to poly(acrylic acid) (PAA), poly(acrylamide/acrylic acid) (PAC-AC), polymethylacrylate (PMA), polymethacrylic acid, poly(methacrylic acid/methyl methacrylate), poly(methacrylic acid/ethyl acrylate);

polyamine derivatives including but not limited to polyethylene imine (PEI), polyallylamine hydrogen chloride, polydiallydimethyl ammonium chloride, and poly (2-ethyl-2-oxazoline);

polysulfonic acid derivatives including but not limited to polystyrensulfonic acid (PSSA); and a combination of at least two of the above-mentioned polymeric precipitation inhibitors.

More preferably, the "polymeric precipitation inhibitor" is selected from the group comprising or consisting of: microcrystalline cellulose (MCC), cellulose acetate phthalate (CAP), cellulose acetate terephthalate, cellulose acetate isophthalate, cellulose acetate butyrate (CAB), cellulose acetate trimellitate (CAT), methylcellulose (MC), methylcellulose acetate phthalate, ethylcellulose (EC), carboxymethyl cellulose (CMC), sodium carboxymethyl cellulose, carboxymethylethylcellulose (CMEC), hydroxymethylcellulose (HMC), hydroxyethylcellulose (HEC), hydroxypropyl cellulose (HPC or hyprolose), L-hydroxypropyl cellulose, hydroxypropylmethylcellulose (HPMC or hypromellose), carboxymethyl hydroxyethyl cellulose (CMHEC), sodium carboxymethyl hydroxyethyl cellulose (NaCMHEC), hydroxypropyl methylcellulose phthalate (HPMCP, hypromellose phtahalate), hydroxypropyl methylcellulose acetate succinate (HPMCAS, hypromellose acetate succinate), polyethylene glycol (PEG), polyethylene oxide (PEO), polyether polyol, poly(propylene glycol) bis (2-aminopropyl ether) (PPGAE), poly(ethylene oxide)-poly (propylene oxide)-poly (ethylene oxide) (PEO-PPO-PEO, poloxamer) such as poloxamer 188 and poloxamer 407, polyvinyl alcohol (PVA), polyvinyl acetate phthalate (PVAP), polyvinylpyrrolidone (PVP), polyvinylpyrrolidone-co-polyvinyl acetate (PVPVA), polyvinyl caprolactam-polyvinyl acetate-polyethylene glycol graft copolymer (Soluplus®), poly(acrylic acid) (PAA), poly (acrylamide/acrylic acid) (PAC-AC), polymethacrylate (PMA), polymethacrylic acid, poly(methacrylic acid/methyl methacrylate), poly(methacrylic acid/ethyl acrylate), and a combination of at least two of the above-mentioned polymeric precipitation inhibitors.

Preferably, the at least one polymeric precipitation inhibitor is selected from the group consisting of L-hydroxypropyl cellulose, hydroxypropyl cellulose, a combination of L-hydroxypropyl cellulose and hydroxypropyl cellulose, polyethylene glycol, poly(ethylene oxide)-poly (propylene oxide)-poly (ethylene oxide), polyvinyl alcohol, polyvinylpyrrolidone, carboxymethyl cellulose, methylcellulose, hydroxyethylcellulose, hydroxypropylmethylcellulose, ethylcellulose, polyvinyl caprolactam-polyvinyl acetate-polyethylene glycol graft copolymer (Soluplus®) and sodium carboxymethyl cellulose.

Thus, in one embodiment, the invention refers to said pharmaceutical composition comprising a compound of the formula (I), a enantiomer, a solvate, a hydrate or a pharmaceutically acceptable salt thereof for use in the protection of the liver against hepatotoxicity, the improvement of liver function, the protection/repair of liver injury, and/or the prophylaxis or treatment of a liver disorder/disease, wherein the pharmaceutical composition further comprises at least one polymeric precipitation inhibitor and the at least one polymeric precipitation inhibitor is selected from the group consisting of L-hydroxypropyl cellulose, hydroxypropyl cellulose, a combination of L-hydroxypropyl cellulose and hydroxypropyl cellulose, polyethylene glycol, poly(ethylene oxide)-poly (propylene oxide)-poly (ethylene oxide), polyvinyl alcohol, polyvinylpyrrolidone, carboxymethyl cellulose, methylcellulose, hydroxyethylcellulose, hydroxypropylmethylcellulose, ethylcellulose, polyvinyl caprolactam-polyvinyl acetate-polyethylene glycol graft copolymer (Soluplus®) and sodium carboxymethyl cellulose.

Additionally, the positive data of the pharmacokinetic study in human confirms the high bioavailability of compound (I). A high bioavailability in this context has to be understood in comparison to the animal studies which have been performed previously.

The STAM- and UUO mouse model studies demonstrate an anti-fibrotic effect on the liver and kidney being achieved by the administration of a systemic formulation containing the compound according to formula (I). Therefore, the drug of formula (I) shows a high anti-fibrotic effect at the target site, and thereby indicates a systemic bioavailability. Thus, the administration of the drug of formula (I) exhibits a high anti-fibrotic effect at the target site, and thus a systemic availability (bioavailability) can be derived, i.e. the drug is absorbed at the target tissue.

Surprisingly, the administration of the drug of formula (I) in STAM mice led not only to a reduction of fibrosis but also to a dose-dependent and significant reduction of liver inflammation which is further evidence for the hepatoprotective effect.

The addition of an acidifier ensures the complete dissolution of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate in the stomach but the pH in the small intestine increases from 2 to 6, and thus the drug can precipitate before it can be absorbed by the small intestine. In order to ensure a complete dissolution of said compound in the small intestine, the formulation according to the invention contains preferably an acidifier, and/or a polymeric precipitation inhibitor. Moreover, it could be shown in example 9 that merely a dosage of 20 mg in human is sufficient to achieve effective drug concentrations in plasma, and thus a systemic availability.

The pharmacokinetic studies show that (5,E)-methyl-7-(1-(2-(2-ethylbutylamino)-2-oxoethyl)-2-oxo-1,2-dihydropyridin-3-ylamino)-6-(1-methyl-1H-imidazole-5-carboxamido)-7-oxohept-2-enoate is absorbed in the small intestine and a low dose of 20-50 mg is needed to achieve a therapeutic effective drug concentration in human (example 7, FIG. 6). In addition, an anti-fibrotic effect can already be achieved with a human dosage of 20 mg (example 9 and FIG. 9).

Moreover, off-target effects could not be observed. As aforementioned, this is particularly surprising due to the fact that TG2 is ubiquitously expressed in almost all cell types and cell compartments, it is present on the cell surface and gets secreted to the extracellular matrix, and is present in various organs, and thus it could be envisioned that off-target effects would be most likely.

In one embodiment, the invention refers to said pharmaceutical composition for use in the protection of the liver against hepatotoxicity, the improvement of liver function, the protection/repair of liver injury, and/or the prophylaxis or treatment of a liver disorder/disease, wherein the pharmaceutical composition further comprises at least one acidifier and/or at least one binder.

"Binders" are substances which bind or "glue" together powder particles and make them cohesive by forming granules, thus serving as the "adhesive" in the formulation. Binders add cohesive strength already available in the diluent or bulking agent. Suitable binders include sugar, sucrose, polysaccharides, xanthan gum, guar gum, carrageenan, starches derived from wheat, corn, rice and potatoes, preagglutinated (modified) starch derived from wheat, corn, rice and potatoes, sodium starch glycolate, natural gums, acacia gum, gelatin, tragacanth, derivatives of sea weed, alginic acid, sodium alginate, ammonium calcium alginate, cellulose, cellulose derivatives, hydroxypropyl cellulose, L-hydroxypropyl cellulose, low-substituted hydroxypropyl cellulose, methyl cellulose, sodium carboxymethylcellulose, hydroxypropyl methylcellulose, polyvinylpyrrolidone, povidone K25.

In one embodiment, the invention refers to said pharmaceutical composition for use in the protection of the liver against hepatotoxicity, the improvement of liver function, the protection/repair of liver injury, and/or the prophylaxis or treatment of a liver disorder/disease, wherein the pharmaceutical composition further comprises at least one acidifier and the at least one acidifier is selected from the group consisting of ascorbic acid, organic di-carboxylic acid such as oxalic acid, malonic acid, succinic acid, glutaric acid, tartaric acid, fumaric acid, maleic acid, malic acid, adipic acid, or glutamic acid, and organic tri-carboxylic acid such as citric acid, or sodium hydrogen citrate.

In one embodiment, the invention refers to said pharmaceutical composition comprising a compound of the formula (I), a enantiomer, a solvate, a hydrate or a pharmaceutically acceptable salt thereof for use in the protection of the liver against hepatotoxicity, the improvement of liver function, the protection/repair of liver injury, and/or the prophylaxis or treatment of a liver disorder/disease, wherein the pharmaceutical composition further comprises the at least one binder and the at least one binder is selected from the group consisting of sugar, sucrose, polysaccharides, xanthan gum, guar gum, carrageenan, starches derived from wheat, corn, rice and potatoes, preagglutinated (modified) starch derived from wheat, corn, rice and potatoes, sodium starch glycolate, natural gums, acacia gum, gelatin, tragacanth, derivatives of sea weed, alginic acid, sodium alginate, ammonium calcium alginate, cellulose, cellulose derivatives, hydroxypropyl cellulose, L-hydroxypropyl cellulose, low-substituted hydroxypropyl cellulose, methyl cellulose, sodium carboxymethylcellulose, hydroxypropyl methylcellulose, polyvinylpyrrolidone, povidone K25.

In a preferred embodiment, the invention refers to said pharmaceutical composition comprising a compound of the formula (I), a enantiomer, a solvate, a hydrate or a pharmaceutically acceptable salt thereof for use in the protection of the liver against hepatotoxicity, the improvement of liver function, the protection/repair of liver injury, and/or the prophylaxis or treatment of a liver disorder/disease, wherein the pharmaceutical composition further comprises at least one polymeric precipitation inhibitor and at least one acidifier, the at least one polymeric precipitation inhibitor is selected from the group consisting of L-hydroxypropyl cellulose, hydroxypropyl cellulose, a combination of L-hydroxypropyl cellulose and hydroxypropyl cellulose, polyethylene glycol, poly(ethylene oxide)-poly (propylene oxide)-poly (ethylene oxide), polyvinyl alcohol, polyvinylpyrrolidone, carboxymethyl cellulose, methylcellulose, hydroxyethylcellulose, hydroxypropylmethylcellulose, ethylcellulose, polyvinyl caprolactam-polyvinyl acetate-polyethylene glycol graft copolymer (Soluplus®) and sodium carboxymethyl cellulose; and the at least one acidifier is selected from the group consisting of ascorbic acid, organic di-carboxylic acid such as oxalic acid, malonic acid, succinic acid, glutaric acid, tartaric acid, fumaric acid, maleic acid, malic acid, adipic acid, or glutamic acid, and organic tri-carboxylic acid such as citric acid, or sodium hydrogen citrate.

In a preferred embodiment, the invention refers to said pharmaceutical composition comprising a compound of the formula (I), a enantiomer, a solvate, a hydrate or a pharmaceutically acceptable salt thereof for use in the protection of the liver against hepatotoxicity, the improvement of liver function, the protection/repair of liver injury, and/or the prophylaxis or treatment of a liver disorder/disease, wherein the pharmaceutical composition further comprises at least one polymeric precipitation inhibitor and at least one binder, the at least one polymeric precipitation inhibitor is selected from the group consisting of L-hydroxypropyl cellulose, hydroxypropyl cellulose, a combination of L-hydroxypropyl cellulose and hydroxypropyl cellulose, polyethylene glycol, poly(ethylene oxide)-poly (propylene oxide)-poly (ethylene oxide), polyvinyl alcohol, polyvinylpyrrolidone, carboxymethyl cellulose, methylcellulose, hydroxyethylcellulose, hydroxypropylmethylcellulose, ethylcellulose, polyvinyl caprolactam-polyvinyl acetate-polyethylene glycol graft copolymer (Soluplus®) and sodium carboxymethyl cellulose; and the at least one binder is selected from the group consisting of sugar, sucrose, polysaccharides, xanthan gum, guar gum, carrageenan, starches derived from wheat, corn, rice and potatoes, preagglutinated (modified) starch derived from wheat, corn, rice and potatoes, sodium starch glycolate, natural gums, acacia gum, gelatin, tragacanth, derivatives of sea weed, alginic acid, sodium alginate, ammonium calcium alginate, cellulose, cellulose derivatives, hydroxypropyl cellulose, L-hydroxypropyl cellulose, low-substituted hydroxypropyl cellulose, methyl cellulose, sodium carboxymethylcellulose, hydroxypropyl methylcellulose, polyvinylpyrrolidone, povidone K25.

In a preferred embodiment, the invention refers to said pharmaceutical composition comprising a compound of the formula (I), a enantiomer, a solvate, a hydrate or a pharmaceutically acceptable salt thereof for use in the protection of the liver against hepatotoxicity, the improvement of liver function, the protection/repair of liver injury, and/or the prophylaxis or treatment of a liver disorder/disease, wherein the pharmaceutical composition further comprises at least one polymeric precipitation inhibitor, at least one acidifier, and at least one binder,

- the at least one polymeric precipitation inhibitor is selected from the group consisting of L-hydroxypropyl cellulose, hydroxypropyl cellulose, a combination of L-hydroxypropyl cellulose and hydroxypropyl cellulose, polyethylene glycol, poly(ethylene oxide)-poly (propylene oxide)-poly (ethylene oxide), polyvinyl alcohol, polyvinylpyrrolidone, carboxymethyl cellulose, methylcellulose, hydroxyethylcellulose, hydroxypropylmethylcellulose, ethylcellulose, polyvinyl caprolactam-polyvinyl acetate-polyethylene glycol graft copolymer (Soluplus®) and sodium carboxymethyl cellulose;
- the at least one acidifier is selected from the group consisting of ascorbic acid, organic di-carboxylic acid such as oxalic acid, malonic acid, succinic acid, glutaric acid, tartaric acid, fumaric acid, maleic acid, malic acid, adipic acid, or glutamic acid, and organic tricarboxylic acid such as citric acid, or sodium hydrogen citrate; and
- the at least one binder is selected from the group consisting of sugar, sucrose, polysaccharides, xanthan gum, guar gum, carrageenan, starches derived from wheat, corn, rice and potatoes, preagglutinated (modified) starch derived from wheat, corn, rice and potatoes, sodium starch glycolate, natural gums, acacia gum, gelatin, tragacanth, derivatives of sea weed, alginic acid, sodium alginate, ammonium calcium alginate, cellulose, cellulose derivatives, hydroxypropyl cellulose, L-hydroxypropyl cellulose, low-substituted hydroxypropyl cellulose, methyl cellulose, sodium carboxymethylcellulose, hydroxypropyl methylcellulose, polyvinylpyrrolidone, povidone K25.

Preferably, the invention refers to any of above-described pharmaceutical composition for use in the protection of the liver against hepatotoxicity, the improvement of liver function, the protection/repair of liver injury, and/or the prophylaxis or treatment of a liver disorder/disease, wherein the pharmaceutical composition further comprises diluents, disintegrants, lubricants, glidents and/or coloring agent.

Suitable "diluents" are substances that usually make up the major portion of the composition or dosage form. Suitable diluents include sugars such as lactose, sucrose, mannitol, and sorbitol, starches derived from wheat, corn, rice, and potato, and celluloses such as microcrystalline cellulose.

The term "disintegrants" refers to materials added to the composition to support break apart (disintegrate) and release the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscarmellose, alginates such as alginic acid and sodium alginate, clays such as bentonites, and effervescent mixtures.

"Lubricants" refer to a class of substances which are added to the dosage form to enable the tablet granules etc. after being compressed to release from the mould by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules.

"Glidents" are materials that prevent caking of the components of the pharmaceutical composition and improve the flow characteristics of granulate so that flow is smooth and uniform. Suitable glidents include silicon dioxide and talc.

An embodiment of the invention is therefore directed to a pharmaceutical composition comprising or consisting of (5,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I) or an enantiomer, a solvate, a hydrate or a pharmaceutically acceptable salt thereof, and at least one excipient, for use in the protection of the liver against hepatotoxicity, the improvement of liver function, the protection/repair of liver injury, and/or the prophylaxis or treatment of a liver disorder/disease, wherein at least one excipient is a disintegrant.

An embodiment of the invention is therefore directed to a pharmaceutical composition comprising or consisting of (5,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one disintegrant, for use in the protection of the liver against hepatotoxicity, the improvement of liver function, the protection/repair of liver injury, and/or the prophylaxis or treatment of a liver disorder/disease.

The pharmaceutical composition according to the invention can comprise an acidifier, a polymeric precipitation inhibitor, a binder and/or a disintegrant.

An embodiment according to the invention is directed to a pharmaceutical composition comprising (5,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, polymeric precipitation inhibitor, binder and disintegrant, for use in the protection of the liver against hepatotoxicity, the improvement of liver function, the protection/repair of liver injury, and/or the prophylaxis or treatment of a liver disorder/disease.

The pharmaceutical composition according to the invention can comprise a lubricant/glidant. The excipient can thus be a lubricant/glidant. Lubricants/glidants are materials preventing caking, improving the flow characteristics of granulates so that the flow is smooth and uniform, and reducing t the friction between surfaces in direct contact in order to allow for the tablet, granulate, etc. to be released from the casting mold or pressing mold, after compression. Lubricants/glidants include sodium benzoate, metallic stearate such as magnesium stearate, calcium stearate, or potassium stearate, stearic acid, high melting point waxes, inorganic lubricants/glidants such as silicon dioxide and talc and other lubricants/glidants such as sodium oleate, and polyethylene glycols. Preferably, the lubricant/glidant is talc or silicon dioxide. Due to the fact that lubricants/glidants have to be present on the surface of the granules as well as between the granules and parts of the equipment they are typically added during the last step prior to encapsulation or compression.

A preferred embodiment of the invention is therefore directed to a pharmaceutical composition comprising or consisting of (S,E)-methyl-7-(1-(2-(2-ethylbutylamino)-2- oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one lubricant/glidant, for use in the protection of the liver against hepatotoxicity, the improvement of liver function, the protection/repair of liver injury, and/or the prophylaxis or treatment of a liver disorder/disease.

A preferred embodiment according to the invention is directed to a pharmaceutical composition comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, polymeric precipitation inhibitor, binder, and lubricant/glidant, for use in the protection of the liver against hepatotoxicity, the improvement of liver function, the protection/repair of liver injury, and/or the prophylaxis or treatment of a liver disorder/disease.

A preferred embodiment according to the invention is directed to a pharmaceutical composition comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, wherein at least one excipient is selected from the group comprising or consisting of acidifier, polymeric precipitation inhibitor, binder, disintegrant, and lubricant/glidant, for use in the protection of the liver against hepatotoxicity, the improvement of liver function, the protection/repair of liver injury, and/or the prophylaxis or treatment of a liver disorder/disease.

Furthermore, the pharmaceutical composition according to the invention can also comprise as an excipient diluents/fillers/binders, sweetening agents, flavoring agents, buffering agents, antioxidants, emulsifiers, solubilizer/wetting agent and/or preservatives.

A suitable diluent/filler/binder is a substance which usually forms the largest part of the composition or dosage form. A suitable diluent/filler/binder includes sugars such as lactose, sucrose, mannitol and sorbitol; starches derived from wheat, corn, rice and potatoes; and cellulose such as microcrystalline cellulose, calcium hydrogen phosphate dihydrate, and calcium sulfate. Preferably, the diluent/filler/binder is cellulose and/or mannitol. Most preferably, the diluent/filler/binder is microcrystalline cellulose and/or mannitol. Preferably, the diluent/filler/binder is microcrystalline cellulose when the formulation is a tablet, and the diluent/filler/binder is mannitol when the pharmaceutical formulation is a capsule.

The addition of mannitol further increases the porosity and therefore wettability of the granules. A preferred embodiment of the invention is therefore directed to a pharmaceutical composition comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, for use in the protection of the liver against hepatotoxicity, the improvement of liver function, the protection/repair of liver injury, and/or the prophylaxis or treatment of a liver disorder/disease, wherein at least one excipient is a diluent/filler/binder.

The pharmaceutical composition according to the invention can comprise or consists of an acidifier, a polymeric precipitation inhibitor, a binder, a disintegrant, a lubricant/glidant and/or a diluent/filler/binder.

An embodiment of the invention is directed to a pharmaceutical composition comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, and at least one excipient, for use in the protection of the liver against hepatotoxicity, the improvement of liver function, the protection/repair of liver injury, and/or the prophylaxis or treatment of a liver disorder/disease, wherein at least one excipient is selected from the group comprising or consisting of acidifier, polymeric precipitation inhibitor, binder, disintegrant, lubricant/glidant and diluent/filler/binder.

An embodiment of the invention is directed to a systemic formulation containing or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, at least one acidifier, at least one polymeric precipitation inhibitor, at least one a binder, at least one disintegrant, at least one lubricant/glidant and at least one diluent/filler/binder, for use in the protection of the liver against hepatotoxicity, the improvement of liver function, the protection/repair of liver injury, and/or the prophylaxis or treatment of a liver disorder/disease.

The preferred pharmaceutical composition is provided in an administrable form suitable for oral application, such as tablets such as uncoated tablets, coated tablets, effervescent tablets, soluble tablets, chewable tablets, oral lyophilisates, lozenges, pastilles, compressed lozenges, sublingual tablets, buccal tablets, granules, effervescent granules and capsules. More preferably, the oral formulation is a tablet or capsule. Uncoated and coated, and capsules, either hard or soft are the most preferred pharmaceutical formulations.

In some embodiments, the invention refers to said pharmaceutical composition for use in the protection of the liver against hepatotoxicity, the improvement of liver function, the protection/repair of liver injury, and/or the prophylaxis or treatment of a liver disorder/disease, wherein the pharmaceutical composition is an oral formulation, preferably the oral formulation is a tablet, capsule, powder, or granule.

The pharmaceutical composition for use according to the invention may also comprise other ingredients for the capsule such as colorants of the capsule. Also in a tablet, a colorant as other ingredient can be present. Furthermore, components used for coating a tablet are also encompassed by the term “other ingredients”.

The shell of the capsule can comprise a colorant. As used herein, the term “colorant” includes pigments such as white pigments. The colorant can be among others iron oxide in particular iron(III)oxide, iron(II,III) oxide or hydrated ferric oxide or titanium dioxide.

“Tablet” means a compressed solid dosage form containing at least one active pharmaceutical ingredient with suitable excipients. The tablet can be produced by compressing mixtures or granulates obtained by wet granulation, dry granulation or compaction, which are known to the one skilled in the art.

The term “capsule” refers to a special container or shell composed of methylcellulose, polyvinyl alcohols or gelatins or denatured gelatins or starches, in which the active agents can be enclosed. Typically, hard shell capsules are prepared from hydroxypropyl methylcellulose or from mixtures of porcine bone and skin gelatins having comparatively high gel strength. The shell of the capsule can contain small amounts of colorants, opacifiers, softening agents and preservatives. "Soft shell capsules" contains gelatin as a basic polymer, one or more softening agents such as glycerol or sorbitol in a higher amount as well as water. In general, the amount of the softening agent is 20-30% by weight of the capsule shell, the amount of the gelatin is 40-45% by weight of the capsule shell, and amount of water is 30-35% by weight of the capsule shell. After the drying of the capsule, the amount of water is 7-8% by weight of the capsule shell.

The capsule shell can comprise gelatine, hydroxypropyl methylcellulose (HMPC), polysaccharides such as starch, and carrageenan; and/or synthetic polymers such as compolymers of polyvinylalcohol. Furthermore, the shell of the capsule can comprise a colorant. As used herein, the term "colorant" includes pigments such as white pigments. The colorant can be among others iron oxide in particular iron(III)oxide, iron(II,III) oxide or hydrated ferric oxide, titanium dioxide, natural dyes, azo and xanthane compounds. Moreover, the capsule shell may comprise a preservative such as p-hydroxybenzoic acid esters or means to improve the flavour such as ethylvanillin. In addition, the capsule shell can comprise a surfactant such a sodium lauryl sulfate.

"Powders" for compositions refer to powder mixtures/blends containing the active components and suitable excipients which can be suspended in water or juices prior to use. Spherical-shaped granules are also referred to pellets or beads.

"Granules" refer to dry and solid grains. Each grain represents an agglomerate of powder particles.

Furthermore, in order to further improve the performance of the pharmaceutical composition, the specific PSD (particle size distribution), and/or PSR (particle size range) can be adapted.

Therefore, in the use of the pharmaceutical composition according to the invention, said pharmaceutical composition comprising (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

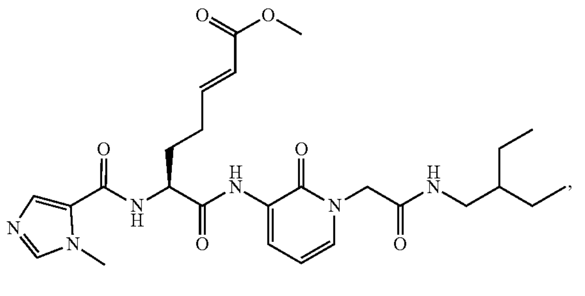

or a solvate, a hydrate or a pharmaceutically acceptable salt of formula (I), wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size range from 0.1 to 100 μm.

It is furthermore preferred that the particle size of the (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof is within the range of 0.1 μm to 100 μm, preferably in the range of 0.5 μm to 50 μm and more preferably in the range of 1.0 μm to 20 μm. Thus, the particle size range (PSR) of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof is from 0.1 μm to 100 μm, from 0.5 μm to 50 μm, or from 1.0 μm to 20 μm. Preferably, the particle size of the drug according to formula (I) is 0 μm.

Another preferred embodiment according to the invention is a pharmaceutical composition comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, and L-hydroxypropyl cellulose for use in the protection of the liver against hepatotoxicity, the improvement of liver function, the protection/repair of liver injury, and/or the prophylaxis or treatment of a liver disorder/disease, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size range from 0.1 μm to 100 μm.

Therefore, an embodiment according to the invention is directed to a pharmaceutical composition comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

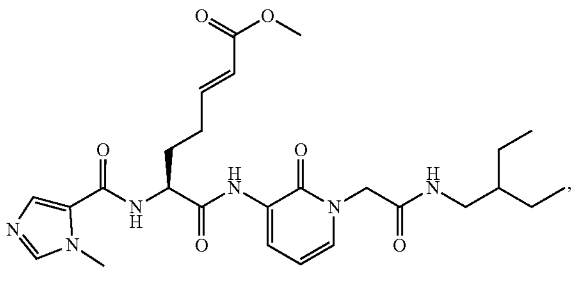

or an enantiomer, a solvate, a hydrate or a pharmaceutically acceptable salt of formula (I) for use in the protection of the liver against hepatotoxicity, the improvement of liver function, the protection/repair of liver injury, and/or the prophylaxis or treatment of a liver disorder/disease, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size distribution which is defined by d(0.95) 25 μm, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof is preferably micronized.

Moreover it is preferred that the particle size distribution of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof is characterized by d(0.1) from 0.1 to 5 μm, d(0.5) from 0.3 to 10 μm, d(0.95) from 3 to 25 μm, more preferably d(0.1) from 0.2 to 3 μm, d(0.5) from 0.4 to 7.5 μm and d(0.95) from 2 to 15 μm, and most preferably d(0.1) from 0.3 to 3 μm, d(0.5) from 0.5 to 5 μm and d(0.95) from 1 to 10 μm.

The particle size distribution is measured by laser light diffraction (Malvern analysis, sample dispersed in n-hexane and sorbitane monooleate). Thereby, the laser light is scattered in dependence of the particle size. A diffraction pattern results from the angle dependent scattered light intensity, the particle size can be calculated.

The parameter d(0.1) refers to the diameter at which 10% of the total volume of particles in the sample is comprised of particles with a diameter less than the indicated value or range of values when analysed by laser diffraction (Malvern analysis, sample dispersed in n-hexane and sorbitane monooleate). Thus d(0.1)=0.1 to 5 μm means that the upper limit of the particle size range defining the 10% of smallest particles in the sample is between 0.1 μm to 5 μm. Thus 10% of the total particles have a particle size of not more than d(0.1) meaning in this case that they have a maximum size of 0.1 μm to 5 μm.

Accordingly the parameter d(0.5) refers to the diameter at which 50% of the total volume of particles in the sample is comprised of particles with a diameter less than the indicated value or range of values when analysed by laser diffraction (Malvern analysis, sample dispersed in n-hexane and sorbitane monooleate). Thus d(0.5)=0.3 to 10 μm means that the upper limit of the particle size range defining the 50% of smallest particles in the sample is between 0.3 μm to 10 μm. Thus 50% of the total particles have a particle size of not more than d(0.5) meaning in this case that they have a maximum size of 0.3 μm to 10 μm.

Accordingly the parameter d(0.95) refers to the diameter at which 95% of the total volume of particles in the sample is comprised of particles with a diameter less than the indicated value or range of values when analysed by laser diffraction (Malvern analysis, sample dispersed in n-hexane and sorbitane monooleate). Thus d(0.95)=3 to 25 μm means that the upper limit of the particle size range defining the 95% of smallest particles in the sample is between 3 μm to 25 μm. Thus 95% of the total particles have a particle size of not more than d(0.95) meaning in this case that they have a maximum size of 3 μm to 25 μm.

Another embodiment of the present invention is directed to a pharmaceutical composition comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, and L-hydroxypropyl cellulose, for use in the protection of the liver against hepatotoxicity, the improvement of liver function, the protection/repair of liver injury, and/or the prophylaxis or treatment of a liver disorder/disease, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size distribution which is defined by d(0.95) 25 μm.

A preferred embodiment of the present invention is directed to a pharmaceutical composition comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, for use in the protection of the liver against hepatotoxicity, the improvement of liver function, the protection/repair of liver injury, and/or the prophylaxis or treatment of a liver disorder/disease, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size distribution which is defined by d(0.1) from 0.1 to 5 μm, d(0.5) from 0.3 to 10 μm, and d(0.95) from 3 to 25 μm.

A more preferred embodiment according to the invention is a pharmaceutical composition comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, and L-hydroxypropyl cellulose, for use in the protection of the liver against hepatotoxicity, the improvement of liver function, the protection/repair of liver injury, and/or the prophylaxis or treatment of a liver disorder/disease, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size distribution which is defined by d(0.1) from 0.1 to 5 μm, d(0.5) from 0.3 to 10 μm, and d(0.95) from 3 to 25 μm.

A still more preferred embodiment according to the invention is a pharmaceutical composition comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, and L-hydroxypropyl cellulose, for use in the protection of the liver against hepatotoxicity, the improvement of liver function, the protection/repair of liver injury, and/or the prophylaxis or treatment of a liver disorder/disease, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size distribution which is defined by d(0.1) from 0.2 to 3 μm, d(0.5) from 0.4 to 7.5 μm and d(0.95) from 2 to 15 μm.

A even more preferred embodiment according to the invention is a pharmaceutical composition comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, L-hydroxypropyl cellulose, sodium croscarmellose, and talc, for use in the protection of the liver against hepatotoxicity, the improvement of liver function, the protection/repair of liver injury, and/or the prophylaxis or treatment of a liver disorder/disease, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size distribution which is defined by d(0.1) from 0.1 to 5 μm, d(0.5) from 0.3 to 10 μm, and d(0.95) from 3 to 25 μm.

A particularly preferred embodiment according to the invention is a pharmaceutical composition comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, L-hydroxypropyl cellulose, sodium croscarmellose, talc, gelatine and titanium dioxide, for use in the protection of the liver against hepatotoxicity, the improvement of liver function, the protection/repair of liver injury, and/or the prophylaxis or treatment of a liver disorder/disease, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate have a particle size distribution which is defined by d(0.1) from 0.1 to 5 μm, d(0.5) from 0.3 to 10 μm, and d(0.95) from 3 to 25 μm.

Another particularly preferred embodiment of the invention is related to a pharmaceutical composition comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof, adipic acid, L-hydroxypropyl cellulose, povidone K25, sodium croscarmellose, microcrystalline cellulose and silicon dioxide, for use in the protection of the liver against hepatotoxicity, the improvement of liver function, the protection/repair of liver injury, and/or the prophylaxis or treatment of a liver disorder/disease, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate have a particle size distribution which is defined by d(0.1) from 0.1 to 5 μm, d(0.5) from 0.3 to 10 μm, and d(0.95) from 3 to 25 μm.

Therefore, an embodiment according to the invention is directed to a pharmaceutical composition comprising or consisting of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

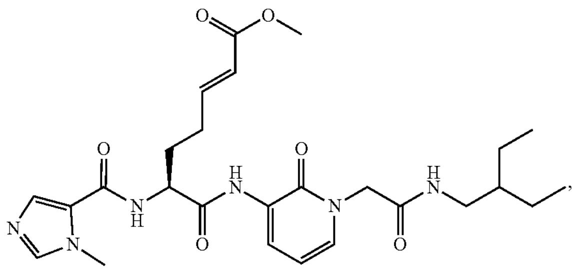

or an enantiomer, a solvate, a hydrate or a pharmaceutically acceptable salt of formula (I), wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size range from 0.1 to 100 μm, and a particle size distribution which is defined by d(0.95) 25 μm.

The pharmaceutical composition can comprise (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or enantiomer, solvate, a hydrate or a pharmaceutically acceptable salt, solvate or a hydrate in an amount of 0.1 wt % to 99 wt %, preferably 0.2 wt % to 90 wt %, more preferably 0.3 wt % to 85 wt %, even more preferably 0.4 wt % to 80 wt %, even more preferably 0.5 wt % to 75 wt %, even more preferably 0.6 wt % to 70 wt %, even more preferably 0.7 wt % to 65 wt %, even more preferably 0.8 wt % to 60 wt %, even more preferably 0.9 wt % to 55 wt %, even more preferably 1 wt % to 50 wt %, even more preferably 1 wt % to 45 wt %, even more preferably 1.25 wt % to 45 wt %, even more preferably 1.5 wt % to 40 wt %, even more preferably 1.75 wt % to 35 wt %, even more preferably 2 wt % to 34 wt %, even more preferably 2.25 wt % to 33 wt %, even more preferably 2.5 wt % to 32 wt %, and most preferably 2.5 wt % to 31 wt %, even more preferably 2.5 wt % to 30.5 wt %, and even more preferably 2.6 wt % to 30.3 wt %, even more preferably 3 wt % to 30 wt %, even more preferably 3.5 wt % to 29 wt %, even more preferably 4 wt % to 28 wt %, even more preferably 4 wt % to 27 wt %, even more preferably 4.5 wt % to 27 wt %, and most preferably 5 wt % to 27 wt %. "Wt %" ("weight percent") refers to the weight percent in the pharmaceutical composition.

The pharmaceutical composition can further comprise an amount of the acidifier in a range from 0.1 wt % to 80 wt %, preferably from 0.5 wt % to 77.5 wt %, more preferably from 1 wt % to 75 wt %, more preferably from 1.5 wt % to 72.5 wt %, more preferably from 2 wt % to 70 wt %, more preferably from 2.5 wt % to 62.5 wt %, more preferably from 3 wt % to 57.5 wt %, more preferably from 3.5 wt % to 55 wt %, even more preferably from 4 wt % to 55 wt %, even more preferably from 4.5 wt % to 55 wt %, even more preferably from 5 wt % to 54 wt %, even more preferably from 5.5 wt % to 53 wt %, even more preferably from 6 wt % to 52 wt %, even more preferably from 6.5 wt % to 51 wt %, even more preferably from 7 wt % to 50 wt %, even more preferably from 8 wt % to 49 wt %, even more preferably from 8.5 wt % to 49 wt %, and most preferably from 9 wt % to 49 wt %. "Wt %" ("weight percent") refers to the weight percent in the pharmaceutical composition.

The pharmaceutical composition can further comprise an amount of the polymeric precipitation inhibitor in a range from 0.1 wt % to 40 wt %, preferably 0.5 wt % to 39 wt %, more preferably 1 wt % to 38 wt %, still more preferably 1.25 wt % to 38 wt %, still more preferably 1.5 wt % to 37 wt %, still more preferably 1.75 wt % to 36 wt %, still more preferably 2 wt % to 35 wt %, still more preferably 1.5 wt % to 34 wt %, still more preferably 1.6 wt % to 33 wt %, still more preferably 1.7 wt % to 32 wt %, still more preferably 1.8 wt % to 31 wt %, still more preferably 3.5 wt % to 30 wt %, still more preferably 4 wt % to 29 wt %, still more preferably 4.5 wt % to 28.5 wt %, most preferably 5 wt % to 28.5 wt %.

The pharmaceutical composition can further comprise an amount of the binder in a range from 0 wt % to 40 wt %, preferably from 0 wt % to 35 wt %, more preferably from 0 wt % to 30 wt %, still more preferably from 0 wt % to 25 wt %, still more preferably from 0 wt % to 20 wt %, still more preferably from 0 wt % to 15 wt %, still more preferably from 0 wt % to 12 wt %, and most preferably from 0 wt % to 8.5 wt %.

The pharmaceutical composition can further comprise an amount of the disintegrant in a range from 0.1 wt % to 40 wt %, preferably from 1 wt % to 35 wt %, even more preferably from 2 wt % to 30 wt %, even more preferably from 2.5 wt % to 29 wt %, even more preferably from 3.0 wt % to 28 wt %, even more preferably from 3.5 wt % to 27 wt %, and most preferably from 3.5 wt % to 26.5 wt %.

The pharmaceutical composition can further comprise an amount of the lubricant/glidant in a range from 0.1 wt % to 10 wt %, preferably from, more preferably from 0.25 wt % to 9.5 wt %, still more preferably from 0.5 wt % to 9 wt %, still more preferably from 0.75 wt % to 8.5 wt %, still more preferably from 1 wt % to 8 wt %, still more preferably from 1.25 wt % to 7.5 wt %, still more preferably from 1.5 wt % to 7 wt %, and even more preferably 1.5 wt % to 6.5 wt %.

The pharmaceutical composition can further comprise an amount of diluent/filler/binder in a range from 0 wt % to 50% wt %, preferably from 1 wt % to 47.5% wt %, more preferred from 1.5 wt % to 45% wt %, more preferred from 2 wt % to 42.5% wt %, more preferred from 2.5 to 40 wt %, more preferred from 3 wt % to 38% wt %, more preferred 3.5 wt % to 38 wt %, more preferred 4 wt % to 38 wt %, more preferred to wt %, more preferred 4.5 wt % to 38 wt %, and even more preferred 5 wt % to 38 wt %

The pharmaceutical composition can further comprise an amount of other ingredients in a range from 5 wt % to 60 wt %, preferably from 6 wt % to 57.5 wt %, more preferably 7 wt % to 55 wt %, even more preferably from 8 wt % to 52.5 wt %, even more preferably from 9 wt % to 51 wt %, and most preferably 10 wt % to 50 wt % with respect to dosage form.

In a preferred embodiment, the invention refers to the pharmaceutical composition for use in the protection of the liver against hepatotoxicity, the improvement of liver function, the protection/repair of liver injury, and/or the prophylaxis or treatment of a liver disorder/disease, wherein the pharmaceutical composition comprises 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 3 wt % to 75 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

In a preferred embodiment, the invention refers to the pharmaceutical composition for use in the protection of the liver against hepatotoxicity, the improvement of liver function, the protection/repair of liver injury, and/or the prophylaxis or treatment of a liver disorder/disease, wherein the pharmaceutical composition comprises 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 3 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

Furthermore, in the pharmaceutical composition, a mass ratio of the acidifier relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof can range from 15 to 0.1 m/m, preferably from 14.5 to 0.2 m/m, more preferably from 14.0 to 0.3 m/m, still more preferably from 13.5 to 0.4 m/m, still more preferably from 13.0 to 0.5 m/m, still more preferably from 12.5 to 0.6 m/m, still more preferably from 12.0 to 0.7 m/m, still more preferably from 11.75 to 0.8 m/m, still more preferably from 11.5 to 0.9 m/m, still more preferably from 11.5 to 1.0 m/m, still more preferably from 11.5 to 1.1 m/m, still more preferably from 11.5 to 1.2 m/m, still more preferably from 11.5 to 1.3 m/m, still more preferably from 11.5 to 1.4 m/m, still more preferably from 11.5 to 1.5 m/m, still more preferably from 11.5 to 1.6 m/m, still more preferably from 11.5 to 1.7 m/m, and most preferably from 11.5 to 1.8 m/m.

Furthermore, in the pharmaceutical composition, a mass ratio of the polymeric precipitation inhibitor relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof can range from 0.05 to 10 m/m, preferably from 0.06 to 9.5 m/m, more preferably from 0.07 to 9.00 m/m, still more preferably from 0.08 to 8.50 m/m, still more preferably from 0.09 to 8.00 m/m, still more preferably from 0.1 to 7.5 m/m, still more preferably from 0.11 to 7.25 m/m, still more preferably from 0.12 to 7 m/m, still more preferably from 0.13 to 6.75 m/m, still more preferably from 0.14 to 6.5 m/m, still more preferably from 0.15 to 6.25 m/m, even more preferably from 0.16 to 6 m/m, even more preferably from 0.17 to 5.75 m/m, even more preferably from 0.18 to 5.5 m/m, even more preferably from 0.19 to 5.25 m/m, and most preferably from 0.20 to 5 m/m.

Furthermore, in the pharmaceutical composition, a mass ratio of the binder relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof can range from 0 to 10 m/m, preferably from 0.05 to 9.5 m/m, more preferably from 0.06 to 9.00 m/m, still more preferably from 0.07 to 8.50 m/m, still more preferably from 0.08 to 8.00 m/m, still more preferably from 0.09 to 7.5 m/m, still more preferably from 0.1 to 7.25 m/m, still more preferably from 0.11 to 7.00 m/m, still more preferably from 0.12 to 6.75 m/m, still more preferably from 0.13 to 6.50 m/m, still more preferably from 0.14 to 6.25 m/m, even more preferably from 0.15 to 6.00 m/m, even more preferably from 0.16 to 5.75 m/m, even more preferably from 0.17 to 5.50 m/m, even more preferably from 0.18 to 5.25 m/m, even more preferably from 0.19 to 5.5 m/m, even more preferably from 0.20 to 5 m/m, even more preferably from 0.20 to 4.5 m/m, even more preferably from 0.20 to 4 m/m, even more preferably from 0.20 to 3.5 m/m, even more preferably from 0.20 to 3 m/m, even more preferably from 0.20 to 2.5 m/m, and even more preferably from 0.20 to 2 m/m.

Furthermore, in the pharmaceutical composition, a mass ratio of the disintegrant relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof can range from 0.05 to 12 m/m, preferably from 0.06 to 11.5 m/m, more preferably from 0.07 to 11 m/m, still more preferably from 0.08 to 10.5 m/m, still more preferably from 0.09 to 10 m/m, still more preferably from 0.1 to 9.5 m/m, still more preferably from 0.11 to 9 m/m, still more preferably from 0.12 to 8.5 m/m, still more preferably from 0.13 to 8 m/m, still more preferably from 0.14 to 7.5 m/m, still more preferably from 0.15 to 7 m/m, even more preferably from 0.16 to 6.5 m/m, even more preferably from 0.17 to 5.5 m/m, even more preferably from 0.18 to 5 m/m, even more preferably from 0.19 to 5 m/m, and most preferably 0.2 to 5 m/m.

Furthermore, in the pharmaceutical composition, a mass ratio of the lubricant/glidant relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof can range from 0.05 to 2 m/m, preferably from 0.06 to 1.8 m/m, more preferably from 0.07 to 1.6 m/m, 0.08 to 1.4 m/m, still more preferably from 0.09 to 1.3 m/m, and most preferably from 0.1 to 1.2 m/m.

Furthermore, in the pharmaceutical composition, a mass ratio of the diluent/filler/binder relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof can range from 0 m/m to 20 m/m, more preferably 0.01 m/m to 17.5 m/m, more preferably 0.05 m/m to 15 m/m, more preferably 0.1 m/m to 0.125 m/m, more preferably 0.15 m/m to 10 m/m, more preferably 0.175 m/m to 7.5 m/m, more preferably 0.2 m/m to 6, more preferably 0.2 m/m to 5.5, more preferably 0.2 m/m to 5 m/m.

Furthermore, in the pharmaceutical composition, a mass ratio of other ingredients relative to the mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate or an enantiomer, a solvate, a hydrate or a pharmaceutically acceptable salt thereof can range from 0 to 30 m/m, preferably from 0.2 to 27.5 m/m, more preferably from 0.3 to 25 m/m, still more preferably from 0.35 to 22.5 m/m, even more preferably from 0.4 to 21 m/m, and most preferably from 0.45 to 20 m/m.

In a preferred embodiment, the invention refers to said pharmaceutical composition for use in the protection of the liver against hepatotoxicity, the improvement of liver function, the protection/repair of liver injury, and/or the prophylaxis or treatment of a liver disorder/disease, wherein the pharmaceutical composition comprises 1 to 15 m/m acidifier, 0.1 to 7 m/m polymeric precipitation inhibitor, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

Another aspect of the invention is directed to the use of an effective amount of a compound (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

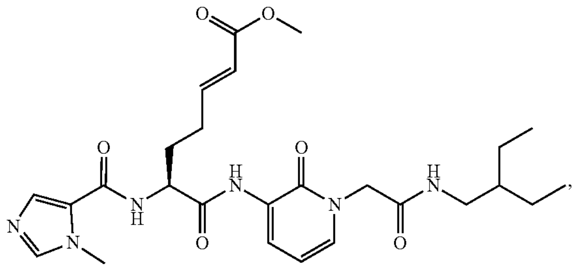

an enantiomer, a solvate, a hydrate or a pharmaceutically acceptable salt thereof for the manufacture of a pharmaceutical composition comprising the compound of the formula (I) as a hepatoprotectant.

In one embodiment, the invention is directed to the use of an effective amount of a compound (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate an enantiomer, a solvate, a hydrate or a pharmaceutically acceptable salt thereof, or said pharmaceutical composition in manufacture of a medicament for the protection of the liver against hepatotoxicity, the improvement of liver function, the protection/repair of liver injury, and/or the prophylaxis or treatment of a liver disorder/disease.

Preferably, the hepatotoxicity or the liver disorder/disease is caused by at least one hepatotoxicant, celiac disease, or a viral infection.

In particular, the at least one hepatotoxicant is selected from the group comprising or consisting of toxic chemicals, xenobiotics, anticancer drugs, immunosuppressant drugs, analgesic drugs, anti-inflammatory drugs, anti-tubercular drugs, biologicals, radiations, heavy metals, mycotoxin, galactosamine, and lipopolysaccharides, celiac disease associated with a specific genetic phenotype (HLA DQ2/DQ8) and a pathobiology promoted by transglutaminase 2 (TG2); and/or the viral infection with hepatitis A, B, C viruses.

In one embodiment, the invention is directed to the use of an effective amount of a compound of the formula (I), an enantiomer, a solvate, a hydrate or a pharmaceutically acceptable salt thereof, or said pharmaceutical composition in manufacture of a medicament for the protection of the liver against hepatotoxicity, the improvement of liver function, the protection/repair of liver injury, and/or the prophylaxis or treatment of a liver disorder/disease, wherein the compound reduces serum levels of at least one hepatic enzyme, preferably the at least one hepatic enzyme is selected from alanine aminotransferase (ALT), aspartate aminotransferase (AST), and alkaline phosphatase (ALP).

In one embodiment, the invention is directed to the use of an effective amount of a compound of the formula (I), an enantiomer, a solvate, a hydrate or a pharmaceutically acceptable salt thereof, or a pharmaceutical composition comprising 6-(1-methyl-1H-imidazole-5-carboxamido)-7-oxohept-2-enoate of the formula (I) in manufacture of a medicament for the protection of the liver against hepatotoxicity, the improvement of liver function, the protection/repair of liver injury, and/or the prophylaxis or treatment of a liver disorder/disease, wherein the liver disorder/disease is liver fibrosis, alcoholic hepatitis, nonalcoholic steatohepatitis (NASH), non-alcoholic fatty liver disease (NAFLD), cirrhosis, cholestatic liver diseases such as primary sclerosing cholangitis (PSC), and primary biliary cholangitis (PBC), autoimmune hepatitis (AIH), alcoholic steatohepatitis (ASH), or liver inflammation.

In one embodiment, the invention is directed to the use of an effective amount of said pharmaceutical composition in manufacture of a medicament for the protection of the liver against hepatotoxicity, the improvement of liver function, the protection/repair of liver injury, and/or the prophylaxis or treatment of a liver disorder/disease, wherein the pharmaceutical composition further comprises at least one polymeric precipitation inhibitor.

Preferably, the at least one polymeric precipitation inhibitor is selected from the group consisting of L-hydroxypropyl cellulose, hydroxypropyl cellulose, a combination of L-hydroxypropyl cellulose and hydroxypropyl cellulose, polyethylene glycol, poly(ethylene oxide)-poly (propylene oxide)-poly (ethylene oxide), polyvinyl alcohol, polyvinylpyrrolidone, carboxymethyl cellulose, methylcellulose, hydroxyethylcellulose, hydroxypropylmethylcellulose, ethylcellulose, polyvinyl caprolactam-polyvinyl acetate-polyethylene glycol graft copolymer (Soluplus®) and sodium carboxymethyl cellulose.

In one embodiment, the invention is directed to the use of an effective amount of said pharmaceutical composition in manufacture of a medicament for the protection of the liver against hepatotoxicity, the improvement of liver function, the protection/repair of liver injury, the protection/repair of liver injury, and/or the prophylaxis or treatment of a liver disorder/disease, wherein the pharmaceutical composition further comprises at least one acidifier and/or at least one binder.

Preferably, the at least one acidifier is selected from the group consisting of ascorbic acid, organic di-carboxylic acid such as oxalic acid, malonic acid, succinic acid, glutaric acid, tartaric acid, fumaric acid, maleic acid, malic acid, adipic acid, or glutamic acid, and organic tri-carboxylic acid such as citric acid, or sodium hydrogen citrate.

Preferably, the at least one binder is selected from the group consisting of sugar, sucrose, polysaccharides, xanthan gum, guar gum, carrageenan, starches derived from wheat, corn, rice and potatoes, preagglutinated (modified) starch derived from wheat, corn, rice and potatoes, sodium starch glycolate, natural gums, acacia gum, gelatin, tragacanth, derivatives of sea weed, alginic acid, sodium alginate, ammonium calcium alginate, cellulose, cellulose derivatives, hydroxypropyl cellulose, L-hydroxypropyl cellulose, low-substituted hydroxypropyl cellulose, methyl cellulose, sodium carboxymethylcellulose, hydroxypropyl methylcellulose, polyvinylpyrrolidone, povidone K25.

In one embodiment, the invention is directed to the use of an effective amount of said pharmaceutical composition in manufacture of a medicament for the protection of the liver against hepatotoxicity, the improvement of liver function, the protection/repair of liver injury, and/or the prophylaxis or treatment of a liver disorder/disease, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size distribution which is defined by d(0.95) 25 μm.

In some embodiments, the invention refers to the pharmaceutical composition for use, wherein the pharmaceutical composition is an oral formulation, preferably the oral formulation is a tablet, capsule, powder, or granule.

In a preferred embodiment, the invention is directed to the use of an effective amount of said pharmaceutical composition in manufacture of a medicament for the protection of the liver against hepatotoxicity, the improvement of liver function, the protection/repair of liver injury, and/or the prophylaxis or treatment of a liver disorder/disease, wherein the pharmaceutical composition comprises 1 to 15 m/m acidifier, 0.1 to 7 m/m polymeric precipitation inhibitor, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

In a preferred embodiment, the invention is directed to the use of an effective amount of said pharmaceutical composition in manufacture of a medicament for the protection of the liver against hepatotoxicity, the improvement of liver function, the protection/repair of liver injury, and/or the prophylaxis or treatment of a liver disorder/disease, wherein the pharmaceutical composition comprises 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 3 wt % to 75 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

In a preferred embodiment, the invention is directed to the use of an effective amount of said pharmaceutical composition in manufacture of a medicament for the protection of the liver against hepatotoxicity, the improvement of liver function, the protection/repair of liver injury, and/or the prophylaxis or treatment of a liver disorder/disease, wherein the pharmaceutical composition comprises 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 3 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

Another aspect of the invention is directed to a method of the protection of the liver against hepatotoxicity, the improvement of liver function, the protection/repair of liver injury, and/or the prophylaxis or treatment of a liver disorder/disease comprising administering to a subject an effective amount of a compound (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate of the formula (I):

(I)

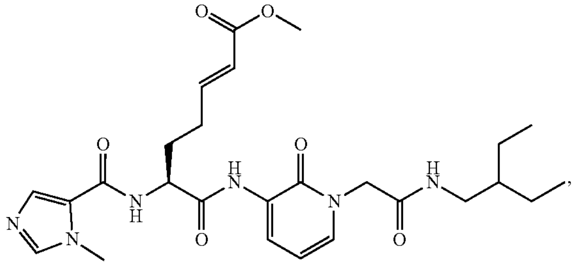

an enantiomer, a solvate, a hydrate or a pharmaceutically acceptable salt thereof, or a pharmaceutical composition comprising the compound of the formula (I) as a hepatoprotectant.

Preferably, the hepatotoxicity or the liver disorder/disease is caused by at least one hepatotoxicant, celiac disease, or a viral infection.

The term "a subject" used herein is a mammal, preferably a human.

In particular, the at least one hepatotoxicant is selected from the group comprising or consisting of toxic chemicals, xenobiotics, anticancer drugs, immunosuppressant drugs, analgesic drugs, anti-inflammatory drugs, anti-tubercular drugs, biologicals, radiations, heavy metals, mycotoxin, galactosamine, and lipopolysaccharides; celiac disease associated with a specific genetic phenotype (HLA DQ2/DQ8) and a pathobiology promoted by transglutaminase 2 (TG2); and/or the viral infection with hepatitis A, B, C viruses.

In one embodiment, the invention is directed to the method of the protection of the liver against hepatotoxicity, the improvement of liver function, the protection/repair of liver injury, and/or the prophylaxis or treatment of a liver disorder/disease comprising administering to a subject an effective amount of the compound of the formula (I), the enantiomer, the solvate, the hydrate or the pharmaceutically acceptable salt thereof, or said pharmaceutical composition, wherein the compound of the formula (I), reduces serum levels of at least one hepatic enzyme, preferably the at least one hepatic enzyme is selected from alanine aminotransferase (ALT), aspartate aminotransferase (AST), and alkaline phosphatase (ALP).

In one embodiment, the invention is directed to the method of the protection of the liver against hepatotoxicity, the improvement of liver function, the protection/repair of liver injury, and/or the prophylaxis or treatment of a liver disorder/disease, comprising administering to a subject an effective amount of the compound of the formula (I), the enantiomer, the solvate, the hydrate or the pharmaceutically acceptable salt thereof, or said pharmaceutical composition comprising the compound of the formula (I), wherein the liver disorder/disease is liver fibrosis, alcoholic hepatitis, nonalcoholic steatohepatitis (NASH), non-alcoholic fatty liver disease (NAFLD), cirrhosis, cholestatic liver diseases such as primary sclerosing cholangitis (PSC), and primary biliary cholangitis (PBC), autoimmune hepatitis (AIH), alcoholic steatohepatitis (ASH), or liver inflammation.

In one embodiment, the invention is directed to the method of the protection of the liver against hepatotoxicity, the improvement of liver function, the protection/repair of liver injury, and/or the prophylaxis or treatment of a liver disorder/disease, comprising administering to a subject an effective amount of said pharmaceutical composition comprising the compound of the formula (I), wherein the pharmaceutical composition further comprises at least one polymeric precipitation inhibitor.

Preferably, the at least one polymeric precipitation inhibitor is selected from the group consisting of L-hydroxypropyl cellulose, hydroxypropyl cellulose, a combination of L-hydroxypropyl cellulose and hydroxypropyl cellulose, polyethylene glycol, poly(ethylene oxide)-poly (propylene oxide)-poly (ethylene oxide), polyvinyl alcohol, polyvinylpyrrolidone, carboxymethyl cellulose, methylcellulose, hydroxyethylcellulose, hydroxypropylmethylcellulose, ethylcellulose, polyvinyl caprolactam-polyvinyl acetate-polyethylene glycol graft copolymer (Soluplus®) and sodium carboxymethyl cellulose.

In one embodiment, the invention is directed to the method of the protection of the liver against hepatotoxicity, the improvement of liver function, the protection/repair of liver injury, and/or the prophylaxis or treatment of a liver disorder/disease, comprising administering to a subject an effective amount of said pharmaceutical composition, wherein the pharmaceutical composition further comprises at least one acidifier and/or at least one binder.

Preferably, the at least one acidifier is selected from the group consisting of ascorbic acid, organic di-carboxylic acid such as oxalic acid, malonic acid, succinic acid, glutaric acid, tartaric acid, fumaric acid, maleic acid, malic acid, adipic acid, or glutamic acid, and organic tri-carboxylic acid such as citric acid, or sodium hydrogen citrate.

Preferably, the at least one binder is selected from the group consisting of sugar, sucrose, polysaccharides, xanthan gum, guar gum, carrageenan, starches derived from wheat, corn, rice and potatoes, preagglutinated (modified) starch derived from wheat, corn, rice and potatoes, sodium starch glycolate, natural gums, acacia gum, gelatin, tragacanth, derivatives of sea weed, alginic acid, sodium alginate, ammonium calcium alginate, cellulose, cellulose derivatives, hydroxypropyl cellulose, L-hydroxypropyl cellulose, low-substituted hydroxypropyl cellulose, methyl cellulose, sodium carboxymethylcellulose, hydroxypropyl methylcellulose, polyvinylpyrrolidone, povidone K25.

In one embodiment, the invention is directed to the method of the protection of the liver against hepatotoxicity, the improvement of liver function, the protection/repair of liver injury, and/or the prophylaxis or treatment of a liver disorder/disease, comprising administering to a subject an effective amount of said pharmaceutical composition, wherein (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate particles have a particle size distribution which is defined by d(0.95) 25 μm.

In some embodiments, the invention refers to the method of the protection of the liver against hepatotoxicity, the improvement of liver function, the protection/repair of liver injury, and/or the prophylaxis or treatment of a liver disorder/disease, comprising administering to a subject an effective amount of said pharmaceutical composition, wherein the pharmaceutical composition is an oral formulation, preferably the oral formulation is a tablet, capsule, powder, or granule.

In a preferred embodiment, the invention is directed to the method of the protection of the liver against hepatotoxicity, the improvement of liver function, the protection/repair of liver injury, and/or the prophylaxis or treatment of a liver disorder/disease, comprising administering to a subject an effective amount of said pharmaceutical composition, wherein the pharmaceutical composition comprises 1 to 15 m/m acidifier, 0.1 to 7 m/m polymeric precipitation inhibitor, wherein m/m (mass ratio) of said compounds is calculated relative to mass of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

In a preferred embodiment, the invention is directed to the method of the protection of the liver against hepatotoxicity, the improvement of liver function, the protection/repair of liver injury, and/or the prophylaxis or treatment of a liver disorder/disease, comprising administering to a subject an effective amount of the pharmaceutical composition, wherein the pharmaceutical composition comprises 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 3 wt % to 75 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

In a preferred embodiment, the invention is directed to the method of the protection of the liver against hepatotoxicity, the improvement of liver function, the protection/repair of liver injury, and/or the prophylaxis or treatment of a liver disorder/disease, comprising administering to a subject an effective amount of the pharmaceutical composition, wherein the pharmaceutical composition comprises 0.1 wt % to 45 wt % (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 3 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

EXAMPLES

Example 1

Figure 1:
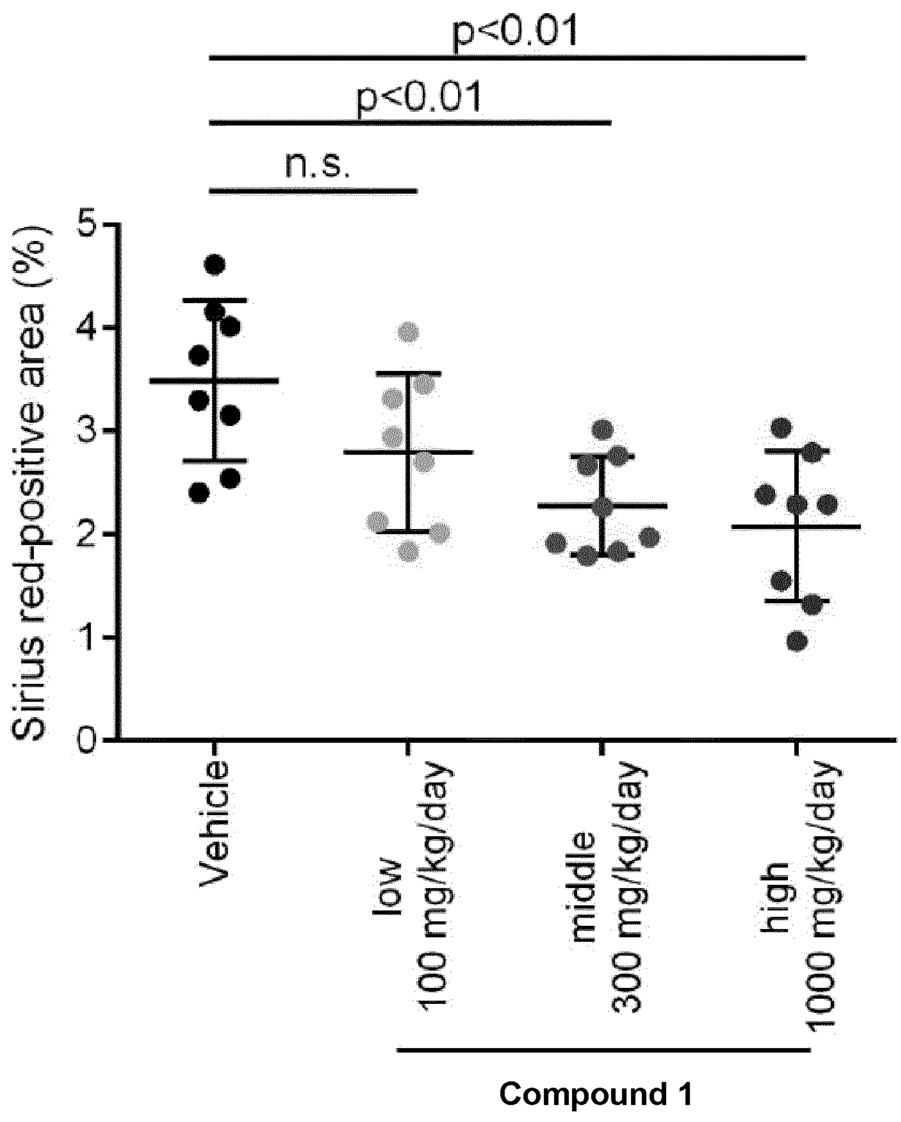
FIG. 1 shows (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (compound 1) in the UUO-model.

Preparation of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (Compound of formula (I))

Example 1.1 Preparation of 6-amino-hept-2-en-dicarboxyl Acid Derivatives

(S)-1-tert-Butyl 5-methyl 2-(tert-butoxycarbonylamino)pentanedioate

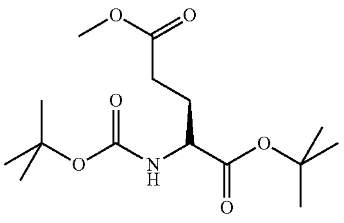

Molecular formula: C15H27N06
Molecular weight: 317.88

12.0 g of Boc-Glu-OtBu (39.6 mmol) are dissolved in 200 mL of DMF. Under argon atmosphere, 7.09 g of cesium carbonate (21.8 mmol, 0.55 eq.) are added and the resulting suspension is stirred for 1 hour at RT. After this time, 2.47 mL of methyl iodide (39.6 mmol) are added and stirred at RT overnight. The solvent is removed in vacuo and the obtained residue is taken up in 400 mL of ethyl acetate. The undissolved solid is filtered and the filtrate is washed with respectively 75 mL of 10% citric acid, 10% $NaHCO_3$ solution and brine 3 times. After drying of the organic phase over $Na_2SO_4$ the solvent is removed in vacuo. The product is obtained as yellow oil. The product can be used without further purification in the following reaction.

Yield: 13.4 g, >100%

ESI-MS: 340.2 $[M+Na]^+$

(S)-1-tert-Butyl 5-methyl 2-(bis(tert-butoxycarbonyl)amino)pentanedioate

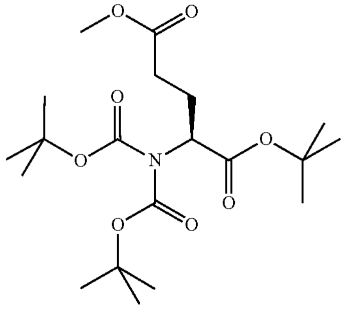

Molecular formula: C20H35NO8
Molecular weight: 417.49

13.4 g of Boc-Glu(OMe)-OtBu (~39.6 mmol) are dissolved in 30 mL of acetonitrile and treated with 986 mg of DMAP (7.91 mmol, 0.2 eq). Under nitrogen atmosphere a solution of 17.6 g of di-tert-butylbicarbonate (77.1 mmol, 2 eq) in 100 mL of acetonitrile is added. After stirring overnight, the solvent is removed in vacuo and the obtained crude product is purified by chromatography on silica gel (column: 31*6.0 cm, petroleum ether/ethyl acetate 9:1)

Column chromatography: collected in 250 mL fractions, product: fractions 6-13

TLC control: petroleum ether/ethyl acetate 8:2, $R_f$=0.70

Yield: 13.7 g, 32.8 mmol, 83%

ESI-MS: 440.3 $[M+Na]^+$

(S)-tert-Butyl 2-(bis(tert-butoxycarbonyl)amino)-5-oxopentanoate

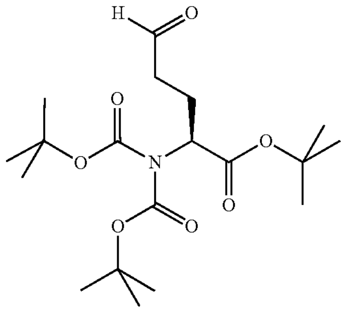

Molecular formula: C19H33NO7
Molecular weight: 387.47

13.7 g of $Boc_2$-Glu(OMe)-OtBu (32.8 mmol) are dissolved in 200 mL of absolute diethylether and cooled to −78° C. under argon atmosphere. At this temperature 36.1 mL (36.1 mmol, 1.1 eq) of a solution of diisobutyl aluminum hydride (1 M in hexane) is dropped slowly. After the addition, the solution is stirred for further 15 min at −78° C., before the reacting mixture is quenched by addition of 50 mL of water at the same temperature. With vigorous stirring, it is warmed up to RT and the cloudy solution is filtered over Celite. The filtrate is concentrated in dryness and the residual water is removed by codestillation with toluene. Light-colored oil is obtained and it is used without further purification in the subsequent reaction.

TLC control: petroleum ether/ethyl acetate 8:2, $R_f$=0.54

Yield: 13.3 g, >100% (purity 86.1%)

500-MHz-$^1$H-NMR-cosy ($DMSO_{d6}$): δ[ppm]=9.65 (s, 1H, H-4), 4.63 (dd, 1H, H-1, $J_{1/2a}$=4.8 Hz, $J_{1/2b}$=9.85 Hz), 2.51-2.50 (m, 1H, H-$3_a$), 2.48-4.40 (m, 1H, H-$3_b$), 2.27-2.20 (m, 1H, H-2a), 1.98-1.91 (m, 1H, H-$2_b$), 1.44 (s, 18H, 6*$CH_3$(Boc)), 1.92 (s, 9H, 3*$CH_3$(O-tBu)

ESI-MS: 410.4 $[M+Na]^+$ (S,E)-7-tert-Butyl 1-methyl 6-(bis(tert-butoxycarbonyl)amino)hept-2-enedioate

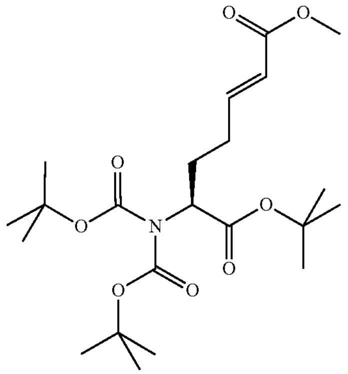

Molecular formula: C22H37NO8
Molecular weight: 443.53

13.2 g of $Boc_2$-Glu(H)-OtBu (~32.8 mmol) are provided in 20 mL of dried benzene and under argon atmosphere at RT a solution of 11.2 g of (methoxycarbonylmethylen)-triphenyl-phosphorane (32.8 mmol) is added. After stirring overnight, the solvent is removed in vacuo and the obtained oily residue is purified by chromatography on silica gel (column: 39*6.0 cm, petroleum ether/ethyl acetate 9:1).

Column chromatography: collected in 250 mL fractions, product: fractions 2-12

TLC control: petroleum ether/ethyl acetate 8:2, $R_f$=0.54

Yield: 12.0 g, 27.1 mmol, 83%

500-MHz-$^1$H-NMR-cosy ($DMSO_{d6}$): δ[ppm]=6.66 (dt, 1H, H-4, $J_{4/3}$=6.8 Hz $J_{4/5}$=15.9 Hz), 5.64 (d, 1H, H-5, $J_{5/4}$=15.9 Hz), 4.45-4.2 (m, 1H, H-1), 3.44 (s, 3H, $CH_3$-6), 2.01-1.95 (m, 2-H, H-$3_a$, H-$3_b$), 1.95-1.86 (m, 1H, H-2), 1.78-1.67 (m, 1H, H-$2_b$), 1.24 (s, 18H, 6*$CH_3$(Boc)), ESI-MS: 466.3 $[M+Na]^+$ (S,E)-2-(tert-Butoxycarbonylamino)-7-methoxy-7-oxohept-5-enoic acid (1a1)

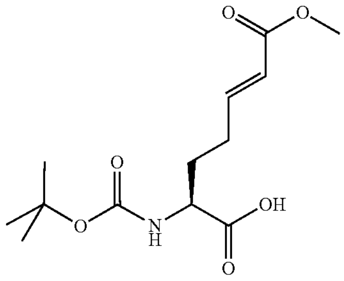

Molecular formula: C13H21NO6
Molecular weight: 287.31

7.0 g of (S,E)-7-tert-butyl 1-methyl 6-(bis(tert-butoxycarbonyl)amino)hept-2-enedioate (15.8 mmol) are dissolve in 40 mL of dichloromethane and added into the solution of 70 mL of trifluoroacetic acid. It is stirred at RT for 4 h. The solvent is removed in vacuo and the green residue is dried under high vacuum. The obtained oil is further used without purification. By successive addition of DIPEA the pH value is adjusted to ca. 7.

The oil is taken up in 50 mL of DMF and treated with 5.37 mL of DIPEA. 4.08 g of Boc-OSu (18.9 mmol, 1.2 eq) are added and stirred at RT overnight. The solvent is removed in vacuo and the residue is suspended in 130 mL of 5% $KHSO_4$ solution. It is extracted with ethyl acetate (1×150 mL, 2×100 mL) and the corrected organic phases are washed with brine (75 mL). After drying of the organic phase over $Na_2SO_4$ the solvent is removed in vacuo. The residue is purified by chromatography on silica gel (column: 13*6.0 cm, toluene/ethyl acetate 65:35, 0.5% acetic acid). Colorless oil is obtained.

Column chromatography: collected in 200 mL fractions, product: fractions 2-5, first running 500 mL TLC control: toluene/ethyl acetate 1:1, 0.5% acetic acid, $R_f$=0.35

Yield: 4.04 g, 14.1 mmol, 89% (purity 88.6%); ESI-MS: 310.1 $[M+Na]^+$

Example 1.2 Preparation of Pyridinone Derivatives

Benzyl-3-hydroxypyridin-3-yl-carbamate

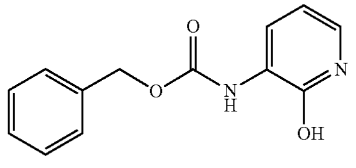

Molecular formula: C13H12N2O3
Molecular weight: 244.25

15 g of 2-hydroxy-nicotinic acid (108 mmol) are suspended in 180 mL of dried dioxane. After addition of 14.9 mL of triethylamine (108 mmol), the suspension is clear extensively. 24 mL of diphenyl phosphoryl azide (DPPA, 108 mmol) are added and the reaction solution is refluxed (130° C.) under argon atmosphere. Thereby, a gas emission is observed. After 16 h, further 16.3 mL of TEA and 12.8 mL of benzyl alcohol (117 mmol, 1.1 eq) are added successively and refluxed for further 24 h.

The solvent is removed in vacuo and the obtained brown residue is taken up in a mixture of 300 mL of DCM and 300 mL of brine. By 1M HCl solution the pH value is adjusted to ca. 1 (ca. 22 mL), the phases are separated and subsequently the water phase is extracted two times with each 200 mL of DCM. The corrected organic phases are washed with 10% $NaHCO_3$ solution (3×150 mL) and brine (1×150 mL), dried over $Na_2SO_4$, filtered and concentrated in vacuo in dryness. The obtained brown solid is recrystallized from 300 mL of methanol.

TLC control: DCM/MeOH 9:1, Rf=0.70

Yield: 16.2 g, 66.4 mmol, 62% (pale brown, felt-like solid)

ESI-MS: 245.1 $[M+H]^+$ tert-Butyl 2-(3-(benzyloxycarbonylamino)-2-oxopyridin-1(2H)-yl)acetate

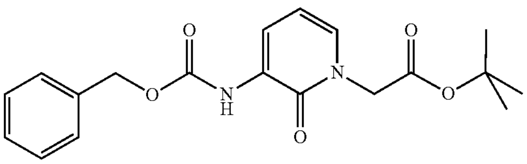

Molecular formula: C19H22N2O5
Molecular weight: 358.39

16.2 g of benzyl-3-hydroxypyridin-3-yl-carbamate (66.4 mmol) are suspended in 900 mL of absolute THF and cooled to 0° C. under argon atmosphere and 2.92 g of NaH (60% in mineral oil, 73.1 mmol, 1.1 eq) are added. To the resulting solution after the end of gas emission (ca. 15 min) 13.7 mL of bromoacetic acid tert-butylester (89.7 mmol, 1.35 eq) are added. It is stirred still for 15 minutes at 0° C. and subsequently at RT overnight. The reaction mixture is filtered and the filtrate is concentrated in dryness. The residue is taken up in 5 mL of ethyl acetate and treated with ca. 50 mL of diethylether and the resulting suspension is precipitated in the refrigerator overnight. The crystals are filtered off and washed with a little amount of ether.

The filtrate is concentrated and purified by chromatography on silica gel. (bed: 20×6 cm, eluent: petroleum ether/ethyl acetate=8/2)

Column chromatography: collected in 250 mL fractions, product: fractions 10-25

TLC control: petroleum ether/ethyl acetate=7/3, Rf=0.46

Yield: 19.3 g, 54.0 mmol, 81%

ESI-MS: 359.1 $[M+H]^+$

2-(3-(Benzyloxycarbonylamino)-2-oxopyridin-1(2H)-yl)acetic acid

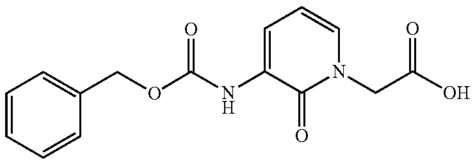

Molecular formula: C15H14N2O5
Molecular weight: 302.28

4.00 g of tert-butyl 2-(3-(benzyloxycarbonylamino)-2-oxopyridin-1(2H)-yl)acetate (11.2 mmol) are dissolved in 50 mL of dichloromethane and treated with 50 mL of trifloroacetic acid. It is stirred at RT for 3 h, before the volatile components are removed in vacuo. After drying under high vacuum a brown solid is obtained and it is suitable for the further use without purification.

Yield: 3.70 g, >100%

ESI-MS: 303.2 $[M+H]^+$

Benzyl-1-(2-(2-ethylbutylamino)-2-oxoethyl)-2-oxo-1,2-dihydro-pyridin-3-ylcarbamate

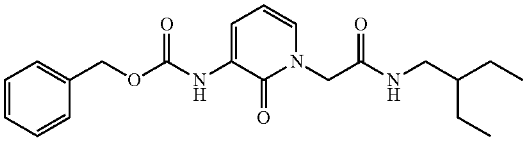

Molecular formula: C21H27N3O4
Molecular weight: 385.46

A mixture of 3.70 g of 2-(3-(benzyloxycarbonylamino)-2-oxopyridin-1(2H)-yl)acetic acid (~11.2 mmol), 3.58 g of TBTU (11.2 mmol), 1.51 g of HOBt (11.2 mmol) is dissolved in 60 mL of DMF. By addition of 5.70 mL of DIPEA (33.5 mmol, 3 eq) a pH value is adjusted to ~10. 1.50 mL of 2-ethyl-butylamine (11.2 mmol) is added and the mixture is stirred at RT overnight. The solvent is removed in vacuo and the obtained residue is taken up in 300 mL of DCM and subsequently washed with 10% citric acid (3×75 mL), saturated $NaHCO_3$ solution (3×75 mL) and brine (75 mL). The organic phase is dried over $Na_2SO_4$, filtered and concentrated in dryness. Pale brown solid is obtained and it is suitable for further processing without further purification.

Yield: 5.22 g, >100%

ESI-MS: 386.3 $[M+H]^+$

2-(3-Amino-2-oxopyridin-1(2H)-yl)-N-(2-ethylbutyl)acetamide (2a)

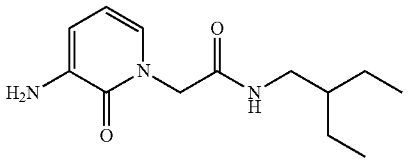

Molecular formula: C13H21N3O2
Molecular weight: 251.32

5.22 g of benzyl-1-(2-(2-ethylbutylamino)-2-oxoethyl)-2-oxo-1,2-dihydro-pyridin-3-ylcarbamate (2.4, ~11.2 mmol) are dissolved under nitrogen atmosphere in 60 mL of methanol. To this solution, 500 mg of Pd/C (10%) are added and stirred under hydrogen atmosphere at atmosphere pressure for 2.5 h. The catalysis is separated by filtration over silica gel, before the solvent is removed in vacuo. Dark oil is obtained and it is suitable for further processing without further purification.

Yield: 3.62 g, >100%

ESI-MS: 252.2 $[M+H]^+$

Example 1.3 Preparation of (S,E)-Methyl 6-(tert-butoxycarbonylamino)-7-(1-(2-(2-ethylbutylamino)-2-oxoethyl)-2-oxo-1,2-dihydro-pyridin-3-ylamino)-7-oxohept-2-enoate

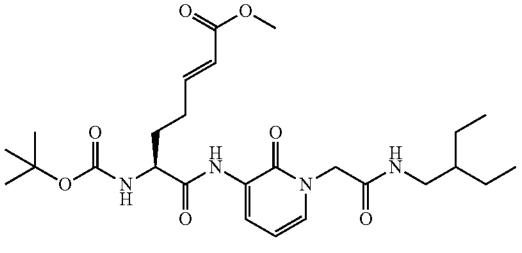

Molecular formula: C26H40N4O7;
Molecular weight: 520.62

A solution of 3.36 g of 2-(3-amino-2-oxopyridin-1(2H)-yl)-N-(2-ethylbutyl)acetamide (2a, ~10.4 mmol) in 20 mL of DMF is provided. To this solution, a solution of 2.97 g of (S,E)-2-(tert-butoxycarbonylamino)-7-ethoxy-7-oxohept-5-enoic acid (1a1, 10.4 mmol), 3.93 g of HATU (10.4 mmol) and 3.52 mL of DIPEA (20.7 mmol, 2 eq) in 40 mL of DMF is added. By successive addition of DIPEA the pH value is adjusted to ca. 7. The reaction mixture is stirred at 40° C. for 2.5 hours, as well as at RT overnight, before the solvent is removed in vacuo. The obtained brown residue is taken up in 250 mL of ethyl acetate and subsequently washed with 10% citric acid (3×75 mL), saturated $NaHCO_3$ solution (3×75 mL) and brine (75 mL). The organic phase is dried over $Na_2SO_4$ and concentrated in vacuo in dryness. The residue is purified by chromatography on silica gel (bed: 13×6 cm, eluent: toluene/acetone=7/3).

Column chromatography: 150 mL first running, corrected in 40 mL fractions, product: fraction 6-15

TLC control: DCM/MeOH=97/3, Rf=0.40

Yield: 3.34 g, 6.42 mmol, 62%

ESI-MS: 543.4 $[M+Na]^+$ (S,E)-Methyl 7-(1-(2-(2-ethylbutylamino)-2-oxo-ethyl)-2-oxo-1,2-dihydro-pyridin-3-ylamino)-6-(1-methyl-1H-imidazole-5-carboxamido)-7-oxohept-2-enoate (Compound of formula (I))

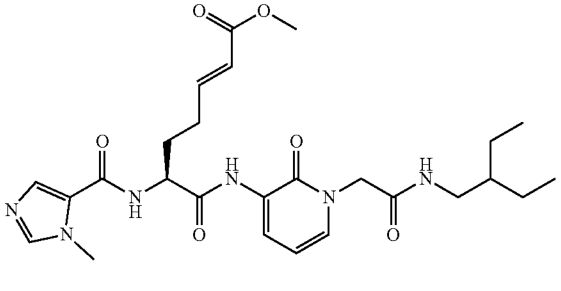

Molecular formula: C26H36N6O6;
Molecular weight: 528.60

3.14 g of (S,E)-methyl 6-(tert-butoxycarbonylamino)-7-(1-(2-(2-ethylbutylamino)-2-oxoethyl)-2-oxo-1,2-dihydro-pyridin-3-ylamino)-7-oxohept-2-enoate (3.1, 6.03 mmol) are dissolved in a mixture of 25 mL of dichloromethane and 35 mL of TFA and stirred for 3 hours at RT, before the volatile components are removed in vacuo. The obtained brown oil is dried under high vacuum and dissolved in 10 mL of DMF and 1.03 mL of DIPEA (6.03 mmol) is added. To this a solution of 2.29 g of HATU (6.03 mmol) and 1.03 mL of DIPEA (6.03 mmol) in 30 mL of DMF is added. By successive addition of DIPEA the pH value is adjusted to ca. 7. It is stirred overnight at RT. The residue is taken up in 200 mL of ethyl acetate and subsequently washed with 10% citric acid, saturated $NaHCO_3$ solution and brine (each 75 mL). The organic phase is dried over $Na_2SO_4$, filtered and concentrated in vacuo in dryness. The residue is purified by chromatography on silica gel (bed: 12×6 cm, eluent: DCM/MeOH=97/3, after 2 Liters 95/5).

Column chromatography: 1000 mL first running, corrected in 50 mL fractions, product: fraction 43-66

TLC control: DCM/MeOH=97/3, $R_f$=0.30

Yield: 1.42 g, 2.69 mmol, 45%

ESI-MS: 551.3 $[M+Na]^+$ $^1$H-NMR (DMSO-d6, 500 MHz): δ[ppm]=9.29 (s, 1H), 8.63 (d, 1H), 8.21 (dd, 1H), 8.04 (t, 1H), 7.75 (d, 2H), 7.33 (dd, 1H), 6.93 (dt, 1H, J=15.63; 6.93), 6.25 (t, 1H), 5.86 (d, 1H, J=15.69), 4.58 (s, 2H), 3.79 (s, 3H), 3.62 (s, 3H), 3.01 (t, 2H), 2.33 (m, 2H), 2.03 (m, 1H), 1.90 (m, 1H), 1.26 (m, 5H), 0.83 (t, 6H)

Example 2

Study in a Unilateral Ureteral Obstruction Model (UUO-Model) for Nephritic Fibrosis The anti-fibrotic effect of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (compound of formula (I)) in the kidney was investigated in an UUO-model in the C57BL/6-mouse. In a UUO-model, in one of the kidneys fibrosis is induced by ligation of one ureter. The other kidney remains functional. The pathophysiology of the UUO-model resembles the chronic nephropathy in humane (Chronic Kidney Disease, CKD).

Groups of 8 UUO-mice were treated directly after ligation of the ureter over a time period of two weeks with three different dosages of said compound: 100 mg/kg body weight, 300 mg/kg body weight, and 1000 mg/kg body weight. The daily dosage was administered orally as a suspension at intervals of 8 hours. In a control group, the UUO-mice were treated in same way but merely with the vehicle methyl cellulose. After the end of the treatment, the histopathological investigation of the kidney tissue as well as the determination of the amount of hydroxyproline in the kidney was performed. Furthermore, an immune-histochemical localisation of the complex of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate and TG2 by means of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate-specific antibody was carried out.

Figure 2:
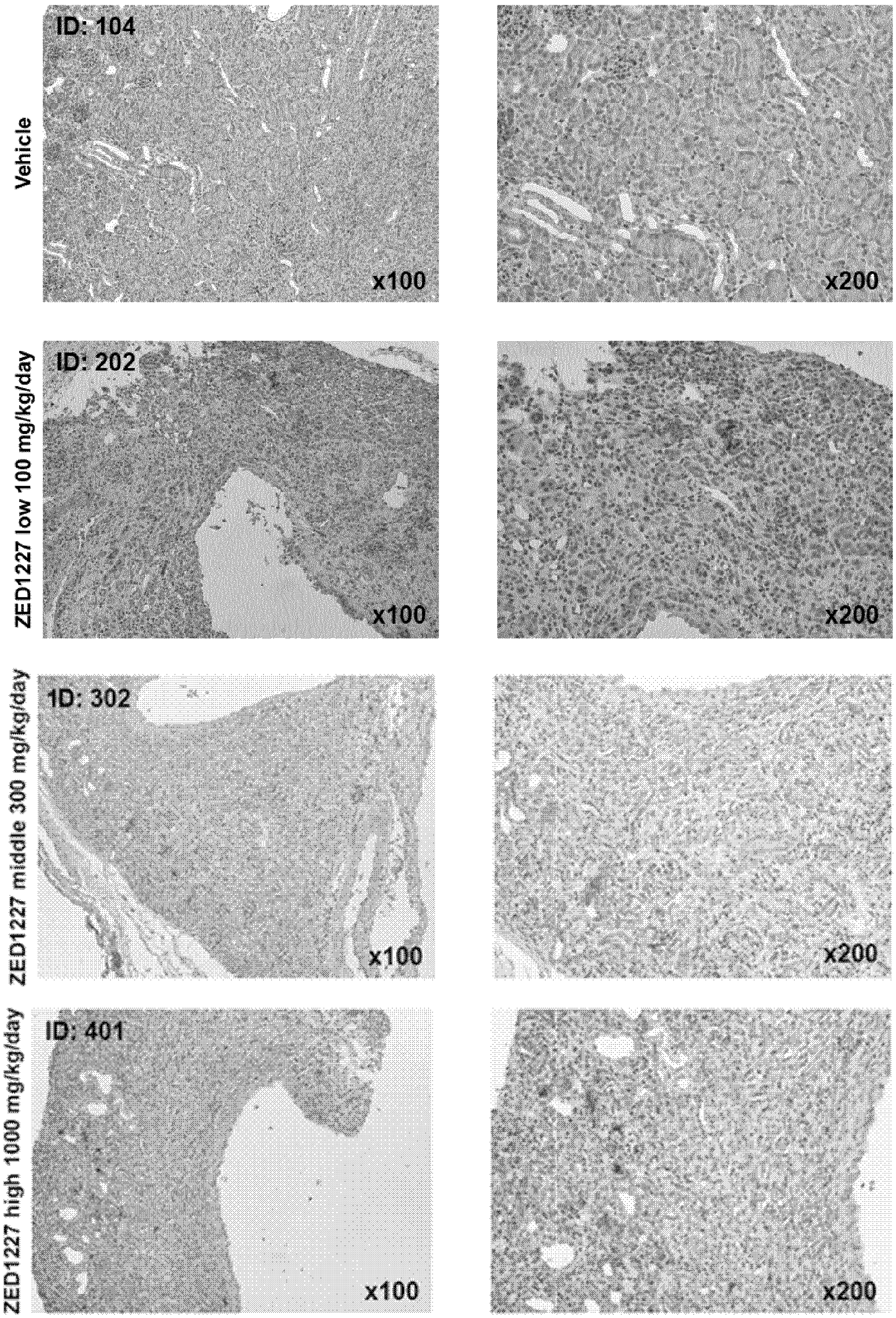
FIG. 2 shows immune-histochemical evidence of the complex of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (compound 1) and TG2 in the kidney tissue at different dosages.

Results: The treatment with (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7- oxohept-2-enoate results in a significant, marked, dosage dependent reduction of the fibrotic area of the kidney. The hydroxyproline content remained unaffected. The effect of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate in the UUO-model is shown in FIG. 1. The immune-histochemical localisation of the complex of compound of formula (I) and TG2 in the kidney tissue at different dosages can be seen in FIG. 2.

Conclusion: The remarkable improvement of the kidney histology in comparison to the control shows that the compound of the formula (I) suppressed both fibrosis and fibrogenesis. The effects and underlying mechanism in the kidney are possibly analog to the antifibrotic effects and mechanism in the liver.

The immune-histochemical localisation of the complex of compound of formula (I) and TG2 shows that (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate reach the target site and inhibits the target molecule.

Example 3

Study in the Stelic Animal Model (STAM-Model) for Non-Alcoholic Steatohepatitis The anti-fibrotic effect of compound of formula (I) in the liver was investigated in a STAM-model for non-alcoholic steatohepatitis. This model bases on the induction of a chronical fibrotic inflammation of the liver by means of the combination of a chemical noxin (Streptozotocin) and a fat-containing diet in the C57BL/6-mouse. The pathology is similar to the described NASH in human.

Groups of 8 STAM-mice were treated directly over a time period of two weeks with three different dosages of said compound: 100 mg/kg body weight, 300 mg/kg body weight, and 1000 mg/kg body weight. The daily dosage was administered orally as a suspension in two parts at intervals of 8 hours. In a control group, the STAM-mice were treated in same way but merely with the vehicle methyl cellulose. After the end of the treatment, a measurement of the biochemical parameter in the Plasma and after dissection of the animals a histopathological investigation for the liver, the determination of the fat content of the liver as well as the determination of the expression of inflammation and fibrosis marker was performed.

Figure 3:
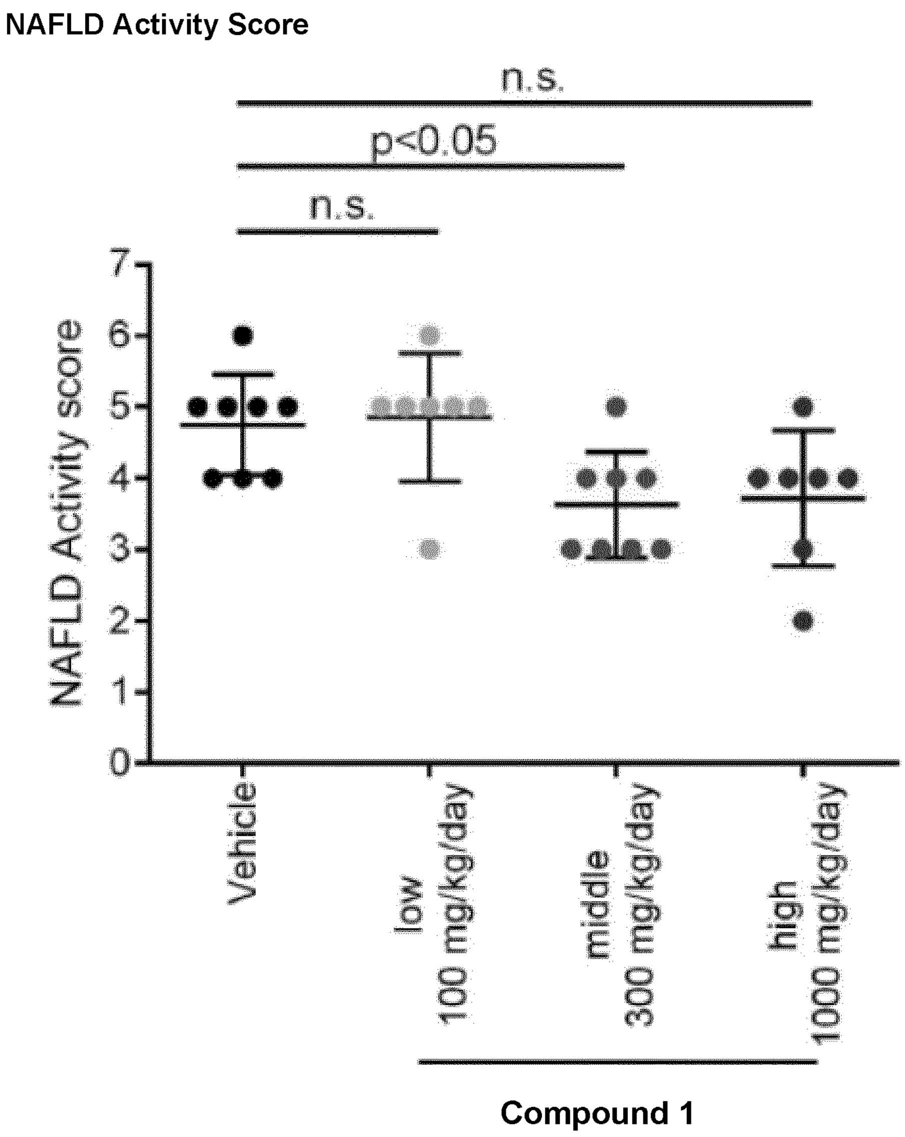
FIG. 3 shows (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (compound 1) in the NASH-model.
Figure 3:
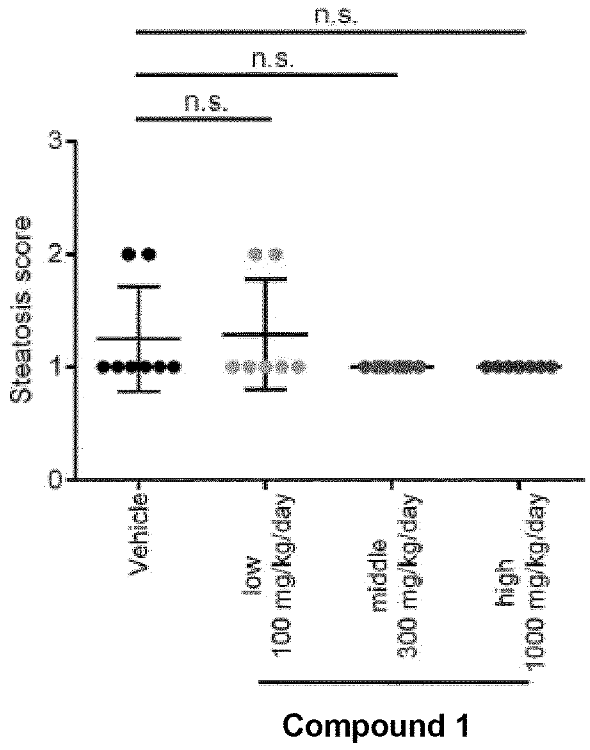
Figure 3:
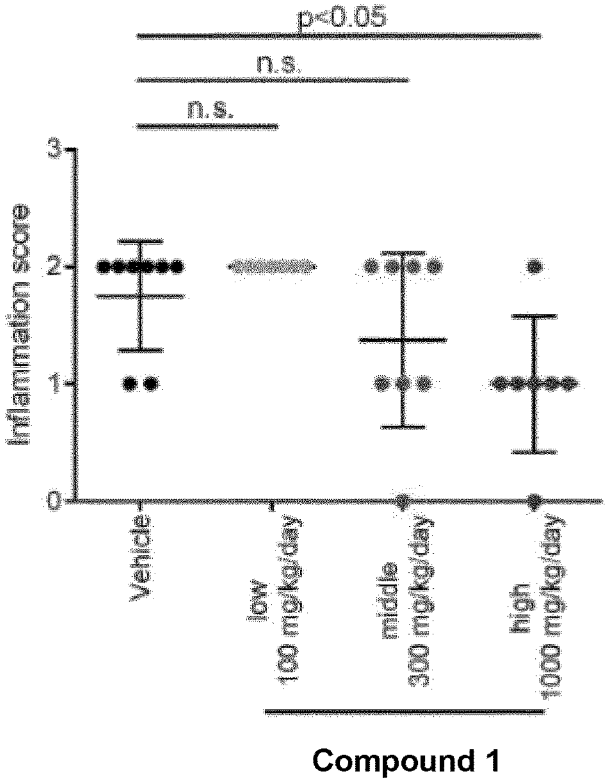
Figure 3:
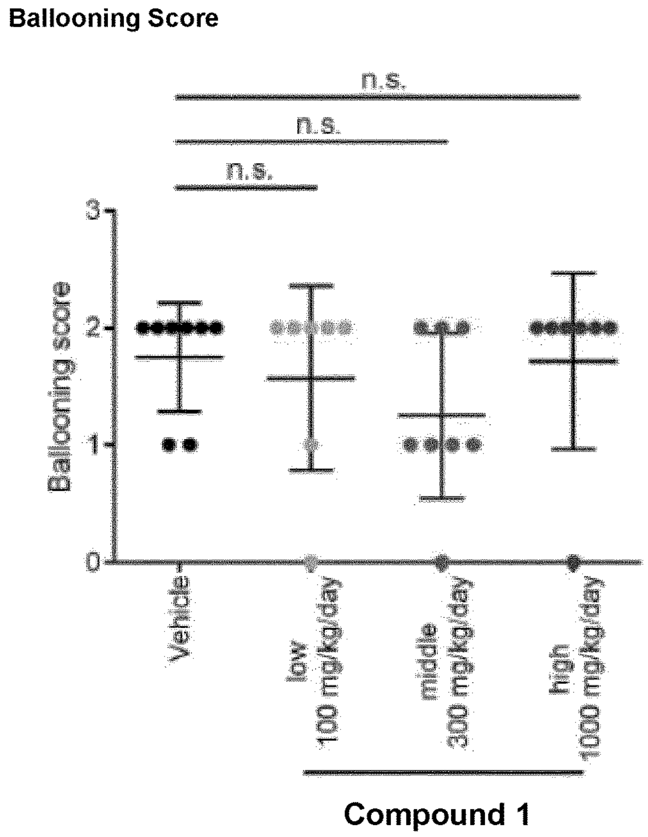
Figure 3:
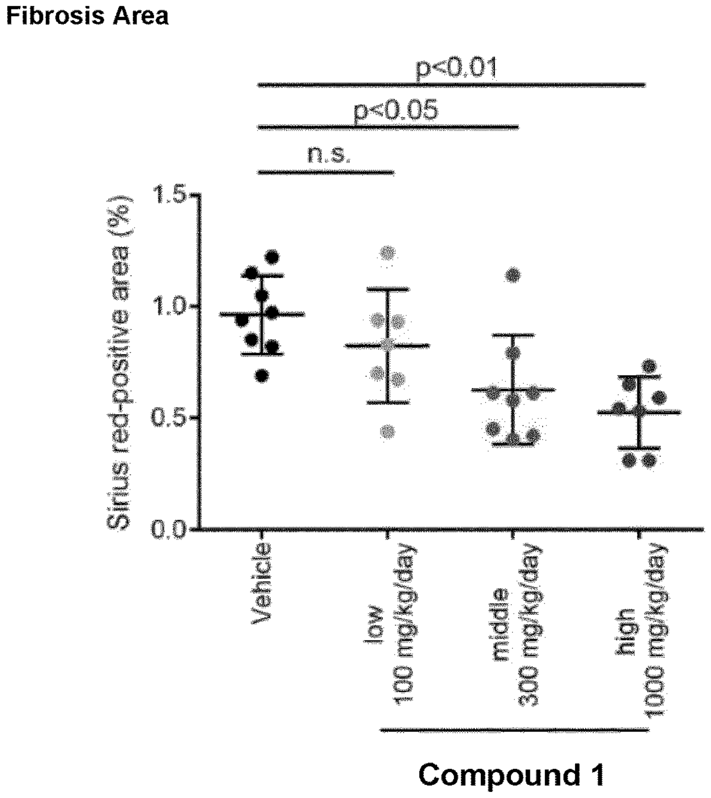

Results: The treatment with compound of formula (I) results in a significant, dosage dependent improvement of the liver histology. In detail, the NAFLD Activity Score (NAS) as shown in FIG. 3 was reduced in the middle and high dosage group. The improvement of the NAS was mainly due to reduction of the inflammation and ballooning (inflate) of the hepatocytes. Furthermore, a marked, dosage dependent reduction of the fibrotic area in the liver could be observed which was significant in the middle and high dosage group. In comparison with historical data, the reduction of the fibrosis in the high dosage group lay in the area of Telmisartan which serves as a positive control.

Conclusion: The anti-fibrotic effect of compound of formula (I) is probably due to the inhibition of TG2 in the liver. As a result, the cross linking of the collagen fibrils is prevented, and the formation of fibrosis in comparison to the untreated control animals is reduced. The reduction of the inflammation and the ballooning are probably secondary to the antifibrotic effect. (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate has no influence on the fat content in the liver.

Example 4

Pharmacokinetic of Compound of Formula (I) in the C57BL/6-Mouse

The study serves to describe the pharmacokinetics of compound of formula (I) in the C57BL/6-mouse. The dosage was analogous to the dosage in the STAM-model (example 3) or in the UUO-model (example 2) in order to ensure the estimation of the systemic exposition in these models and to correlate the pharmacokinetic data with the efficacy data.

Groups of 12 C57BL/6-mice were treated with three different dosages of compound of formula (I) over a time period of 7 days: 100 mg/kg body weight, 300 mg/kg body weight, and 1000 mg/kg body weight. The daily dosage was administered orally as a suspension in two parts at intervals of 8 hours. On day 7 of treatment three different blood samples per animal were collected. The time points in the group were distributed in such a way that the 24 h-profile was covered with in total 12 different time points (3 animals per time point).

The determination of compound of formula (I) in the blood plasma was performed by means of a previously validated HLPC-MS/MS method.

Figure 4:
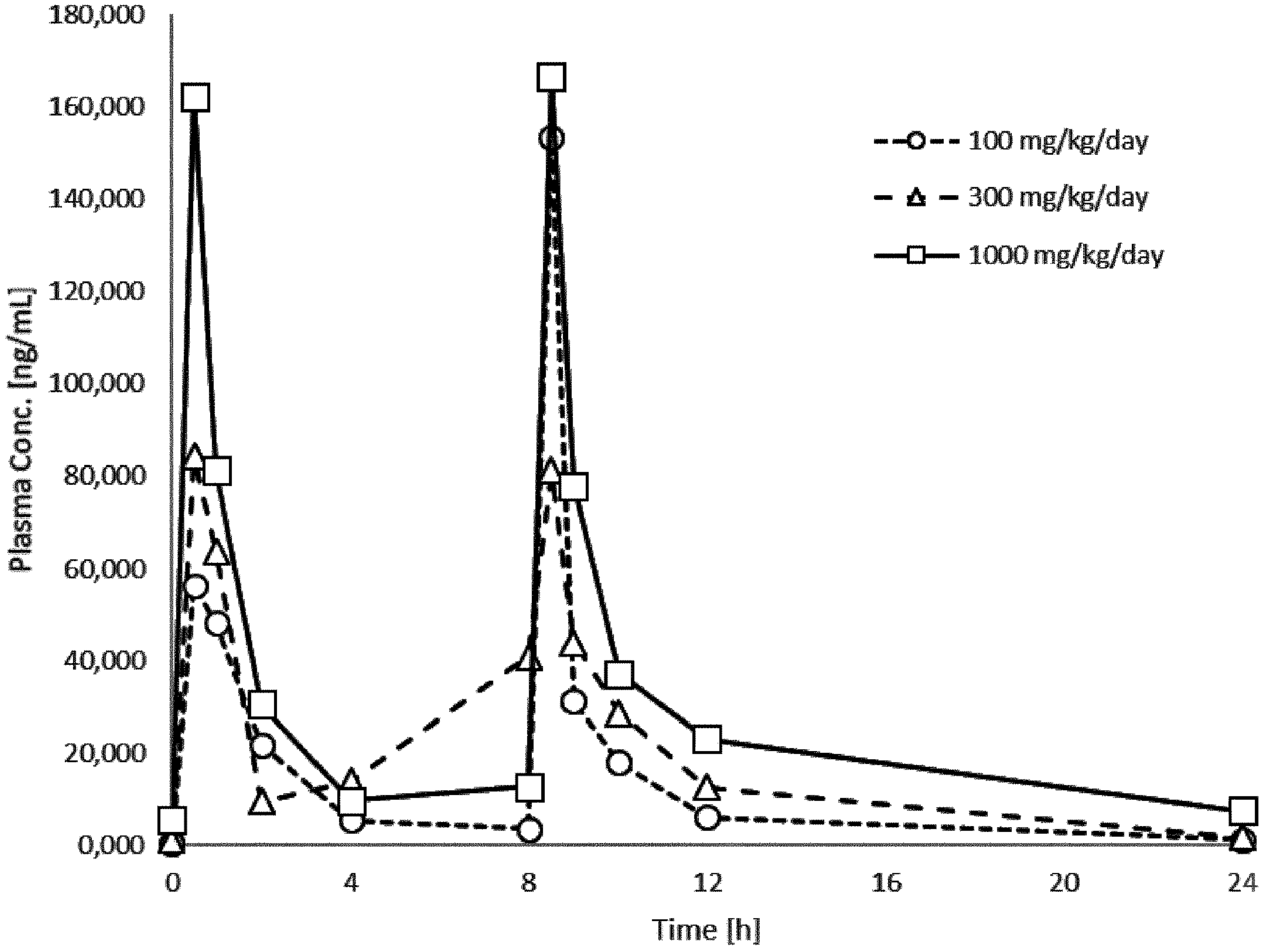
FIG. 4 shows the pharmacokinetic of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate in the C57BL/6-mouse.

Conclusion: The plasma profile of compound of formula (I) as well as the pharmacokinetic data derivable thereof are depicted in FIG. 4.

Example 5

Dose-Activity-Relationship

Figure 5:
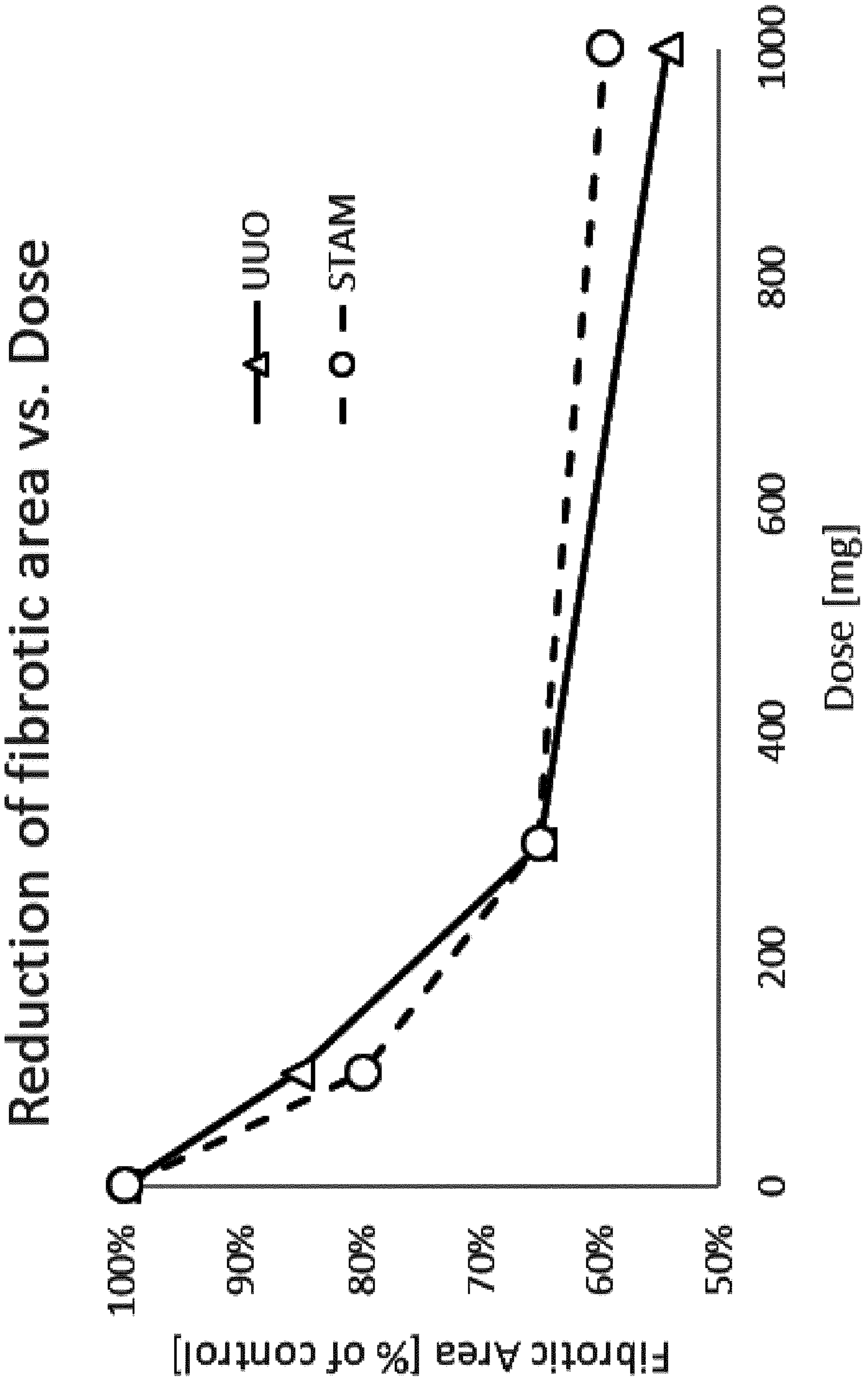
FIG. 5 shows the dose-activity relationship. For the STAM- and UUO-model the anti-fibrotic effect in dependence of the dose or in dependence of the exposition (Plasma Cmax or Plasma-AUC) are depicted.
Figure 5:
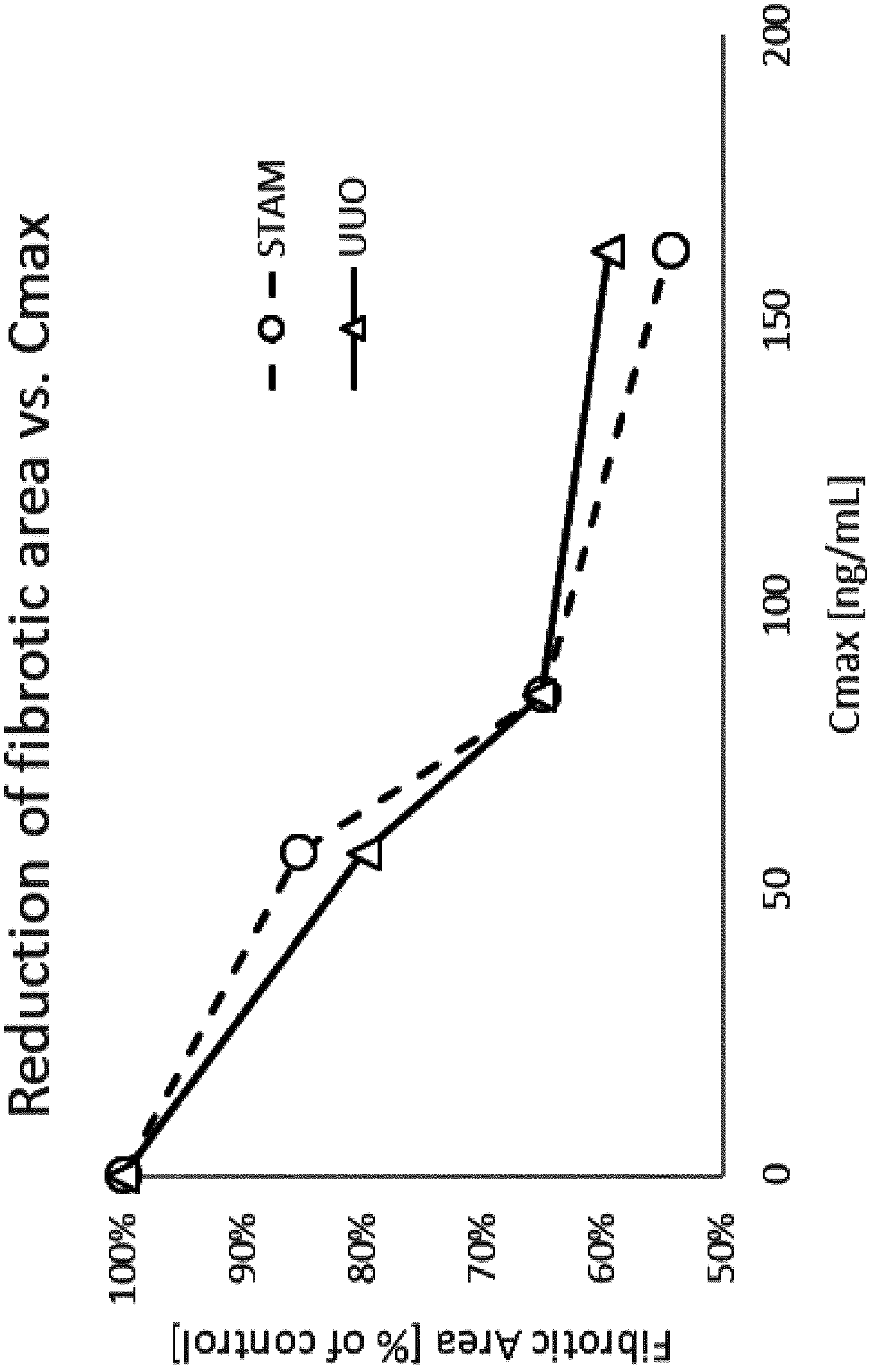
Figure 5:
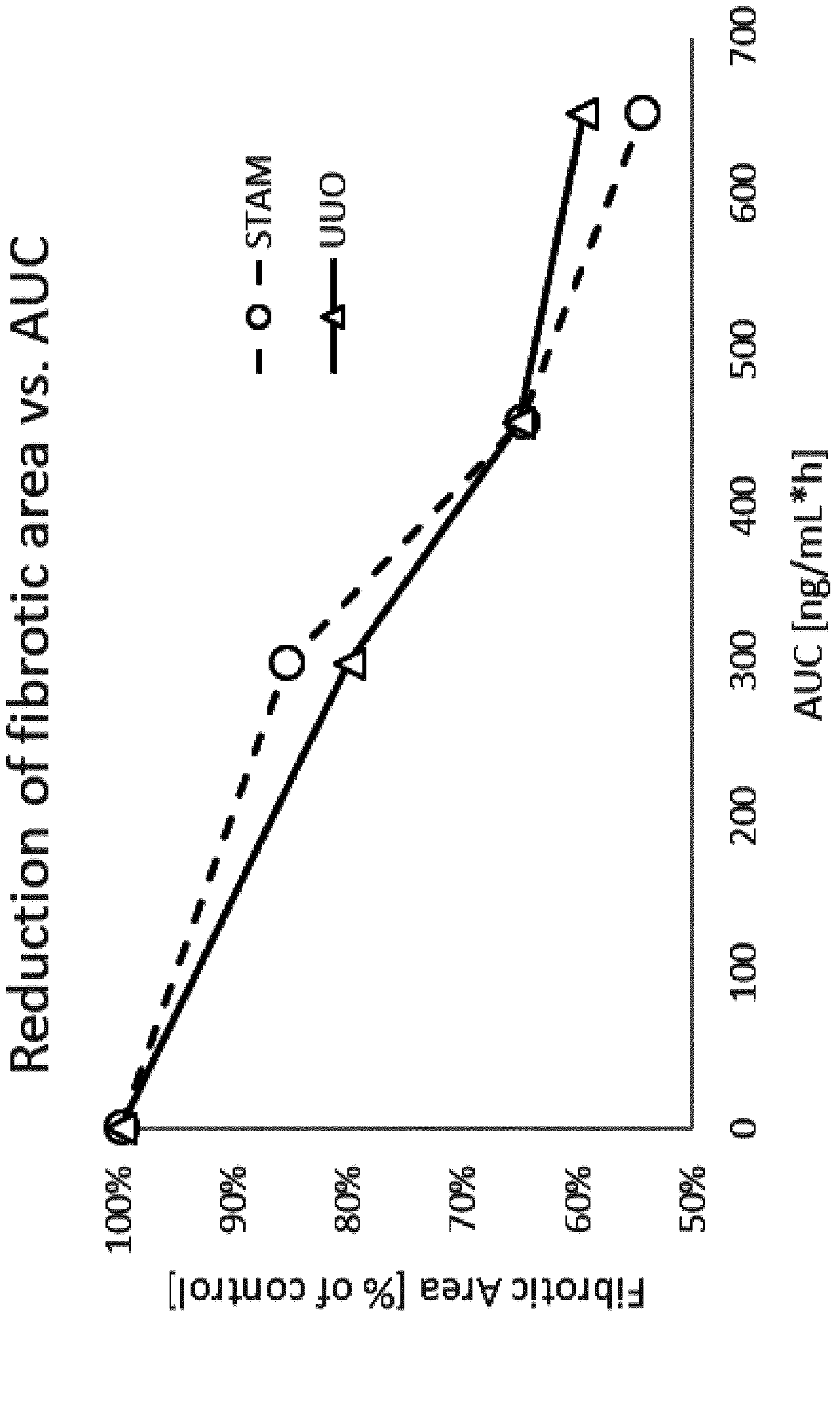

The reduction of the fibrotic area in the tissue in comparison to the untreated control animals can be considered as a measure for the anti-fibrotic effect of compound of formula (I) in STAM-model as well as in the UUO-model. For the STAM- and UUO-model the anti-fibrotic effect in dependence of the dose or in dependence of the exposure (Plasma Cmax or Plasma-AUC) are depicted in FIG. 5.

Results: The results of the investigation of dose-activity-relationship is depicted in FIG. 5.

Conclusion: Although the tissue structure of liver and kidney is different, and the pathogenesis of the fibrotic changes in the STAM-model and in the UUO-model are fundamentally different, compound of formula (I) exhibited in both models the same anti-fibrotic effect. The apparent non-linear dose-activity relationship is probably due to a saturation of the absorption and systemic exposition after the oral administration of the high dosage applied here. If the anti-fibrotic effect in dependence of the exposure in plasma is considered, an almost linear correlation is obtained.

Example 6 Preparation of the Hard Gelatine Capsule

6.1 Preparation A of the Hard Gelatine Capsule

The preparation of the acidic granulate was performed by means of a wet granulation using 96% ethanol as a granulation liquid. Compound of formula (I), L-hydroxypropyl cellulose and sodium croscarmellose are sieved in the dry form, and mixed after that. By adding ethanol, particle agglomeration and formation of the granulate structure results. Granulate mass is sieved in wet form, dried at 70° C., and finally sieved again. In a dry mixer, the sieved adipic acid as well as talc are added to the dry granulate and mixed. After that, the powder mixture is filled in a hard gelatine capsule.

6.2 Preparation B of the Hard Gelatine Capsule

In order to produce a solid formulation for oral administration (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (15.0%) is mixed with polyvinylalcohol (56.9%). The mixture is treated in a hot melt extruder to obtain an extrudate. The extrudate is cooled, and milled. In a dry mixer, crospovidone (7.5%), L-hydroxypropyl cellulose (7.2%), fumaric acid (13.5%) are added to the milled extrudate and mixed. After that, the powder mixture is filled in a hard gelatine capsule.

6.3 Preparation C of the Hard Gelatine Capsule

Hydroxypropyl cellulose (2.3%) are dissolved in isopropanol (96%) to give the granulation liquid. (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (38.8%), cellulose (microcrystalline; 7.8%), polyvinyl caprolactam-polyvinyl acetate-polyethylene glycol graft co-polymer (7.8%), sodium croscarmellose (7.8%) and adipic acid (34.9%) are mixed. The granulation liquid is added to the powder blend whereby a granule mass is formed. The mass is sieved in a wet state, and then dried. After drying the mass is sieved again. Silicon dioxide (0.6%) is added to the dried granules in a dry mixer. Thereafter, the powder mixture is filled in a capsule.

Example 7

Pharmacokinetic of Compound of Formula (I) in Human

The pharmacokinetic of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (compound of formula (I)) was investigated in healthy volunteers. Cohorts of 18 subjects each were treated with a daily dose of 10, 20, 50 and 100 mg compound of formula (I), respectively over a time period of 7 days. The determination of said compound in blood plasma was performed by means of a previously validated HPLC-MS/MS method.

Figure 6:
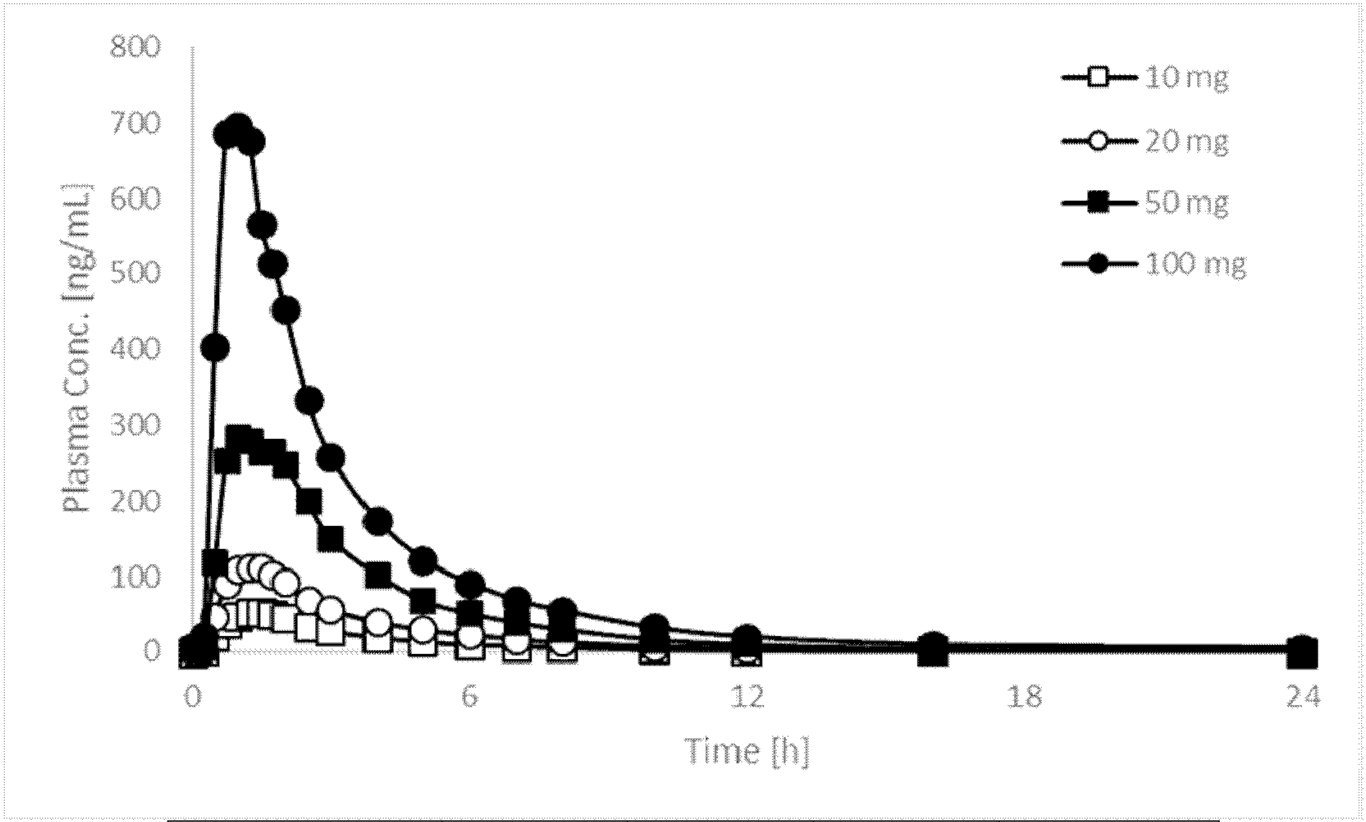
FIG. 6 shows the plasma profiles of the compound as well as the human pharmacokinetic data derivable thereof after the multiple dosing according to example 7.

Results: The plasma profiles of the compound as well as the human pharmacokinetic data derivable thereof after the multiple dosing are depicted in FIG. 6.

Conclusion: The drug concentration achieved with the formulation increases in the dose range 10-100 mg dose-proportionally, and when normalized to the body weight lies remarkably higher than in the animal studies in which the drug was administered as a suspension.

Figure 7:
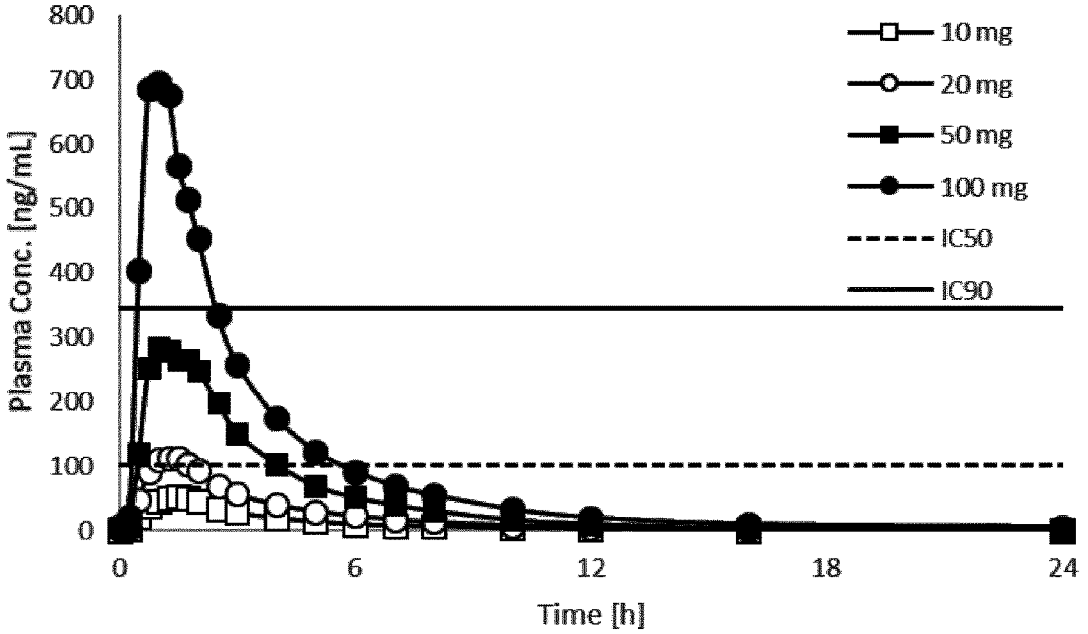
FIG. 7 shows the correlation of the humane pharmacokinetic data with the in vitro data for the TG2 inhibition.

The drug concentration achieved are compared with the concentrations which in vitro result in an inhibition of the enzyme activity of TG2 (FIG. 7). Thereby, the TG2-catalysed incorporation of dansyl-cadaverine into N,Ndimethylcasein (DCC-Assay), representing the cross-linking function of TG2, serves as a marker reaction. According to this correlation, the half maximal inhibition ($IC_{50}$) of TG2 is already achieved with a dose of 20 mg. A dose of 50 mg of the new developed formulation results in a drug level already exceeding the $IC_{90}$ of the enzyme inhibition. The 90% inhibition at $IC_{90}$ can be regarded as maximal pharmacodynamic effect.

Example 8 Comparison of Pharmacokinetic Data of the Formulation with Pharmacokinetic Data of the Plain Compound The human pharmacokinetic data of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (compound of formula (I)) described in example 7 were generated after administration of the hard gelatine capsule formulation described in example 6.

To estimate the influence of the formulation, the pharmacokinetic data of the hard gelatine formulation were compared with pharmacokinetic data generated after oral administration of the plain, unformulated compound. Due to regulatory and ethical reasons pharmacokinetic data with the plain compound were only generated in animals but not in human subjects.

The pharmacokinetic data of the plain compound were derived from several studies in monkeys, pigs, rabbits, rats and mice. In all studies the compound was administered orally after suspension in 0.5% (w/v) methylcellulose in water, pH 5±0.5. Blood samples were taken at various time points within 24 h after drug administration and quantified by means of a previously validated HPLC-MS/MS method.

Figure 8:
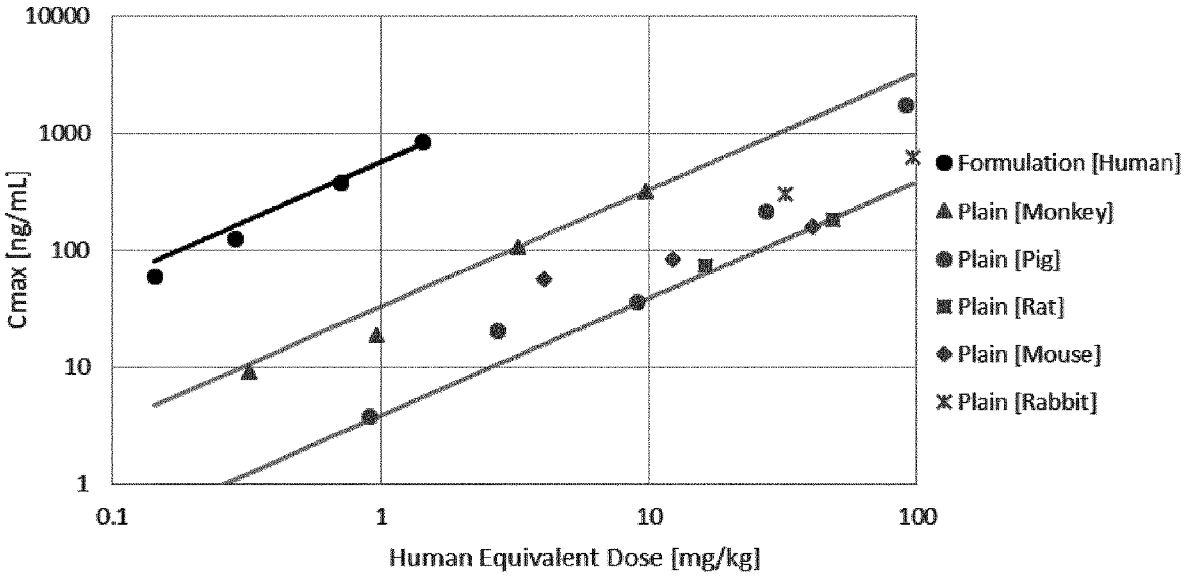
FIG. 8 shows the maximal plasma concentration (Cmax) reached after administration of different doses of compound of formula I in formulation or as a plain compound. In order to compile the data from different species, doses were converted into human-equivalent-dose (HED) taking into account differences in the body surface area between species. The widely accepted species-specific conversion factors defined in the FDA guideline "Estimating the Maximum Safe Starting Dose in Initial Clinical Trials for Therapeutics in Adult Healthy Volunteers" (Issue date 2005) were used.

FIG. 8 shows the maximal plasma concentration (Cmax) reached after administration of different doses of compound of formula I in formulation or as a plain compound. In order to compile the data from different species, doses were converted into human-equivalent-dose (HED) taking into account differences in the body surface area between species. The widely accepted species-specific conversion factors defined in the FDA guideline "Estimating the Maximum Safe Starting Dose in Initial Clinical Trials for Therapeutics in Adult Healthy Volunteers" (Issue date 2005) were used.

The comparison in FIG. 7 demonstrates over a wide dose range that the Cmax reached after administration of the formulation is more than 10-fold above the Cmax reached after administration of the plain compound. Although the differences in Cmax could partly be attributed to species differences in pharmacokinetics, the large difference between data from human and the closely related monkey suggest that the formulation plays a major role in achieving a high systemic exposure.

Example 9

Correlation of the Anti-Fibrotic Effect with the Human Pharmacokinetic

The anti-fibrotic effect of (5,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate in the animal model suggests a potential use of said compound in case of fibrotic liver or kidney diseases in human. A comparison of the systemic exposure (Cmax, AUC) of (5,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate in dosage effective in the animal experiments with the systemic exposition which is achieved in human allows an estimation of the potential effective dose range.

Figure 9:
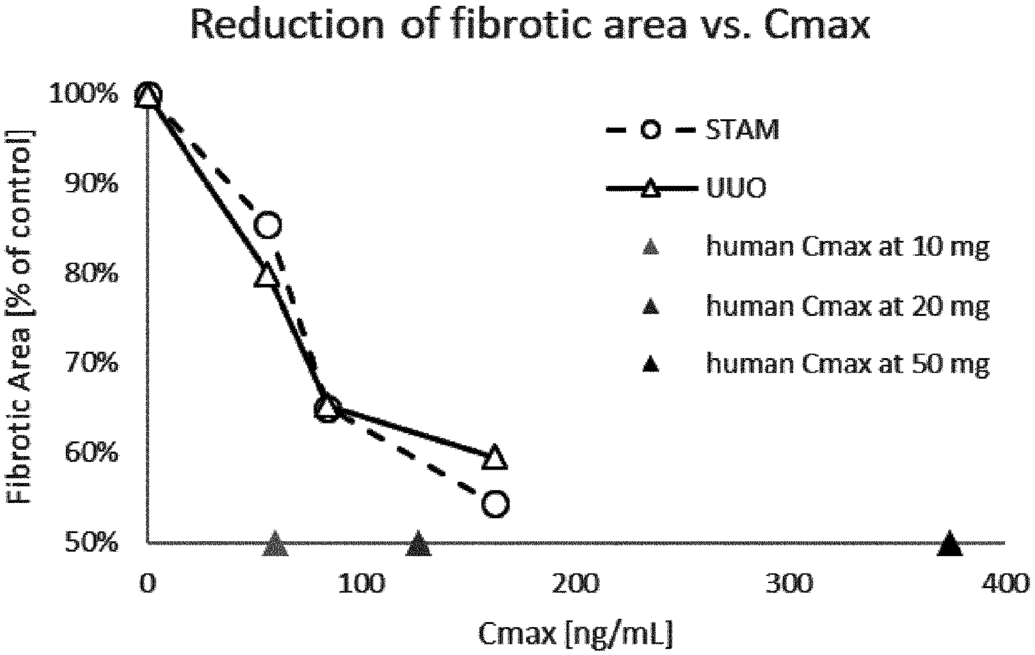
FIG. 9 shows anti-fibrotic effects in the animal model in dependence of the Cmax value as well as AUC value. In addition, the Cmax value being achieved in human by the dosage of 10, 20, and 50 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate is shown.
Figure 10:
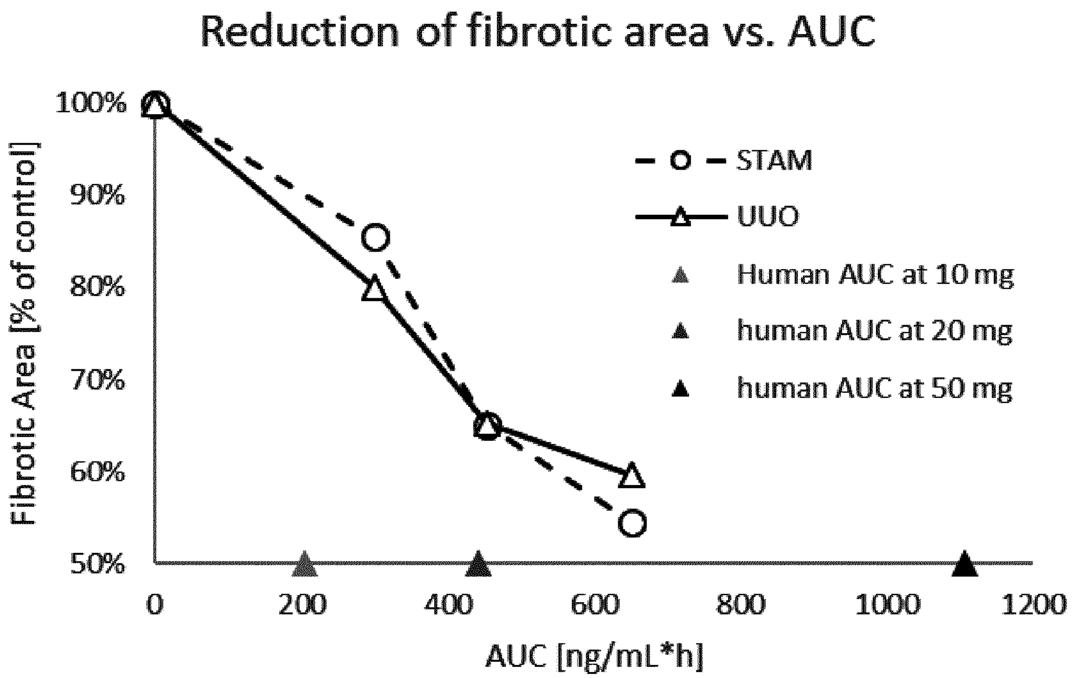
FIG. 10 shows the anti-fibrotic effects in the animal model in dependence of the AUC value. In addition, the AUC value being achieved in human by the dosage of 10, 20, and 50 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate is shown.

The anti-fibrotic effects in the animal model in dependence of the Cmax value as well as AUC value are shown in FIG. 9 and FIG. 10. In addition, the Cmax or AUC being achieved in human by the dosage of 10, 20, and 50 mg compound of formula (I) is shown.

Conclusion: The relationship between the fibrotic area and Cmax value (FIG. 9) or AUC value (FIG. 10), respectively suggests that the anti-fibrotic effect shown in the animal model can already be achieved with a human dosage of 20 mg. In human, the systemic exposure further increases linearly up to 100 mg. The almost linear dependence of the anti-fibrotic effect from the systemic exposition suggests that at higher dosage a stronger anti-fibrotic effect could be achieved in human than in the animal model.

Example 10

The saturation solubility of compound of formula (I) was measured in the pH-range from 1 to 6.8 using HPLC/UV.

Figure 11:
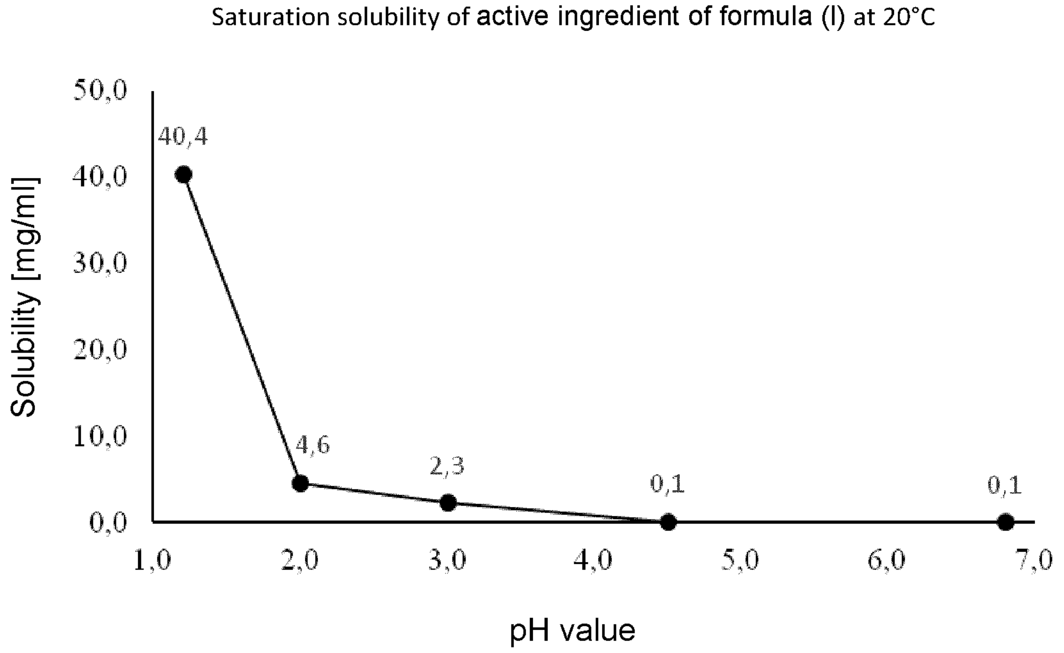
FIG. 11 shows the saturation solubility of (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate.

The results are illustrated in FIG. 11.

Results: It is apparent that the saturation solubility is much lower at a pH=6.8 (small intestine) than at a pH~1.

It is remarkably that the bioavailability in the mouse model is measurable, although the saturation solubility is much lower at a pH=6.8 than at a pH~1.

Example 11: Preparation of a Pharmaceutical Composition in Form of a Tablet

11.1 Preparation A of a Pharmaceutical Composition in Form of a Tablet

In order to produce a solid formulation for oral administration (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (7.6%) is mixed with L-hydroxypropyl methylcellulose (18.3%), croscarmellose sodium (1.5%), povidone K25 (8.4%) and cellulose (microcrystalline; 36.6%). The powder blend is granulated with ethanol (96%). After wet sieving the granules are dried. Adipic acid (13.7%), croscarmellose sodium (12.2%) and silicon dioxide (1.5%) are added to the granules to obtain the final blend which is compressed to tablets.

The tablet can then be coated with a film consisting of: lactose monohydrate, hydroxypropyl methylcelluose (E464; also known as hypromellose), titanium dioxide (E171), triacetin (E1518), iron oxide yellow (E172), and carnauba wax (E903).

11.2 Preparation B of a Pharmaceutical Composition in Form of a Tablet

In order to produce a solid formulation for oral administration (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (22.0%) is mixed with L-hydroxypropyl methylcellulose (10.6%), croscarmellose sodium (11.0%), and mannitol (11.0%). The powder blend is granulated a solution of hydroxypropyl cellulose (1.3%) in ethanol (96%). After wet sieving the granules are dried. Glutaric acid (39.7%), and talcum (4.4%) are added to the granules to obtain the final blend which is compressed to tablets.

11.3 Preparation C of a Pharmaceutical Composition in Form of a Tablet

In order to produce a solid formulation for oral administration (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (15.4%) is mixed with polyvinylalcohol (58.6%). The mixture is treated in a hot melt extruder to obtain an extrudate. The product is cooled, milled, and mixed with croscarmellose sodium (6.2%), cellulose (microcrystalline; 6.2%), glutaric acid (12.4%), silicon dioxide (0.6%), and talc (0.6%) to obtain the final blend which is compressed to tablets.

The tablet can then be coated with a film consisting of: lactose monohydrate, hydroxypropyl methylcellulose (E464; also known as hypromellose), titanium dioxide (E171), triacetin (E1518), iron oxide yellow (E172), and carnauba wax (E903).

Example 12: Preparation of Granules for Capsules

12.1 Preparation A of Granules for Capsules 50 mg L-hydroxypropyl cellulose, and 25 mg sodium croscarmellose are added to 10 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate. The compounds are sieved in a dry state. 50 mg ethanol are added, whereby an granule mass is formed. The mass is sieved in a wet state, and then dried. After drying, the mass is sieved again. 115 mg adipic acid, and 12 mg talc is added to the dried granules in a in a dry mixer. Thereafter, the powder mixture is filled in a capsule.

12.2 Preparation B of Granules for Capsules 24 mg L-hydroxypropyl cellulose are dissolved in 22 ml ethanol to give the granulation liquid. 10 mg (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate, 3 mg L-hydroxypropyl cellulose (low substituted), 25 mg sodium croscarmellose and 25 mg manitol are mixed. The granulation liquid is added to the powder blend whereby a granule mass is formed. The mass is sieved in a wet state, and then dried. After drying the mass is sieved again. 18 mg adipic acid and 5 mg talc are added to the dried granules in a dry mixer. Thereafter, the powder mixture is filled in a capsule.

12.3 Preparation C of Granules for Capsules

Hydroxypropyl cellulose (1.3%) are dissolved in ethanol (96%) to give the granulation liquid. (S,E)-methyl-7-(1-(2-(2-ethylbutylamino)-2-oxoethyl)-2-oxo-1,2-dihydro-pyridin-3-ylamino)-6-(1-methyl-1H-imidazole-5-carboxamido)-7-oxohept-2-enoate (22.0%), L-hydroxypropyl cellulose (low substituted; 10.6%), sodium croscarmellose (11.0%) and manitol (11.0%) are mixed. The granulation liquid is added to the powder blend whereby a granule mass is formed. The mass is sieved in a wet state, and then dried. After drying the mass is sieved again. adipic acid (39.7%) and talc (4.4%) are added to the dried granules in a dry mixer. Thereafter, the powder mixture is filled in a capsule.

Example 13: Micronization Process

The (S,E)-methyl-7-(1-(2-(2-ethylbutylamino)-2-oxoethyl)-2-oxo-1,2-dihydro-pyridin-3-ylamino)-6-(1-methyl- 1H-imidazole-5-carboxamido)-7-oxohept-2-enoate is micronized, wherein the particle size distribution is preferably defined by d(0.1) from 0.1 to 5 μm, d(0.5) from 0.3 to 10 μm, d(0.95) from 3 to 25 μm, and the particle size range is from 0.1 to 100 μm.

Figure 12:
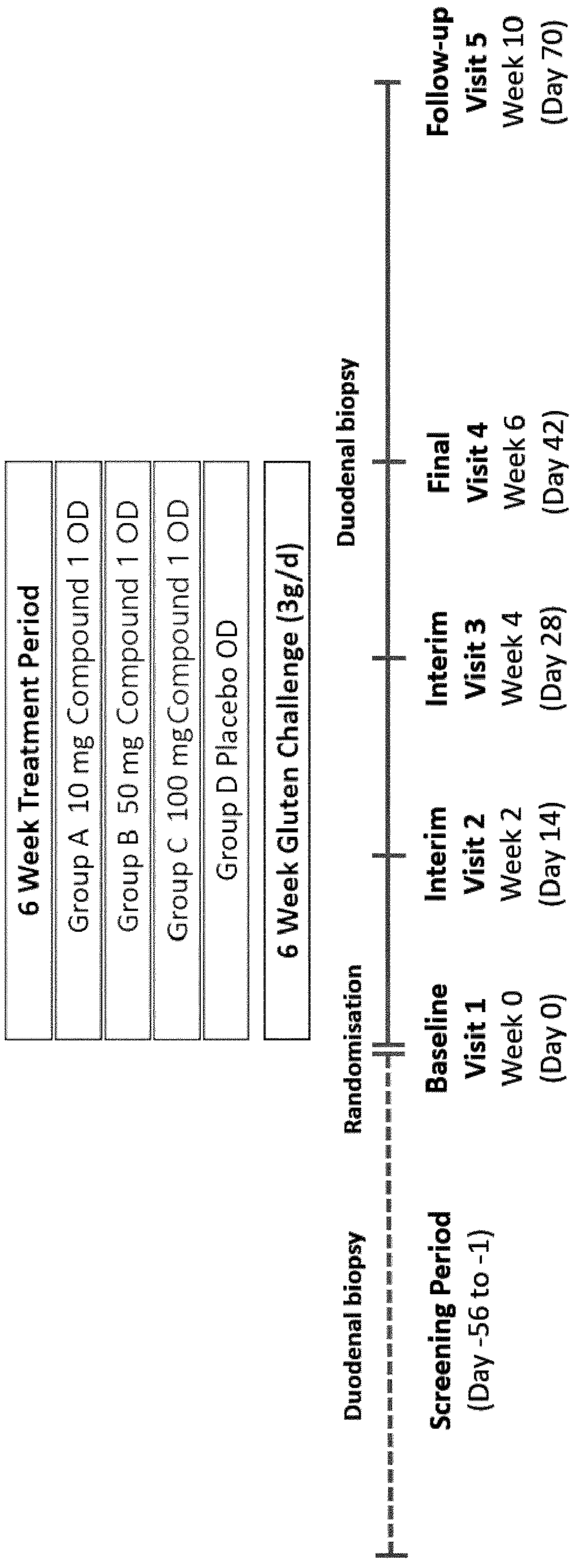
FIG. 12 shows a trial design schematic of Example 14.

Example 14: In Vivo Efficacy and Safety Data and Hepatoprotective Effect of a Pharmaceuteutical Composition in Form of a Capsule Formulation The efficacy and safety of a 6-week treatment with the compound of formula (I) in the hard gelatine capsule formulation described in the example 2 was investigated in 160 adult patients with Celiac Disease (CeD). Patients, who were in clinical and histological remission at start of the study were challenged with 3 grams daily gluten intake and randomized to receive placebo or one of 3 doses of the compound of formula (I), i.e. 10 mg, 50 mg or 100 mg. Each morning after at least 6 hours of fasting, patients took the study drug orally, followed by one biscuit containing 3 g of gluten 30 minutes later, before breakfast. Throughout the 6-week study, patients were required to continue their strict gluten free diet (see FIG. 12).

Gluten challenge caused a mild but statistically significant elevation of alanine aminotransferase (ALT) from baseline to week 6 in the placebo group, but this elevation was surprisingly not observed in any of the groups the compound of formula (I) in the hard gelatine capsule formulation described in example 2. The difference between each drug group and placebo in ALT was statistically significant (P<0.01 for all comparisons), suggesting a protective effect by the compound of the formula (I) on the liver of celiac disease patients exposed to gluten. Alkaline phosphatase (ALP) levels showed also a similar pattern (P<0.05). In the placebo group, the values normalized upon GFD at week 10 (Table 1). The finding that the compound of formula (I) inhibits liver injury, which is one of the gluten-driven extraintestinal manifestations in active Celiac Disease (CeD), as reflected in a mild elevation of ALT and ALP (reference 3), demonstrates that the compound exerts a general hepatoprotective effect.

TABLE 1

Mean (standard deviation) alanine aminotransferase (ALT), aspartate aminotransferase (AST), and alkaline phosphatase (ALP) levels from baseline to week 6 (safety population, units: U/L)

| | 10 mg (N = 41) | 50 mg (N = 41) | 100 mg (N = 40) | Placebo (N = 38) |
|---|---|---|---|---|
| ALT | | | | |
| Baseline | 20.5 (7.5) | 21.4 (8.3) | 26.3 (16.9) | 23.8 (10.2) |
| Week 6 | 20.0 (6.1) | 22.2 (9.1) | 23.7 (9.3) | 28.6 (11.8) |
| Change from baseline | −0.5 (8.1) | 0.8 (7.2) | −2.6 (13.4) | 4.3 (10.8) |
| Difference versus placebo | −4.4 | −3.8 | −4.3 | — |
| P value | 0.0019 | 0.0069 | 0.0022 | — |
| Week 10 (Follow-up) | 19.7 (5.9) | 21.7 (10.2) | 23.9 (10.1) | 23.9 (10.3) |
| AST | | | | |
| Baseline | 22.5 (8.7) | 22.6 (6.8) | 26.8 (11.8) | 23.9 (7.2) |
| Week 6 | 22.5 (5.5) | 23.6 (7.0) | 26.5 (9.6) | 26.3 (6.6) |
| Change from baseline | 0 (6.7) | 1.0 (5.6) | −0.4 (14.4) | 2.1 (6.4) |
| Difference versus placebo | −3.2 | −2.2 | 0.3 | — |
| P value | 0.0448 | 0.1423 | 0.8551 | — |
| Week 10 (Follow-up) | 20.6 (5.1) | 21.9 (5.7) | 24.3 (6.5) | 24.1 (8.3) |
| ALP | | | | |
| Baseline | 60.0 (18.3) | 57.8 (15.0) | 62.7 (18.7) | 63.6 (19.0) |
| Week 6 | 59.3 (18.5) | 57.3 (15.3) | 62.3 (22.1) | 67.0 (22.9) |
| Change from baseline | −1.0 (5.4) | −0.5 (5.7) | −0.5 (8.4) | 3.3 (7.8) |
| Difference versus placebo | −2.6 | −2.8 | −2.8 | — |

Normal ranges for adult females/males: ALT, AST (10-35/10-50 U/L), ALP (35-104/40-129 U/L)

REFERENCES OF EXAMPLE 14

1. Korpimäki S, Kaukinen K, Collin P, et al. Gluten-sensitive hypertransaminasemia in celiac disease: an infrequent and often subclinical finding. The American journal of gastroenterology 2011; 106:1689-96.
2. Kahaly G J, Frommer L, Schuppan D. Celiac disease and endocrine autoimmunity—the genetic link. Autoimmun Rev 2018; 17:1169-75.
3. Lebwohl B, Sanders D S, Green P H R. Coeliac disease. Lancet 2018; 391:70-81.
4. Ludvigsson J F, Leffler D A, Bai J C, et al. The Oslo definitions for coeliac disease and related terms. Gut 2013; 62:43-52.
5. Schuppan D, Junker Y, Barisani D. Celiac disease: from pathogenesis to novel therapies. Gastroenterology 2009; 137:1912-33.

The invention claimed is:

1. A systemic formulation containing Compound 1 of the formula (I):

(I)

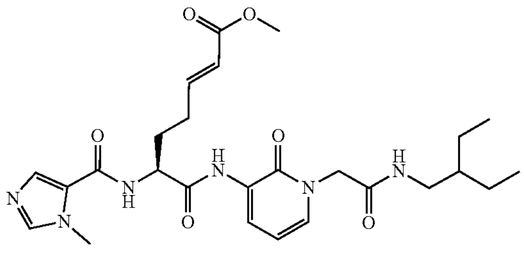

or an enantiomer, a solvate, a hydrate or a pharmaceutically acceptable salt thereof, and at least one polymeric precipitation inhibitor, wherein the mass ratio of the at least one polymeric precipitation inhibitor relative to Compound 1 ranges from 0.05 to 10 m/m.

2. The systemic formulation according to claim 1, wherein the systemic formulation is an oral formulation.

3. The systemic formulation according to claim 1, wherein the systemic formulation further comprises at least one acidifier, at least one binder, or a combination of at least one acidifier and at least one binder.

4. The systemic formulation according to claim 1, wherein the at least one polymeric precipitation inhibitor is selected from the group consisting of L-hydroxypropyl cellulose, hydroxypropyl cellulose, a combination of L-hydroxypropyl cellulose and hydroxypropyl cellulose, polyethylene glycol, poly (ethylene oxide)-poly (propylene oxide)-poly (ethylene oxide), polyvinyl alcohol, polyvinylpyrrolidone, carboxymethyl cellulose, methylcellulose, hydroxyethylcellulose, hydroxypropylmethylcellulose, ethylcellulose, polyvinyl caprolactam-polyvinyl acetate-polyethylene glycol graft copolymer, and sodium carboxymethyl cellulose.

5. The systemic formulation according to claim 3, wherein the at least one acidifier is selected from the group consisting of ascorbic acid, organic di-carboxylic acid, and organic tri-carboxylic acid.

6. The systemic formulation according to claim 3, wherein the at least one binder is selected from the group consisting of sugar, sucrose, polysaccharides, xanthan gum, guar gum, carrageenan, starches derived from wheat, corn, rice or potatoes, preagglutinated (modified) starch derived from wheat, corn, rice or potatoes, sodium starch glycolate, natural gums, acacia gum, gelatin, tragacanth, derivatives of sea weed, alginic acid, sodium alginate, ammonium calcium alginate, cellulose, cellulose derivatives, and polyvinylpyrrolidone.

7. The systemic formulation according to claim 1, wherein Compound 1 is in the form of particles having a particle size distribution which is defined by $d(0.95) \leq 25$ μm.

8. The systemic formulation according to claim 1, wherein the systemic formulation is a tablet, coated tablet, capsule, powder, or granule.

9. The systemic formulation according to claim 3, wherein the systemic formulation comprises 1 to 15 m/m acidifier, 0.1 to 7 m/m polymeric precipitation inhibitor, wherein m/m (mass ratio) of said acidifier and polymeric precipitation inhibitor is calculated relative to mass of Compound 1.

10. The systemic formulation according to claim 1, wherein the formulation comprises 0.1 wt % to 45 wt % Compound 1, 3 wt % to 75 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

11. The systemic formulation according to claim 1, wherein the systemic formulation comprises 0.1 wt % to 45 wt % Compound 1, 3 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

12. A method for the treatment of a liver disorder or disease comprising administering to a subject an effective amount of Compound 1 of formula (I):

(I)

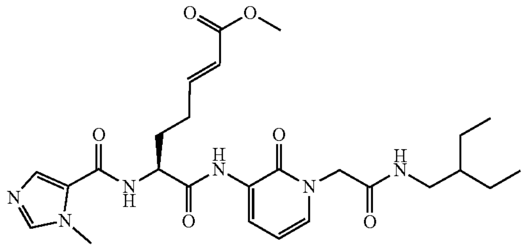
, an enantiomer, a solvate, a hydrate or a pharmaceutically acceptable salt thereof, or a pharmaceutical composition comprising Compound 1, wherein the liver disorder or disease is fibrotic liver diseases, cholestatic liver diseases, autoimmune hepatitis, or alcoholic steatohepatitis.

13. The method according to claim 12, wherein the liver disorder or disease is non-alcoholic fatty liver disease, nonalcoholic steatohepatitis, cirrhosis, primary sclerosing cholangitis, or primary biliary cholangitis.

14. The method according to claim 12, wherein the liver disorder or disease is diabetes related fibrosis.

15. A method for the protection of the liver against hepatotoxicity comprising administering to a subject an effective amount of Compound 1 of formula (I):

(I)

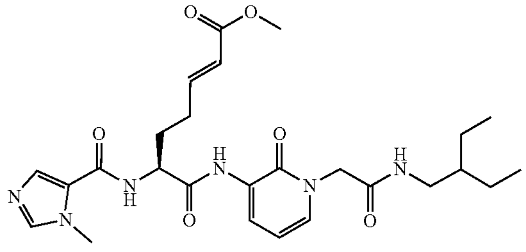
, or an enantiomer, a solvate, a hydrate or a pharmaceutically acceptable salt thereof, as a hepatoprotectant, wherein the protection of the liver against hepatotoxicity comprises the improvement of liver function, the protection against a liver injury, or the repair of a liver injury.

16. The method according to claim 15, wherein the hepatotoxicity or the liver injury is caused by at least one hepatotoxicant, celiac disease, or a viral infection.

17. The method according to claim 16, wherein the at least one hepatotoxicant is selected from the group consisting of a toxic chemical, a xenobiotic, an anticancer drug, an immunosuppressant drug, an analgesic drug, an anti-inflammatory drug, an anti-tubercular drug, a biological, radiation, a heavy metal, mycotoxin, galactosamine, a lipopolysaccharide, a celiac disease associated with a specific genetic phenotype, a pathobiology promoted by transglutaminase 2, and a viral infection with hepatitis A, B, or C virus.

18. The method according to claim 15, wherein the compound is administered orally.

19. A method for the protection of the liver against hepatotoxicity comprising administering to a subject an effective amount of a pharmaceutical composition comprising Compound 1 of the formula (I):

(I)

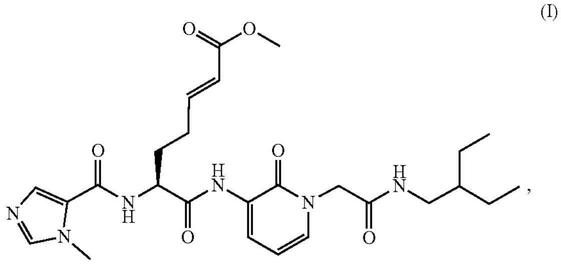 [SMILES: CCC(CC)CNC(=O)Cn1cccc(NC(=O)[C@H](CC/C=C/C(=O)OC)NC(=O)c2cncn2C)c1=O]

or an enantiomer, a solvate, a hydrate or a pharmaceutically acceptable salt thereof, and at least one pharmaceutically acceptable excipient, as a hepatoprotectant, wherein the protection of the liver against hepatotoxicity comprises the improvement of liver function, the protection against a liver injury, the repair of a liver injury, or treatment of a liver disorder or disease.

20. The method according to claim 19, wherein the compound reduces serum levels of at least one hepatic enzyme.

21. The method according to claim 20, wherein the at least one hepatic enzyme is selected from the group consisting of alanine aminotransferase (ALT), aspartate aminotransferase (AST), and alkaline phosphatase (ALP).

22. The method according to claim 19, wherein the liver disorder or disease is liver fibrosis, alcoholic hepatitis, nonalcoholic steatohepatitis, non-alcoholic fatty liver disease, cirrhosis, primary sclerosing cholangitis, primary biliary cholangitis, autoimmune hepatitis, alcoholic steatohepatitis, or liver inflammation.

23. The method according to claim 19, wherein the hepatotoxicity, liver injury, the liver disease or the liver disorder is caused by at least one hepatotoxicant, celiac disease, or a viral infection.

24. The method according to claim 23, wherein the at least one hepatotoxicant is selected from the group consisting of a toxic chemical, a xenobiotic, an anticancer drug, an immunosuppressant drug, an analgesic drug, an anti-inflammatory drug, an anti-tubercular drug, a biological, a radiation, a heavy metal, mycotoxin, galactosamine, a lipopolysaccharide, a celiac disease associated with a specific genetic phenotype, a pathobiology promoted by transglutaminase 2 and a viral infection with hepatitis A, B, or C virus.

25. The method according to claim 19, wherein the pharmaceutical composition further comprises at least one polymeric precipitation inhibitor.

26. The method according to claim 19, wherein the pharmaceutical composition further comprises at least one acidifier and/or at least one binder.

27. The method according to claim 25, wherein the at least one polymeric precipitation inhibitor is selected from the group consisting of L-hydroxypropyl cellulose, hydroxypropyl cellulose, a combination of L-hydroxypropyl cellulose and hydroxypropyl cellulose, polyethylene glycol, poly (ethylene oxide)-poly (propylene oxide)-poly (ethylene oxide), polyvinyl alcohol, polyvinylpyrrolidone, carboxymethyl cellulose, methylcellulose, hydroxyethylcellulose, hydroxypropylmethylcellulose, ethylcellulose, polyvinyl caprolactam-polyvinyl acetate-polyethylene glycol graft co-polymer, and sodium carboxymethyl cellulose.

28. The method according to claim 26, wherein the at least one acidifier is selected from the group consisting of ascorbic acid, organic di-carboxylic acid, and organic tri-carboxylic acid.

29. The method according to claim 26, wherein the at least one binder is selected from the group consisting of sugar, sucrose, polysaccharides, xanthan gum, guar gum, carrageenan, starches derived from wheat, corn, rice or potatoes, preagglutinated (modified) starch derived from wheat, corn, rice or potatoes, sodium starch glycolate, natural gums, acacia gum, gelatin, tragacanth, derivatives of sea weed, alginic acid, sodium alginate, ammonium calcium alginate, cellulose, cellulose derivatives, and polyvinylpyrrolidone.

30. The method according to claim 19, wherein Compound 1 is in the form of particles having a particle size distribution which is defined by d (0.95)≤25 μm.

31. The method according to claim 19, wherein the pharmaceutical composition is an oral formulation.

32. The method according to claim 31, wherein the oral formulation is a tablet, coated tablet, capsule, powder, or granule.

33. The method according to claim 25, wherein the pharmaceutical composition comprises 1 to 15 m/m acidifier, 0.1 to 7 m/m polymeric precipitation inhibitor, wherein m/m (mass ratio) of said acidifier and polymeric precipitation inhibitor compounds is calculated relative to mass of Compound 1.

34. The method according to claim 25, wherein the pharmaceutical composition comprises 0.1 wt % to 45 wt % Compound 1, 3 wt % to 75 wt % acidifier, 2 wt % to 35 wt % polymeric precipitation inhibitor, 0 wt % to 12 wt % binder, 2 wt % to 35 wt % disintegrant, and 1 wt % to 9 wt % lubricant/glidant.

35. The method according to claim 25, wherein the pharmaceutical composition comprises 0.1 wt % to 45 wt % Compound 1, 3 wt % to 75 wt % adipic acid, 2 wt % to 35 wt % L-hydroxypropyl cellulose and/or hydroxypropyl cellulose, 0 wt % to 12 wt % povidone K25, 2 wt % to 35 wt % sodium croscarmellose, and 1 wt % to 9 wt % talc or silicon dioxide.

36. The method according to claim 19, wherein the liver disease or disorder is liver fibrosis.

37. The systemic formulation according to claim 3, wherein the at least one acidifier is selected from the group consisting of ascorbic acid, oxalic acid, malonic acid, succinic acid, glutaric acid, tartaric acid, fumaric acid, maleic acid, malic acid, adipic acid, glutamic acid, citric acid, and sodium hydrogen citrate.

38. The method according to claim 26, wherein the at least one acidifier is selected from the group consisting of ascorbic acid, oxalic acid, malonic acid, succinic acid, glutaric acid, tartaric acid, fumaric acid, maleic acid, malic acid, adipic acid, glutamic acid, citric acid, and sodium hydrogen citrate.

* * * * *